US012648913B2

(12) United States Patent
Duvall et al.

(10) Patent No.: US 12,648,913 B2
(45) Date of Patent: Jun. 9, 2026

(54) POLYMERIC NANOCARRIERS AND METHODS OF USE THEREOF

(71) Applicant: Vanderbilt University, Nashville, TN (US)

(72) Inventors: Craig L Duvall, Nashville, TN (US); Joseph Paul Vanderburgh, Nashville, TN (US); Mukesh K. Gupta, Nashville, TN (US); Scott A. Guelcher, Nashville, TN (US); Julie A. Rhoades, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/844,870

(22) Filed: Apr. 9, 2020

(65) Prior Publication Data

US 2020/0323785 A1 Oct. 15, 2020

Related U.S. Application Data

(60) Provisional application No. 62/831,579, filed on Apr. 9, 2019.

(51) Int. Cl.
| | |
|---|---|
| *A61K 31/444* | (2006.01) |
| *A61K 9/50* | (2006.01) |
| *C08G 81/02* | (2006.01) |

(52) U.S. Cl.
CPC .......... *A61K 9/5026* (2013.01); *A61K 31/444* (2013.01); *C08G 81/024* (2013.01)

(58) Field of Classification Search
CPC .. A61K 31/444; A61K 9/5026; A61K 47/548; A61K 47/6935; C08G 81/024
See application file for complete search history.

(56) References Cited

U.S. PATENT DOCUMENTS

2015/0125391 A1* 5/2015 Swami ................. A61K 47/548
424/9.1

OTHER PUBLICATIONS

Gupta et al. (Adv. Funct. Mater. 2017, 27, 1704107) (Year: 2017).*
Van Drissche et al. (Chem of Mater. 2018, 8587-8596) (Year: 2018).*
Kavanaugh et al. (Ostearthritis and Cartilage 25(2017) S265-S266). (Year: 2017).*
Vanderburg et al. (43rd Annaual European Calcified Tissue Society Coongress, vol. 5. 2016; Poster: Encapsulation of Gli-inhibitors bocks tumore invasion into the bone) (Year: 2016).*
Carbone, E. J.; Rajpura, K.; Allen, B. N.; Cheng, E.; Ulery, B. D.; Lo, K. W. H. Osteotropic Nanoscale Drug Delivery Systems Based on Small Molecule Bone-Targeting Moieties. Nanomedicine Nanotechnology, Biol. Med. 2017, 13, 37-47.

(Continued)

*Primary Examiner* — Ali Soroush
(74) *Attorney, Agent, or Firm* — Stites & Harbison PLLC; Richard S. Myers, Jr.

(57) ABSTRACT

A polymeric nanocarrier and method of treating a bone disease are provided. The polymeric nanocarrier includes an amphiphilic copolymer including a hydrophobic block and a hydrophilic block, where the hydrophilic block comprises a random copolymer. The method of treating a bone disease includes administering the polymeric nanocarrier to a subject in need thereof.

13 Claims, 28 Drawing Sheets

(56)          References Cited

OTHER PUBLICATIONS

Cole, L. E.; Vargo-Gogola, T.; Roeder, R. K. Targeted Delivery to Bone and Mineral Deposits Using Bisphosphonate Ligands. Adv. Drug Deliv. Rev. 2016, 99, 12-27.

Gupta, M. K.; Meyer, T. a.; Nelson, C. E.; Duvall, C. L. Poly(PS-b-DMA) Micelles for Reactive Oxygen Species Triggered Drug Release. J. Control. Release 2012, 162, 591-598.

Hengst, V.; Oussoren, C.; Kissel, T.; Storm, G. Bone Targeting Potential of Bisphosphonate-Targeted Liposomes: Preparation, Characterization and Hydroxyapatite Binding in Vitro. Int. J. Pharm. 2007, 331, 224-227.

Li, C.; Zhang, Y.; Chen, G.; Hu, F.; Zhao, K.; Wang, Q. Engineered Multifunctional Nanomedicine for Simultaneous Stereotactic Chemotherapy and Inhibited Osteolysis in an Orthotopic Model of Bone Metastasis. Adv. Mater. 2017, 29, 1605754.

Liu, P.; Sun, L.; Zhou, D.; Zhang, P.; Wang, Y.; Li, D.; Li, Q.; Feng, R.-J. Development of Alendronate-Conjugated Poly (Lactic-Co-Glycolic Acid)-Dextran Nanoparticles for Active Targeting of Cisplatin in Osteosarcoma. Sci. Rep. 2015, 5, 17387.

Low, S. A.; Kopeček, J. Targeting Polymer Therapeutics to Bone. Adv. Drug Deliv. Rev. 2012, 64, 1189-1204.

Murphy, M. B.; Hartgerink, J. D.; Goepferich, A.; Mikos, A. G. Synthesis and in Vitro Hydroxyapatite Binding of Peptides Conjugated to Calcium-Binding Moieties. Biomacromolecules 2007, 8, 2237-2243.

Onishi, T.; Hayashi, N.; Theriault, R. L.; Hortobagyi, G. N.; Ueno, N. T. Future Directions of Bone-Targeted Therapy for Metastatic Breast Cancer. Nat. Rev. Clin. Oncol. 2010, 7, 641-651.

Ross, R. D.; Cole, L. E.; Roeder, R. K. Relative Binding Affinity of Carboxylate-, Phosphonate-, and Bisphosphonate-Functionalized Gold Nanoparticles Targeted to Damaged Bone Tissue. J. Nanoparticle Res. 2012, 14, 1175.

Ross, R. D.; Roeder, R. K. Binding Affinity of Surface Functionalized Gold Nanoparticles to Hydroxyapatite. J. Biomed. Mater. Res.—Part A 2011, 99 A, 58-66.

Uddin, M. J.; Werfel, T. A.; Crews, B. C.; Gupta, M. K.; Kavanaugh, T. E.; Kingsley, P. J.; Boyd, K.; Marnett, L. J.; Duvall, C. L. Fluorocoxib A Loaded Nanoparticles Enable Targeted Visualization of Cyclooxygenase-2 in Inflammation and Cancer. Biomaterials 2016, 92, 71-80.

Wang, H.; Liu, J.; Tao, S.; Chai, G.; Wang, J.; Hu, F.-Q.; Yuan, H. Tetracycline-Grafted PLGA Nanoparticles as Bone-Targeting Drug Delivery System. Int. J. Nanomedicine 2015, 10, 5671-5685.

Wright, J. E. I.; Gittens, S. A.; Bansal, G.; Kitov, P. I.; Sindrey, D.; Kucharski, C.; Uludağ, H. A Comparison of Mineral Affinity of Bisphosphonate-Protein Conjugates Constructed with Disulfide and Thioether Linkages. Biomaterials 2006, 27, 769-784.

Yamashita, S.; Katsumi, H.; Hibino, N.; Isobe, Y.; Yagi, Y.; Kusamori, K.; Sakane, T.; Yamamoto, A. Development of PEGylated Carboxylic Acid-Modified Polyamidoamine Dendrimers as Bone-Targeting Carriers for the Treatment of Bone Diseases. J. Control. Release 2017, 262, 10-17.

Yamashita, S.; Katsumi, H.; Hibino, N.; Isobe, Y.; Yagi, Y.; Tanaka, Y.; Yamada, S.; Naito, C.; Yamamoto, A. Development of PEGylated Aspartic Acid-Modified Liposome as a Bone-Targeting Carrier for the Delivery of Paclitaxel and Treatment of Bone Metastasis. Biomaterials 2018, 154, 74-85.

* cited by examiner

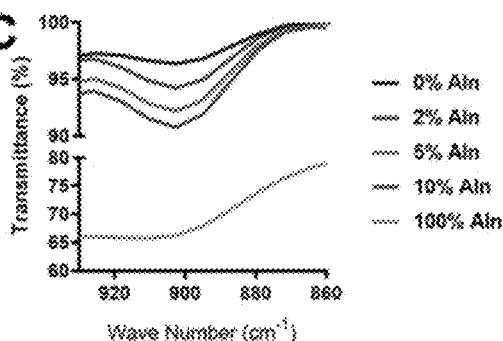
| % Aln | 0 | 2 | 5 | 10 | 100 |
|---|---|---|---|---|---|
| Theoretical DP (%) | 0/150 | 3/147 | 8/142 | 15/135 | 150/0 |
| Experimental Aln DP (%) | 0 | 4 | 8 | 13 | * |
FIG. 1B
FIG. 1C
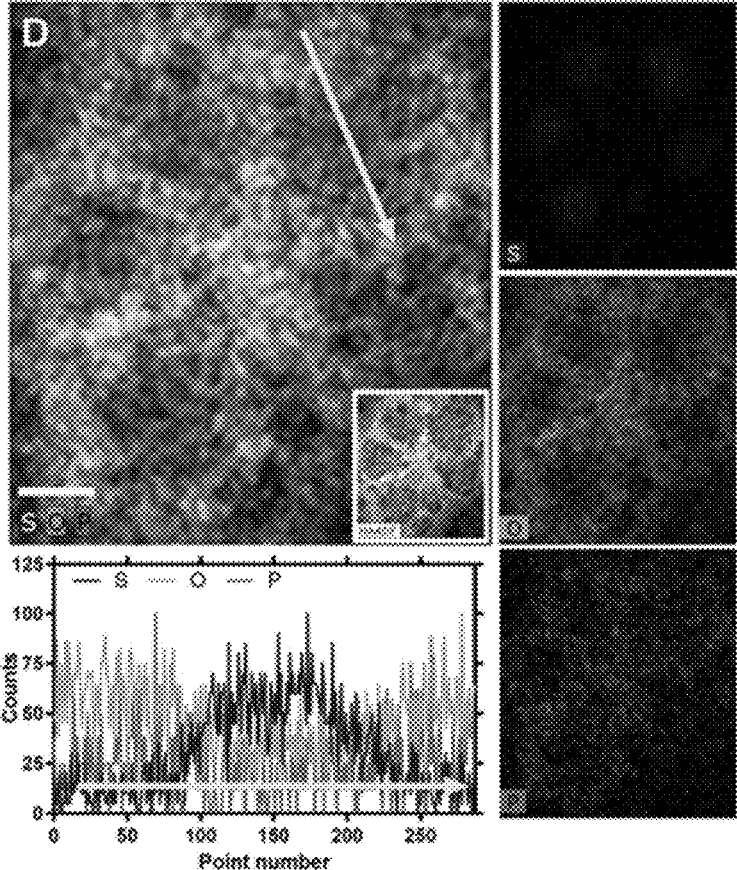
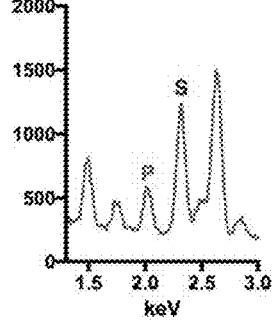
FIG. 1D
FIG. 1E

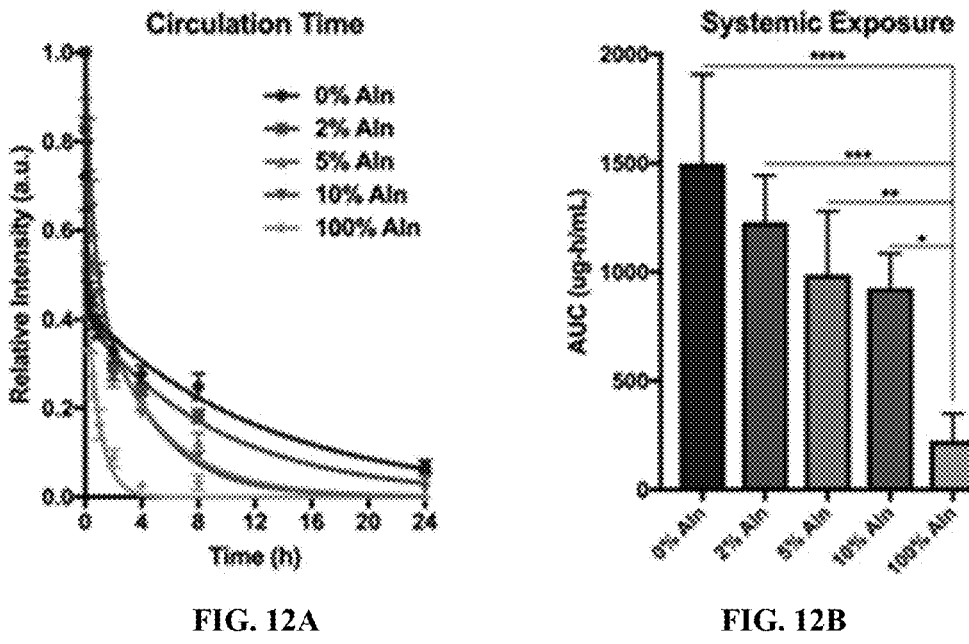
FIG. 12A          FIG. 12B
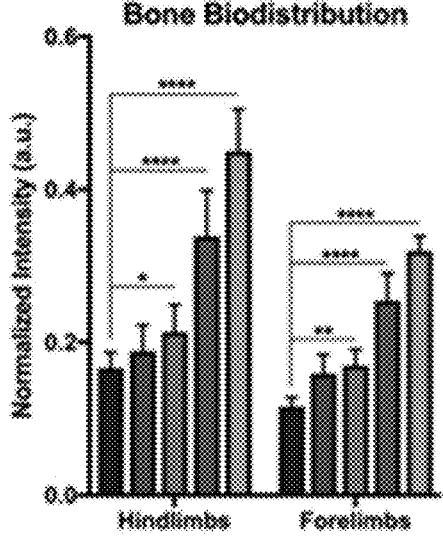
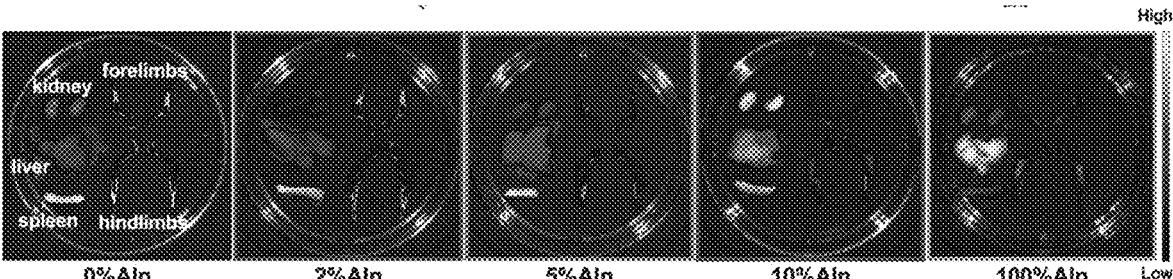
FIG. 12C

POLYMERIC NANOCARRIERS AND METHODS OF USE THEREOF

RELATED APPLICATIONS

This application claims the benefit of U.S. Provisional Application Ser. No. 62/831,579, filed Apr. 9, 2019, the entire disclosure of which is incorporated herein by this reference.

GOVERNMENT INTEREST

This invention was made with government support under grant numbers W81XWH-15-1-0627 and W81XWH-15-1-0622 awarded by the Department of Defense (DOD), R01CA163499 awarded by the National Institutes of Health (NIH), and 1I01BX001957 awarded by the Department of Veterans Affairs. The government has certain rights in the invention.

TECHNICAL FIELD

The present-disclosed subject matter relates to polymeric nanocarriers and methods of use thereof. In particular, the presently-disclosed subject matter relates to bone-binding, ROS-responsive polymeric nanocarriers and methods of use thereof for drug delivery.

BACKGROUND

Metastasis is the major prognostic factor for breast cancer patient survival. Breast tumors in particular have a propensity to metastasize to bone, with over 70% of patients having bone metastases post-mortem. After metastasis to bone, breast cancer cells disrupt normal bone remodeling to initiate a vicious cycle of tumor-induced bone disease (TIED). Bone breakdown releases stores of matrix-bound growth factors, including transforming growth factor beta (TGF-β), that further stimulate tumor growth and osteolytic bone destruction, propagating the cycle. As a result of this tumor growth and bone destruction, patients presenting with bone metastases often experience significant skeletal complications such as severe bone pain, increased risk of pathological fracture, a reduction in mobility, and other skeletal-related events (SREs) that significantly reduce quality of life.

Tumor cells in the bone microenvironment secrete parathyroid hormone-related protein (PTHrP) which upregulates osteoblast expression of receptor activator of nuclear factor kappa-B ligand (RANKL), driving subsequent osteoclast activation and resorption of the bone matrix. Current treatment strategies for TIBD include anti-resorptives such as bisphosphonates and the RANKL inhibitor, denosumab. These agents systemically inhibit osteoclast activity to reduce bone resorption, which at high doses can be associated with disrupted bone homeostasis at non-tumor sites. In view thereof, recent research has focused on the transcription factor Gli2, which drives expression of PTHrP. For example, genetic repression of Gli2 in bone-metastatic tumor cells has been shown to significantly reduce tumor-induced bone destruction. However, while small molecule inhibitors of Gli2 have been identified, their use in treating TIBD in vivo has not been studied extensively.

Accordingly, there remains a need for compositions and methods that provide improved treatments for TIBD that more potently and selectively target tumor-induced bone destruction while limiting off-target effects.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a polymeric nanocarrier, comprising an amphiphilic copolymer including a hydrophobic block and a hydrophilic block, where the hydrophilic block comprises a random copolymer. In some embodiments, the hydrophobic block comprises a hydrophobic and reactive oxygen species (ROS)-degradable polymer. In one embodiment, the hydrophobic block comprises poly(propylene sulfide) (PPS). In some embodiments, the hydrophilic block comprises a hydrophilic monomer and an amine-reactive monomer. In one embodiment, the hydrophilic block comprises poly(N, N-dimethylacrylamide) (PDMA) and poly(pentafluorophenyl acrylate) (PPFPA). In one embodiment, the hydrophilic block further includes amine-terminated alendronate (Aln) grafted to the amine-reactive monomer. In one embodiment, the amine-reactive monomer includes poly(pentafluorophenyl acrylate) (poly(PFPA)). In another embodiment, the hydrophilic block includes between 2% and 100% of the PFPA. In one embodiment, the hydrophilic block includes between 2% and 100% of alendronate (Aln) grafted to the PFPA.

In some embodiments, the hydrophobic block comprises a degree of polymerization of 135. In some embodiments, the hydrophilic block comprises a degree of polymerization of 150. In some embodiments, the nanocarrier further includes an active agent encapsulated therein. In one embodiment, the active agent comprises a hydrophobic small molecule. In one embodiment, the active agent comprises a small molecule therapeutic inhibitor. In one embodiment, the active agent comprises a Gli-inhibitor. In one embodiment, the active agent comprises GANT58.

Also provided herein, in some embodiments, is a polymeric nanocarrier including $(poly(propylene\ sulfide))_{135}$-b-$((alendronate)_x$-co-$(poly(N,N-dimethylacrylamide))_y)_{150}$; where x is between 3 and 15 and y is between 135 and 147. In one embodiment, x is about 15 and y is about 135.

Further provided herein, in some embodiments, is a method of treating a bone disease, the method comprising administering the polymeric nanocarrier to a subject in need thereof. In one embodiment, the nanocarrier further comprises an active agent encapsulated therein.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIGS. 1A-E show images and graphs illustrating GANT58-BTNP synthesis and TEM characterization validating BTNP structure. (A) Synthesis of $PPS_{135}$-b-P(Aln-co-DMA)$_{150}$ polymer and subsequent BTNP micelle fabrication. (B) Targeted and measured degree of polymerization (DP) of Aln (X, magenta), DMA (Y, green) in each polymer series. Aln DP measurements based on spectrophotometric quantification using a cation-chelation competition assay. Resulting BTNPs are denoted by the target % Aln in the hydrophilic, NP surface-forming block (0% Aln, 2% Aln, 5% Aln, 10% Aln, 100% Aln). *due to a lack of certainty in the MW of 100% Aln polymer resulting from insolubility in the GPC solvent, we refrain from estimating the Aln DP of 100% Aln polymer. However, the 100% Aln polymer contains ~10× the moles of Aln per mass of polymer than the 10% Aln polymer. (C) FTIR spectrum of BTNP polymers. (D) STEM-EDS characterization of 10% Aln formulation using chemical mapping and EDS line scan over the length of a single micelle (yellow arrow, analysis on bottom left). Sulfur (blue), oxygen (green), and phosphorus (magenta) were used as signatures for PPS, DMA, and Aln, respectively. Scale bar: 30 nm. (E) EDS spectra of 10% Aln (left) and 0% Aln (right) formulation, highlighting the consistent sulfur (S, component of PPS) and different phosphorus (P, component of Aln) peak magnitudes.

FIGS. 2A-E show graphs illustrating $PPS_{135}$-b-P(Aln-co-DMA)$_{150}$ polymer characterization. (A) $^{19}$F NMR spectra of (i) $PPS_{135}$-b-P(PFPA$_{15}$-co-DMA$_{135}$) and (ii) $PPS_{135}$-b-P(Aln$_{15}$-co-DMA$_{135}$) in CDCl$_3$. The disappearance of peaks at −162.6, −158.4, −158.9 indicate the grafting of alendronate in diblock copolymer of $PPS_{135}$-b-P(Aln$_{15}$-co-DMA$_{135}$). (B) $^{1}$H NMR spectra of (i) $PPS_{135}$-OH, (ii) $PPS_{135}$-ECT, (iii) $PPS_{135}$-b-P(Aln$_{15}$-co-DMA$_{135}$) in CDCl$_3$ solvent. The presence of characteristic peaks at each step indicate successful formation of precursor and final diblock copolymer of $PPS_{135}$-b-P(Aln$_{15}$-co-DMA$_{135}$). (C) $^{1}$H NMR spectra of 2%, 5%, 10%, and 100% Aln in diblock copolymer of $PPS_{135}$-b-P(Aln$_x$-co-DMA$_y$) in DMSO-d6. (D) DMF GPC refractive index traces of $PPS_{135}$-ECT, $PPS_{135}$-b-P(Aln$_3$-co-DMA$_{147}$) (2% Aln), $PPS_{135}$-b-(Aln$_8$-co-DMA$_{142}$) (5% Aln), $PPS_{135}$-b-(Aln$_{15}$-co-DMA$_{135}$) (10% Aln). (E) FT-IR spectra of 0%, 2%, 5%, 10%, 100% Aln in diblock copolymer of $PPS_{135}$-b-P(Aln$_x$-co-DMA$_y$) and Aln only. The increased Aln in diblock copolymers were identified based on stretching vibration resulting from the P—O bond in Aln at ~910 cm$^{-1}$ (gray dotted line). An increase in peak intensity with increasing Aln content in the polymers indicates a greater amount of Aln grafting through the amine-reactive PFPA chemistry.

FIGS. 7A-C show graphs illustrating GANT58-BTNP cargo retention in serum. (A-C) FRET pair DU-DiO were loaded into BTNPs and FRET efficiency was measured at prescribed times after incubation in (A) 0% fetal bovine serum (FBS), (B) 10% FBS, and (C) 25% FBS.

FIGS. 12A-E show graphs and images illustrating GANT58-BTNP pharmacokinetics and biodistribution that indicate 10% Aln provides an ideal balance of bone binding and vascular bioavailability associated with reduced liver clearance. (A) Circulation time of Cy5-grafted BTNPs as assessed by tail-nick method. (B) Area under the curve measurements calculated by integration of circulation time curves. (C) Cy5 fluorescence quantification of GANT58-Cy5BTNP distribution to bone 24 hr after injection relative to soft tissue with representative images below. (D) Bone: liver ratios quantified by Cy5 fluorescence at 24 hr after injection. (E) GANT58 biodistribution in tumor-associated bone and nontumor-bearing bone after GANT58-10% Aln and GANT58-0% Aln i.v. administration as assessed by HPLC. Circulation time of Cy5-grafted BTNPs as assessed by tail-nick method.

Figure 1A:
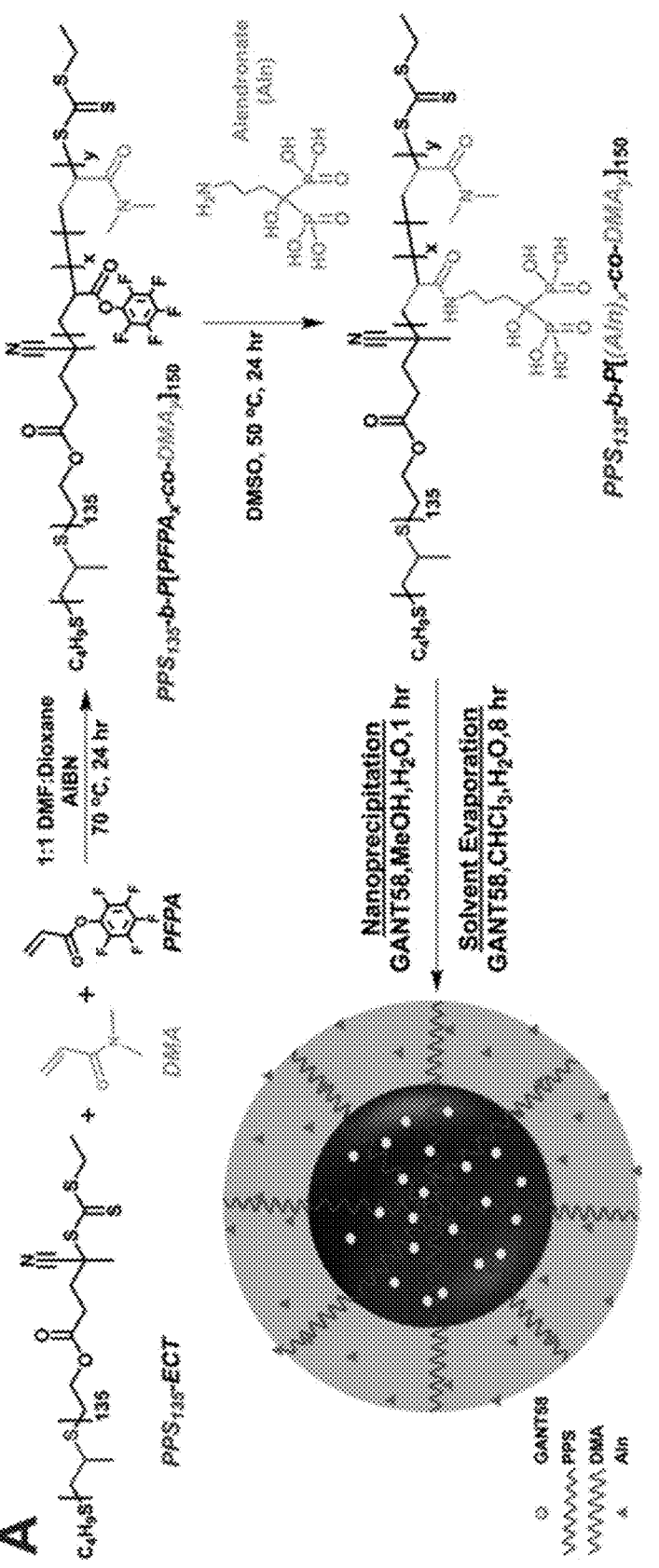

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a polymeric nanocarrier. In some embodiments, the polymeric nanocarrier includes copolymers. In one embodiment, the copolymers are block copolymers. The block copolymers may include any suitable number of blocks including, but not limited to, a first block and a second block. In another embodiment, at least one of the copolymers includes a bisphosphonate, such as, but not limited to, alendronate (Aln). In a further embodiment, the block copolymers are amphiphilic. For example, in one embodiment, the first block is hydrophobic and/or reactive oxygen species (ROS)-degradable, and the second block is hydrophilic. In another embodiment, the first block includes a hydrophobic and ROS-degradable polymer such as, but not limited to, poly(propylene sulfide) (PPS). In a further embodiment, the second block includes a random copolymer of hydrophilic monomers and amine-reactive monomers, such as, but not limited to, a random copolymer of hydrophilic poly(N,N-dimethylacrylamide) (PDMA) and amine-reactive intermediate group poly(pentafluorophenyl acrylate) (PPFPA). Other suitable amine-reactive monomers include, but are not limited to, 2-vinyl-4,4-dimethylazlactone (VDMA).

Additionally or alternatively, in some embodiments, the copolymers are linear and/or self-assembling block copolymers. The polymeric nanocarrier may include any suitable combination of first and second blocks for self-assembly and active agent loading. For example, in some embodiments, the first block is hydrophobic and/or reactive oxygen species (ROS)-degradable and includes a degree of polymerization of at least 5, at least 10, at least 20, at least 25, at least 50, at least 100, up to 500, between 5 and 500, between 25 and 500, between 50 and 500, between 100 and 500, between 5 and 400, between 5 and 300, between 5 and 200, between 50 and 400, between 50 and 300, between 50 and 250, between 50 and 200, between 100 and 200, about 135, or any combination, sub-combination, range, or sub-range thereof. In some embodiments, the second block is hydrophilic and includes a degree of polymerization of at least 5, at least 10, at least 20, at least 25, at least 50, at least 100, up to 500, between 5 and 500, between 25 and 500, between 50 and 500, between 100 and 500, between 5 and 400, between 5 and 300, between 5 and 200, between 50 and 400, between 50 and 300, between 50 and 250, between 50 and 200, between 100 and 200, about 150, or any combination, sub-combination, range, or sub-range thereof. In one embodiment, as discussed in the Examples below, the first block includes a degree of polymerization of 135 units and the second block includes a degree of polymerization of 150 units. In another embodiment, where the first block includes PPS and the second block includes a random copolymer of PPFPA and PDMA, the resulting block copolymer formulation includes $PPS_{135}$-b-$(PPFPA-co-PDMA)_{150}$. Although discussed herein primarily with respect to the aforementioned degrees of polymerization, as will be appreciated by those skilled in the art, the disclosure is not so limited and may include any other suitable degree of polymerization or combination of degrees of polymerization.

The degree of polymerization of the first block may be in any ratio with respect to the degree of polymerization of the second block. For example, the first block may have a higher degree of polymerization, the same degree of polymerization, or a lower degree of polymerization as compared to the second block. In one embodiment, the degree of polymerization of the first block is the same as or less than the degree of polymerization of the second block. In one embodiment, the degree of polymerization of the first block is less than the degree of polymerization of the second block. In some embodiments, a ratio of the degree of polymerization of first block and the second block is between 1:10 and 10:1, between 1:10 and 10:5, between 1:10 and 10:10, between 1:10 and 9:10, between 2:10 and 10:10, between 3:10 and 10:10, between 4:10 and 10:10, between 5:10 and 10:10, between 6:10 and 10:10, between 7:10 and 10:10, between 8:10 and 10:10, about 9:10, or any combination, sub-combination, range, or sub-range thereof.

In addition to varying degrees of polymerization, the second block of the polymeric nanocarrier includes any suitable amine-reactive monomer content. Suitable amine reactive monomer contents include, but are not limited to, between 1% and 99%, 1% and 95%, 1% and 90%, 1% and 80%, 1% and 70%, 1% and 60%, 1% and 50%, 1% and 40%, 1% and 30%, 1% and 25%, 1% and 20%, 2% and 20%, 1% and 15%, 2% and 15%, 5% and 15%, 6% and 14%, 7% and 13%, 8% and 12%, 9% and 11%, about 10%, 10%, or any combination, sub-combination, range, or sub-range thereof. For example, in one embodiment the second block includes between 1% and 20% PFPA and/or VDMA. In another embodiment, the second block includes between 5% and 15% PFPA and/or VDMA. In a further embodiment, the second block includes about 10% PFPA and/or VDMA.

In some embodiments, an amine-terminated compound is grafted onto the amine-reactive monomer. Suitable amine-terminated compounds include, but are not limited to, amine-terminated bisphosphonates (e.g., amine-terminated Aln), amine-terminated fluorescent labels (e.g., Cy5-amine), amine-terminated peptides, or a combination thereof. For example, where the first block includes PPS and the second block includes a random copolymer of PPFPA and PDMA, the amine-terminated Aln is grafted to the PPFPA resulting in a block copolymer formulation of PPS-b-(Aln-co-PDMA). More specifically, where the first block includes a degree of polymerization of 135 units and the second block includes a degree of polymerization of 150 units, the block copolymer formulation includes the formulation $PPS_{135}$-b-$(Aln-co-PDMA)_{150}$. In such embodiments, since the Aln or other bisphosphonate is grafted to the amine-reactive monomer, the content of amine-reactive monomer, such as PFPA, will determine the amount of Aln in the final formulation.

Additionally or alternatively, in some embodiments, the polymeric nanocarrier is directly copolymerized with a bisphosphonate monomer in place of the amine-reactive monomer. That is, rather than grafting the Aln or other bisphosphonate to the amine-reactive monomer post-polymerization, the bisphosphonate monomer is formed first and then incorporated directly through copolymerization of the polymeric nanocarrier. In such embodiments, the content of the bisphosphonate monomer is similar to that of the amine-reactive monomer discussed above. Similarly, the degree of polymerization of the first block and the second block is the same as that for the polymeric nanocarriers including the amine-reactive monomer discussed above.

As will be appreciated by those skilled in the art, the amine-reactive and/or bisphosphonate monomer content is selected to provide a desired bisphosphonate content in the polymeric nanocarrier. In one embodiment, for example, the bisphosphonate facilitates bone binding and the amine-reactive and/or bisphosphonate monomer content is selected to provide a suitable bisphosphonate content for desired bone-binding affinity. In another embodiment, the bisphosphonate content at least partially determines the zeta potential of the nanocarrier. For example, in the $PPS_{135}$-b-(Aln-co-PDMA)$_{150}$ formulation, 0% Aln provides a zeta potential of 0 mV, while 100% Aln provides a zeta potential of −30 mV.

In some embodiments, the polymeric nanocarriers disclosed herein are loaded with one or more active agents. In one embodiment, the polymeric nanocarriers provide high drug loading and/or encapsulation efficiency. For example, in one embodiment, the block copolymers disclosed herein form nanomicelles, with the hydrophobic first block forming a core of the nanomicelle and the hydrophilic second block forming a corona of the nanomicelle. In another embodiment, the hydrophobic first block surrounds the one or more active agents during micelle formation, encapsulating the active agents within the core of the polymeric nanocarrier. In a further embodiment, the polymeric nanocarrier provides high drug loading (15 weight %) and encapsulation efficiency (60%) of GANT58, a small molecule therapeutic inhibitor that is otherwise insoluble and not amenable to systemic delivery. Although described herein primarily with regard to GANT58, as will be appreciated by those skilled in the art, the active agent is not so limited and may include any other suitable active agent, such as, but not limited to, hydrophobic small molecules, small molecule therapeutic inhibitors, Gli-inhibitors, cancer chemotherapeutics, small molecules that are otherwise insoluble and/or not amenable to systemic delivery, or a combination thereof.

Additionally or alternatively, in some embodiments, the polymer nanocarrier includes one or more elements that further increase loading level and/or stability of the active agent. In some embodiments, the one or more active agent loading elements include one or more polymer excipients. In one embodiment, for example, the polymer excipient includes N-2-benzoyloxypropyl methacrylamide (HPMA-Bz). In another embodiment, the polymer nanocarrier includes a fraction of poly(HPMA-Bz), which forms pi-pi stacking interactions with active agents, including drugs such as GANT58, to improve/stabilize loading thereof. In some embodiments, the one or more active agent loading elements include one or more side groups on the hydrophobic block. In one embodiment, for example, the hydrophobic block includes a PPS derivative that has a benzyl side group. In another embodiment, the benzyl side group assists with loading of active agents, such as GANT58, that have ring-structures capable of forming stabilizing pi-pi stacking interactions with benzyl functionalities on the carrier.

The polymeric nanocarrier according to one or more of the embodiments disclosed herein exhibits a tunable bone-binding affinity and/or an oxidative degradation mechanism for release of drug cargo. For example, the polymeric nanocarrier may include self-assembling linear block copolymers containing the bisphosphonate, alendronate (Aln), which exhibits a tunable bone-binding affinity as well as an oxidative degradation mechanism for release of drug cargo.

Also provided herein is a method of forming the polymeric nanocarriers. In some embodiments, synthesis of the nanocarriers includes ring opening and RAFT polymerization. For example, in one embodiment, the $PPS_{135}$-b-(Aln-co-PDMA)$_{150}$ block copolymer is synthesized via PPFPA intermediate with well-defined molecular weight by controlled ring opening and RAFT polymerization. In another embodiment, the random copolymer of the intermediate hydrophilic coronal block, which includes the neutral surface-charged, hydrophilic PDMA and the highly amine-reactive PPFPA, facilitates grafting of the alendronate under mild reaction conditions. Additionally or alternatively, in some embodiments, the polymeric nanocarrier may optionally be fluorescently labeled by grafting an amine-functionalized fluorophore to the PPFPA intermediate. This fluorescent labeling of the nanocarriers allows for in vivo tracking of the polymer carrier and/or tracking of the drug and polymer independently and simultaneously. Following synthesis of the block copolymers, the nanocarriers may be loaded with active agent(s). For example, in one embodiment, the block copolymers spontaneously form nanomicelles via a simple solvent evaporation (oil-in-water) or nanoprecipitation method. During the nanomicelle formation, the polymeric nanocarriers encapsulate the one or more active agents.

Further provided herein is a method of delivering active agents with the polymeric nanocarriers. The polymeric nanocarriers are delivered by any suitable method, including, but not limited to, intravenously. In some embodiments, the method includes administering the polymeric nanocarriers loaded with one or more active agents to a subject in need thereof. In one embodiment, the method includes, prior to administering the polymeric nanocarriers, encapsulating the one or more active agents with the nanocarriers.

In some embodiments, the polymeric nanocarriers are bone-binding, providing targeted delivery of the active agent(s) to the bone microenvironment. For example, in one embodiment, the polymeric nanocarriers are administered intravenously, after which long circulation of the polymeric nanocarriers leads to nonspecific accumulation at sites of bone tumor/inflammation/remodeling that are characterized by vascular leakiness. In another embodiment, the bisphosphonate content provides enhanced bone binding without the poor pharmacokinetics resulting from rapid removal from circulation by phagocytic cells due to higher negative surface charge. In such embodiments, following the non-specific accumulation, the nanocarriers bind to the bone and are retained locally. Additionally or alternatively, the polymeric nanoparticles subsequently provide sustained local release of the encapsulated active agent(s). In some embodiments, for example, the polymeric nanoparticles are ROS-degradable (e.g., PPS), providing controlled release of the active agent(s) through ROS-degradation. Without wishing to be bound by theory, it is believed that this is the first platform to comprise an amphiphilic block copolymer with the hydrophobic, ROS-degradable PPS core block and a hydrophilic coronal block containing the bisphosphonate alendronate and PDMA, conferring both bone-binding affinity and hydrophilic, neutrally-charged "stealth" behavior.

ROS is present in inflamed and other diseased sites in the body, thus the bone-binding, ROS-degradable polymer nanocarriers provide selectivity to the environments within the bone microenvironment in which the nanocarriers will release cargo. Accordingly, the polymer nanocarriers are suitable for delivery of active agents to disease sites including, but not limited to, cancer, osteomyelitis, tumor-induced bone disease (TIBD), or other bone-specific diseases. For example, in one embodiment, the method includes administering the small molecule inhibitor GANT58, which blocks PTHrP expression and obstructs the vicious cycle of TIBD, to a subject in need thereof through targeted, controlled release by the polymeric nanoparticles. In contrast to previous attempts involving administration of GANT58, where the in vitro effects did not translate in vivo, the polymer nanocarriers disclosed herein blocks bone destruction and/or tumor burden in vivo. Although described herein primarily with regard to bone specific diseases, the disclosure is not so limited and includes any other disease where targeted delivery of the active agent(s) to these sites is needed.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

In this Example, a bone-targeted nanoparticle (BTNP) chemistry is developed, characterized, and tested in a mouse model of bone metastasis for its ability to block both bone destruction and tumor burden. More specifically, this Example discusses the development of a stable, long-circulating NP with desirable pharmacokinetics (PK) for tumor distribution while also conferring bone binding for superior drug retention at sites of tumor-induced bone disease (TIBD). Additionally, this Example discusses the ability of the BTNP to deliver a colloidally stabilized version of the hydrophobic and insoluble Gli2 inhibitor GANT58. Furthermore, this Example discusses the ability of GANT58 to block activity of the transcription factor Gli2, and consequently the expression of parathyroid hormone-related protein (PTHrP) by tumor cells, thus disrupting the vicious cycle TIBD and reducing tumor-driven bone resorption. Without wishing to be bound by theory, it is believed that since Gli2 is primarily associated with development, and not normal bone or other tissue function in adults, treatment with GANT58 will target tumor-associated, but not physiological, osteoclast function.

Bone-targeting of nanomedicines in previous studies has been achieved using bisphosphonates, anionic peptides, carboxylic acids, and other phosphate-containing moieties. Anionic charge is a consistent characteristic of these bone targeting ligands, and it can be a challenge to achieve the ideal density of negative charge to bind bone while maintaining sufficient PK and tumor distribution. NPs with highly negative surface charge frequently show poor PK due to scavenger receptor-based removal by macrophages of the reticuloendothelial organs such as liver. Previously, in an application unrelated to bone targeting, NPs with zeta potential of −27, −18, −9, +4, +19, +30, and +37 mV were shown to produce tumor:liver ratios of 0.82, 1.28, 1.75, 1.18, 0.84, 0.60 and 0.40, respectively. To design and optimize a nanocarrier that addresses this tradeoff, the present inventors built from their previous work on reactive oxygen species (ROS)-responsive poly(propylene sulfide) core NPs. In particular, a library of BTNPs with tunable density of bone targeting ligand was created in an effort to balance systemic PK and tumor accumulation with bone binding and retention properties. The bone binding bisphosphonate, alendronate, was used as the targeting ligand because it has the potential to improve bone targeting of GANT58, while simultaneously reducing TIED through the osteoclast inhibitory activity of the bisphosphonate.

Previous work comparing bone-targeting ligands has shown that bisphosphonates exhibit a higher binding affinity than carboxylates and phosphonic acid both in vitro and in vivo. More recent work demonstrated that bisphosphonate conjugation to NPs for targeted chemotherapy delivery can contribute to reduced osteolysis in TIBD, but this team did not study bisphosphonate NP surface density or its pharmacokinetic (PK) or pharmacodynamic (PD) consequences. The effect of bisphosphonate ligand density on bone-binding has been explored in vitro where it was found that a plateau in in vitro bone-binding was observed when NPs with >20% of the NP surface was grafted with bisphosphonate, and thus 20% surface coverage was chosen for in vivo studies. However, these formulations were not tested to understand how ligand density affects in vivo PK/PD. Furthermore, coupling bisphosphonate targeting with delivery of a TIBD inhibitor such as GANT58 to improve bone protection from TIED has not been investigated. Accordingly, this Example studies the effect of ligand density on bisphosphonate-conjugated NPs, both for in vitro bone binding and in vivo systemic PK, and investigates the dual benefit of GANT58 and bisphosphonate therapy in TIBD as enabled by highly controlled polymer chemistries.

Results & Discussion

The BTNP developed herein includes an amphiphilic diblock copolymer of poly[(propylene sulfide)-block- (alendronate acrylamide-co-N,N-dimethylacrylamide)] [PPS-b-P (Aln-co-DMA)] to encapsulate and preferentially deliver a small molecule Gli2-inhibitor, GANT58, to bone-associated tumors. The mol % of the bisphosphonate Aln in the hydrophilic polymer block was varied in order to optimize BTNP targeting to tumor-associated bone by a combination of nonspecific tumor accumulation (presumably through the enhanced permeation and retention effect) and active bone binding. While 100% functionalization with Aln created BTNPs with strong bone binding, these BTNPs had highly negative zeta potential, resulting in shorter circulation time, greater liver uptake, and less distribution to metastatic tumors in bone. However, 10 mol % Aln in the hydrophilic block generated a formulation with a favorable balance of systemic pharmacokinetics and bone binding, providing the highest bone:liver biodistribution ratio amongst formulations tested.

In an intracardiac tumor cell injection model of breast cancer bone metastasis, treatment with the lead candidate GANT58-BTNP formulation decreased tumor-associated bone lesion area 3-fold and increased bone volume fraction in the tibiae of the mice 2.5-fold. Aln dually contributed by both conferring bone-targeting to the GANT58-BTNPs, which increased GANT58 concentration in the tumor-associated bone relative to untargeted NPs, and also provided benefit through the direct antiresorptive therapeutic function of Aln. The dual benefit of the Aln in the BTNPs was supported by the observations that while drug free Aln-containing BTNPs improved bone volume fraction in bone tumor bearing mice, GANT58-BTNPs created better therapeutic outcomes than both unloaded BTNPs and GANT58-loaded untargeted NPs. These findings suggest GANT58-BTNPs have potential to potently inhibit tumor-driven osteoclast activation and resultant bone destruction in patients with bone-associated tumor metastases.

Synthesis of Bone-Binding Diblock Copolymers with Varied Alendronate Content Five diblock copolymers were synthesized comprising a nanocarrier core-forming block of polypropylene sulfide (PPS) with a degree of polymerization of approximately 135 (10 kDa). PPS can efficiently encapsulate hydrophobic small molecules and elicits negligible toxicity upon systemic administration, motivating its selection as the hydrophobic block. Further, PPS is responsive to reactive oxygen species (ROS), which is prevalent in inflamed tissues such as tumor. The sulfide group in PPS reacts with ROS such as hydrogen peroxide to create sulfoxides and sulfones. This reaction causes a phase transition of the polymer from hydrophobic to hydrophilic, resulting in disassembly of the micelle and subsequent cargo release. The PPS block was synthesized via anionic polymerization and conjugated to the reversible addition fragmentation chain transfer (RAFT) chain transfer agent (CTA) 4-cyano-4-(ethylsulfanylthiocarbonyl) sulfanylpentanoic acid (ECT) as previously described to create the RAFT macro-CTA $PPS_{135}$-ECT (FIG. 1A).

Figure 2A:
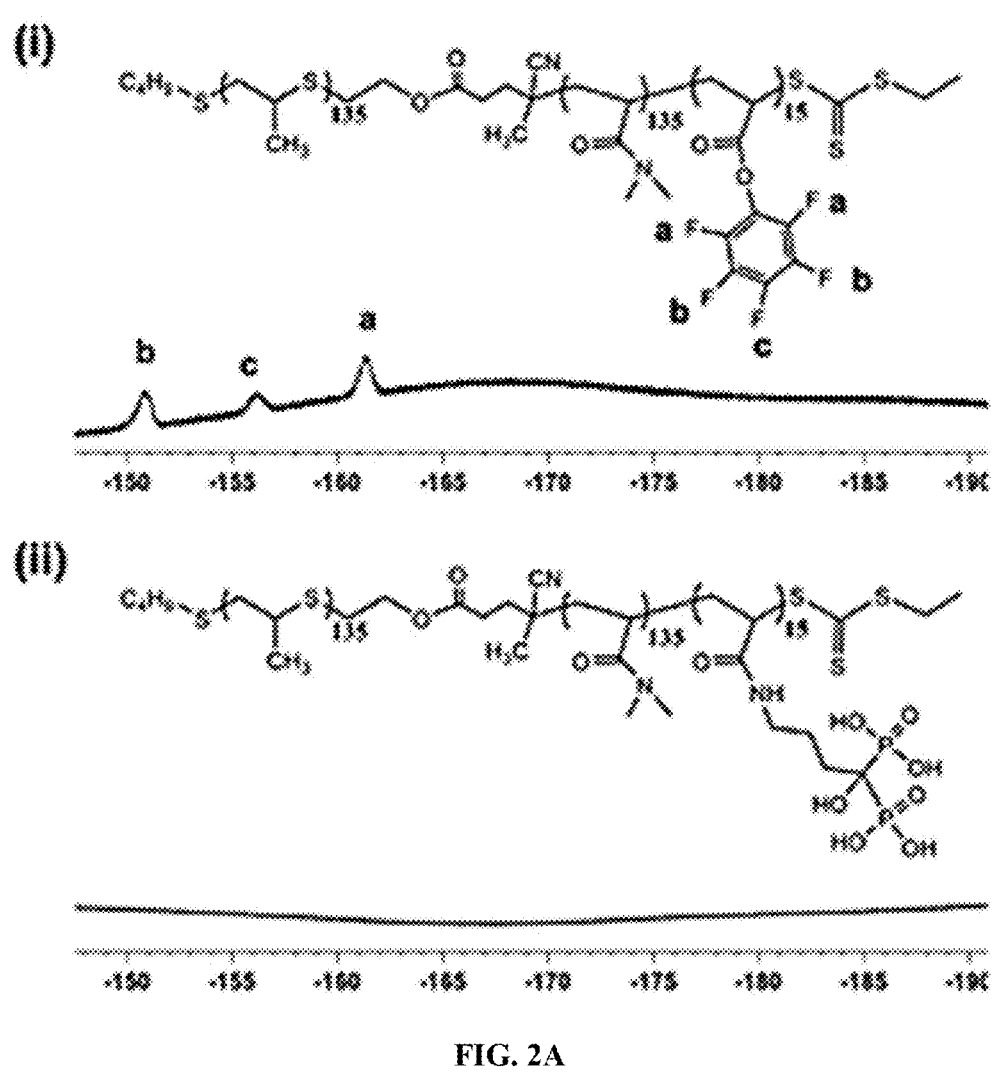
Figure 2B:
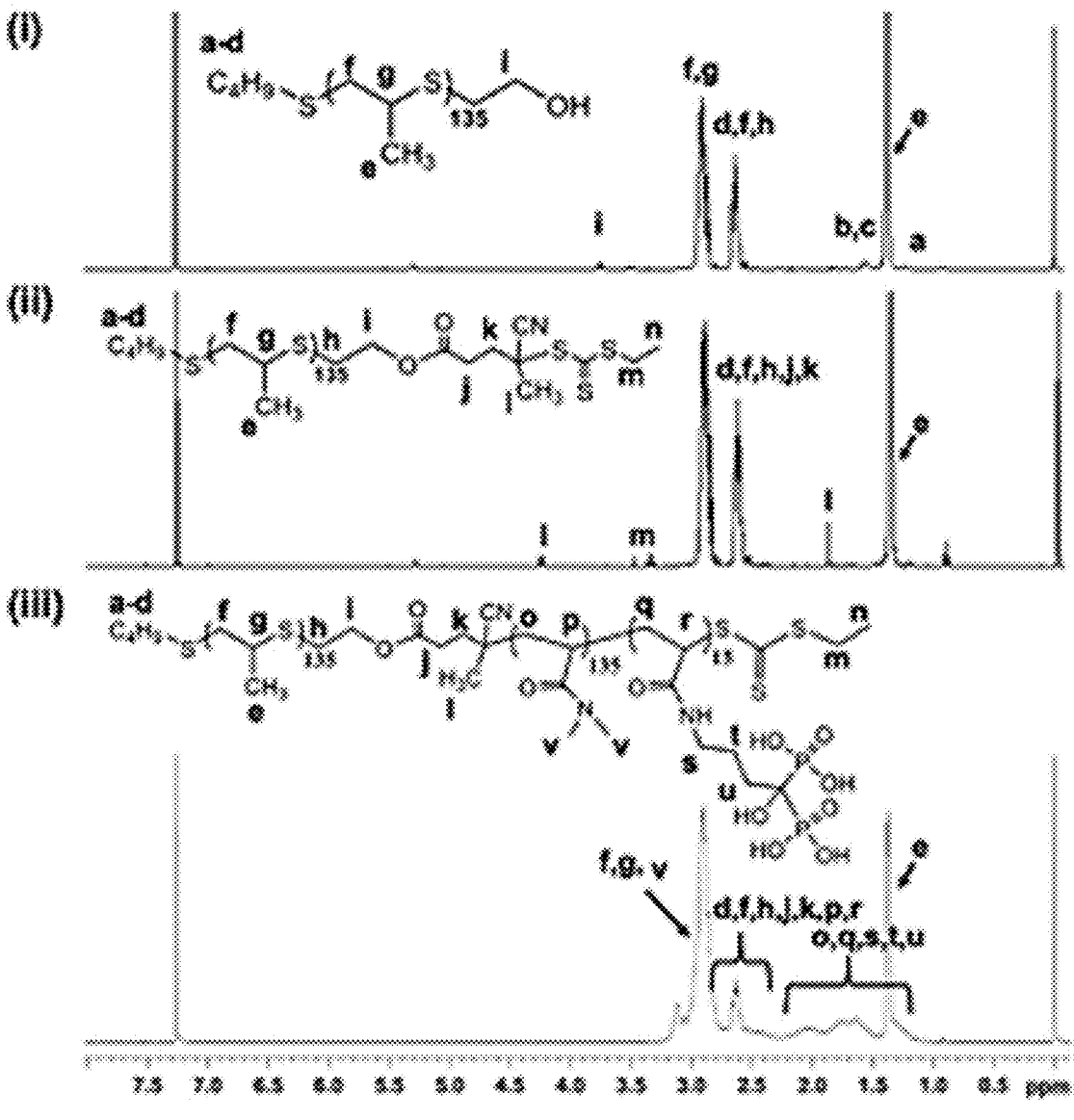
Figure 2C:
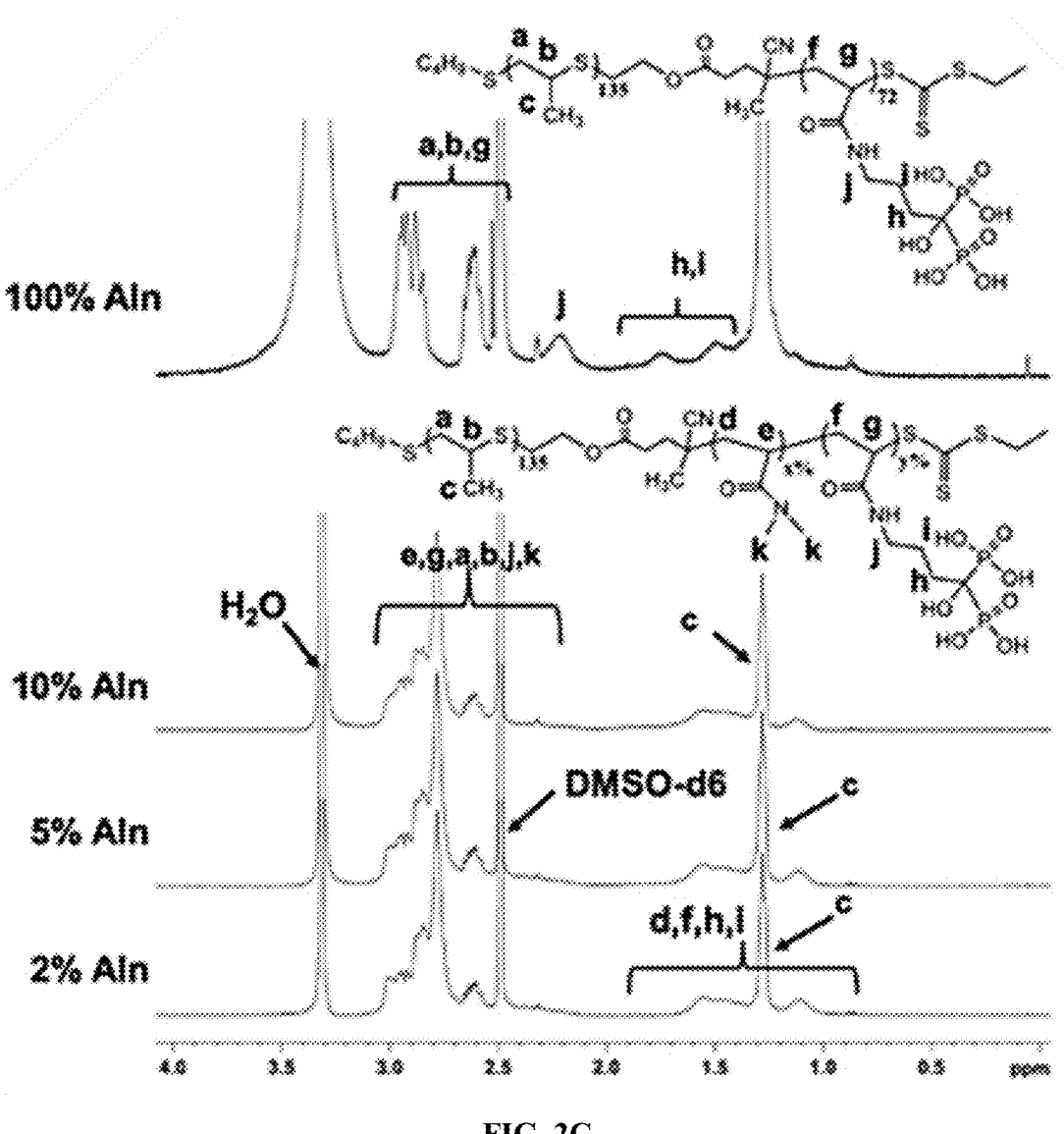
Figure 2D:
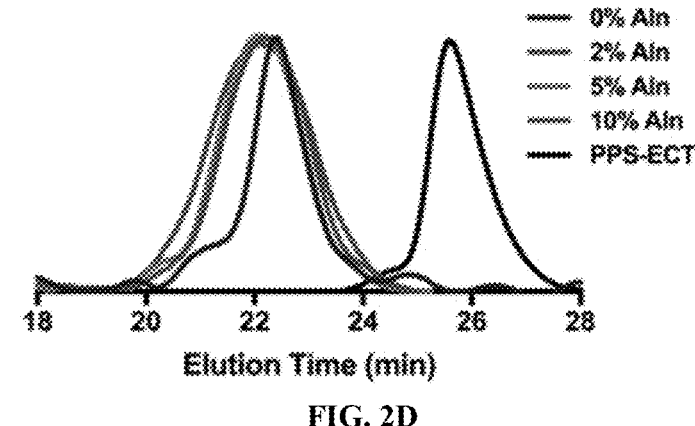
Figure 2E:
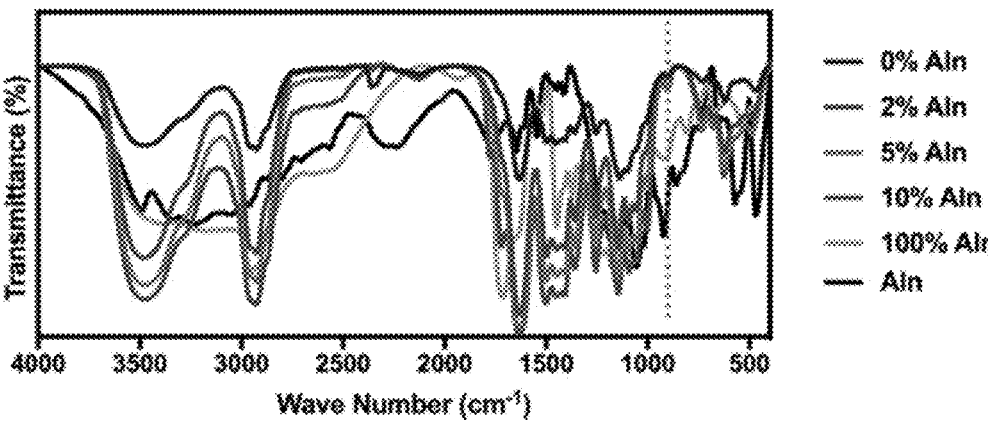

The $PPS_{135}$-ECT was then RAFT polymerization chain extended with a second, hydrophilic block consisting of a random copolymer of N,N-dimethylacrylamide (DMA) and pentafluorophenyl acrylate (PFPA) intermediate which was subsequently reacted with bone-binding alendronate (Aln), yielding $PPS_{135}$-b-P(Aln$_x$-co-DMA$_y$)$_{150}$ (FIGS. 1A and 2A-E). DMA was chosen due to its hydrophilicity, low toxicity, and its short pendant chain length so as to not sterically hinder the engagement of the bone-targeting ligand. PFPA was incorporated into the hydrophilic block to act as an amine-reactive intermediate for grafting of bone-binding Aln. The DMA and PFPA copolymer was targeted to produce a polymer block with a total degree of polymerization of approximately 150. The stoichiometric ratio of DMA:PFPA in the BTNP surface-forming block was varied to create five diblock copolymer formulations with a target of 0%, 2%, 5%, 10%, or 100% PFPA. The primary amine-containing Aln was then grafted via the amine-reactive PFPA intermediate to create BTNPs with a target of 0%, 2%, 5%, 10%, and 100% Aln the NP surface-forming polymer block. By adapting previously used cation-chelation competition assays, the concentration of BTNP-bound Aln was spectrophotometrically quantified exploiting the strong and specific binding of the o-cresolphthalein complexone with $Ca^{2+}$. The experimental DP of Aln was found to be within two units of the theoretical DP for the 0-10% Aln polymer series (FIG. 1B, Table 1). FTIR spectra of the BTNP polymers show a stretching vibration from the P—O bond in Aln at ~910 cm', and an increase in peak intensity with increasing Aln content in polymers indicated Aln content correlated with PFPA content in the parent polymer prior to grafting (FIGS. 1C and 2E). Aln was chosen as the bone-targeting moiety due to its well-documented bone-binding affinity and its accessible terminal primary amine for reactivity with the PFPA group. Importantly, Aln is also a clinically-approved osteoclast inhibitor with the potential to both provide BTNP targeting functionality and also contribute to the bone protective outcomes. To generate fluorescently-labeled BTNPs, Cy5-amine or Cy7-amine fluorescent dyes were grafted to the PFPA block prior to addition of Aln at a 1:1 fluorophore:polymer molar ratio.

TABLE 1

Aln Content Determination. Molar quantity of Aln per mass of polymer in each polymer series spectrophotometrically measured by a cation-chelation competition assay exploiting the strong and specific binding of o-cresolphthalein complexone with $Ca^{2+}$. Bottom row indicates theoretical value based on polymer MW.

| % Aln | 0 | 2 | 5 | 10 | 100 |
|---|---|---|---|---|---|
| mmol Aln/g polymer | BDL | 0.16 | 0.24 | 0.43 | 4.6 |
| Theoretical mmol Aln/g polymer | 0 | 0.12 | 0.30 | 0.53 | |

BDL = below detectable limit

Figure 3A:
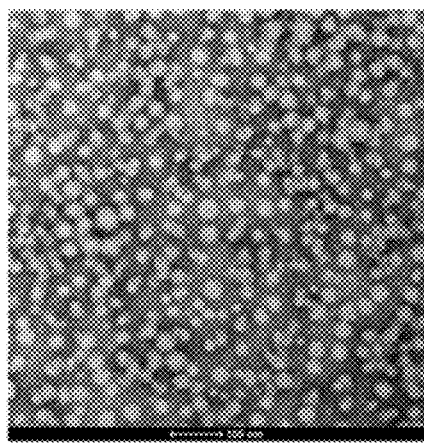
FIGS. 3A-C show an image and graphs of GANT58-BTNP size characterization. (A) Representative TEM image demonstrates the 10% Aln BTNPs exhibit a spherical morphology. (B) 10% Aln BTNPs exhibit a dehydrated diameter of ~38 nm (>100 particles counted). (C) Dynamic light scattering (DLS) of 10% Aln BTNPs shows the micelles have an average hydrodynamic diameter of ~100 nm.
Figure 3B:
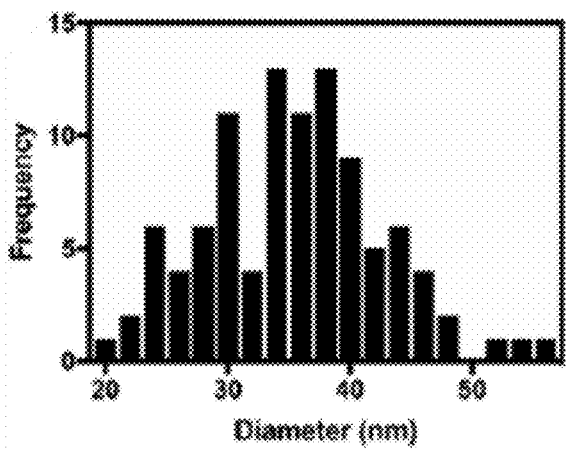
Figure 3C:
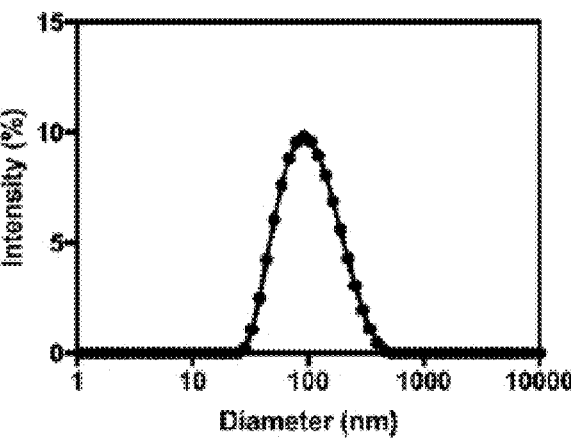
Figure 4A:
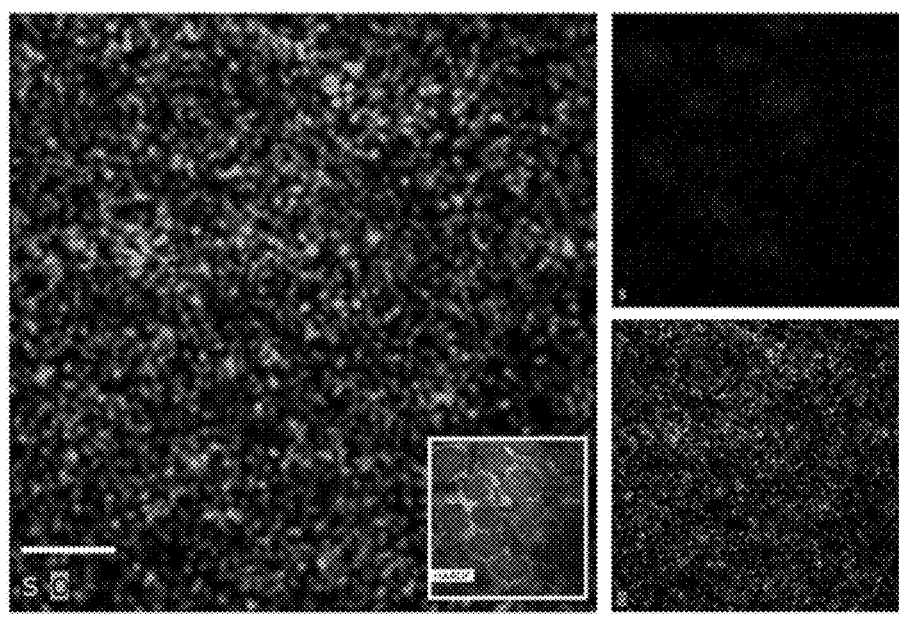
FIGS. 4A-B show images and graphs illustrating BTNP STEM-EDS characterization. (A) 0% Aln formulation chemical mapping using sulfur (blue) and oxygen (green) as signatures for PPS and DMA shows a sulfur-rich core and oxygen-rich corona. Scale bar: 40 nm. (B) Full EDS spectra of both the 10% Aln and 0% Aln formulations. Other characteristic EDS peaks of relevant elements (from TEM grid and buffer) labeled in red.
Figure 4B:
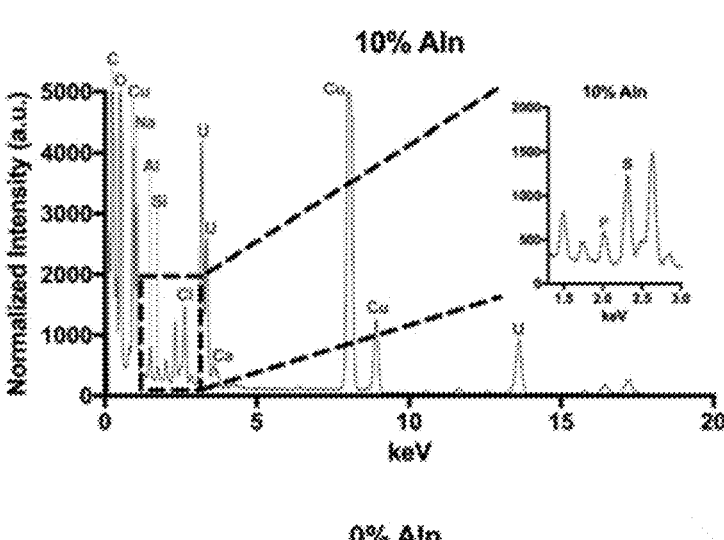
Figure 4B:
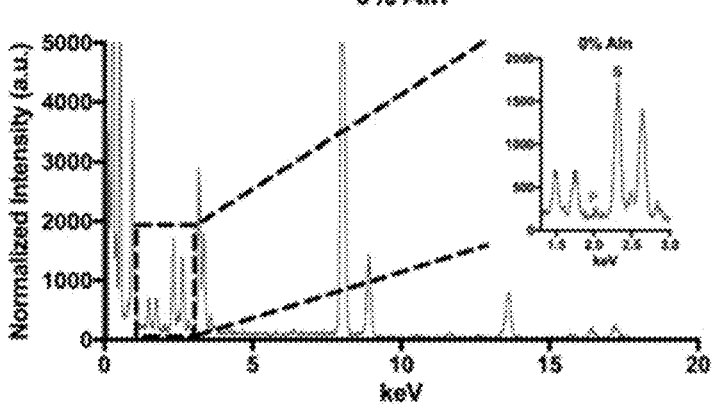

Nanoparticle Preparation and Morphological Characterization. Nanoparticles were formed by a bulk solvent evaporation or nanoprecipitation method to create GANT58-loaded $PPS_{135}$-b-P(Aln-co-DMA)$_{150}$ bone-targeted nanoparticles (GANT58-BTNPs). The GANT58-BTNPs were observed via transmission electron microscope (TEM) in order to confirm the GANT58-BTNPs assume the hypothesized micellar morphology. TEM images indicate the GANT58-BTNPs have a spherical morphology and a diameter of approximately 60 nm in their dehydrated form, and approximately 100 nm in hydrodynamic diameter as measured by dynamic light scattering (DLS) (FIGS. 3A-C). Chemical mapping using Energy Dispersive X-Ray Spectroscopy (EDS) in scanning TEM (STEM) was used to assess chemical content of the BTNPs. Sulfur (blue) was used as the chemical signature for PPS, oxygen (green) for DMA and Aln, and phosphorus (magenta) for Aln. Using these chemical signatures, the BTNP morphology of the 10% Aln formulation was shown to have a sulfur-rich core, and a corona rich in oxygen and sparsely-decorated with phosphorus, suggesting the Aln is randomly interspersed throughout the coronal block (FIG. 1D). Further, the EDS spectra demonstrates that the 10% Aln formulation has a significant phosphorus peak (FIGS. 1E and 4B, left), whereas the 0% Aln formulation (FIG. 4A) lacks a significant phosphorus peak (FIGS. 1E and 4B, right). This suggests the phosphorus signature is indicative of Aln and that it is only present in formulations consisting Aln.

Figure 5A:
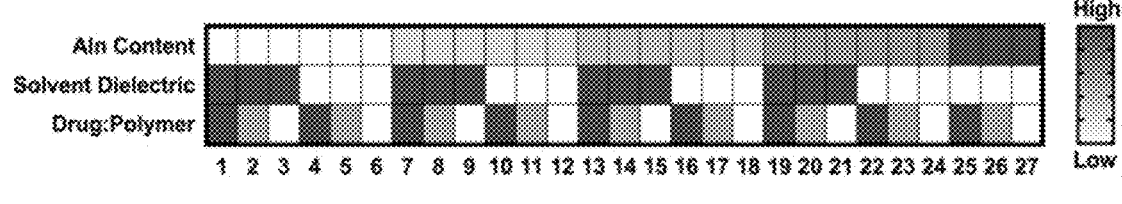
FIGS. 5A-E show graphs illustrating BTNP combinatorial library comparing BTNPs with varying Aln content (0%, 2%, 5%, 10%, and 100% Aln), fabrication methods (nanoprecipitation [low solvent dielectric] and solvent evaporation [high solvent dielectric]), and drug:polymer ratios (1:2, 1:4, and 1:10), fabrication methods, and drug:polymer ratios. (A) Aln content, solvent dielectric, and drug:polymer ratio for various BTNP formulations. (B) BTNP hydrodynamic diameter and (C) zeta potential as measured by DLS. (D) BTNP GANT58 loading and (E) encapsulation efficiency.
Figure 5B:
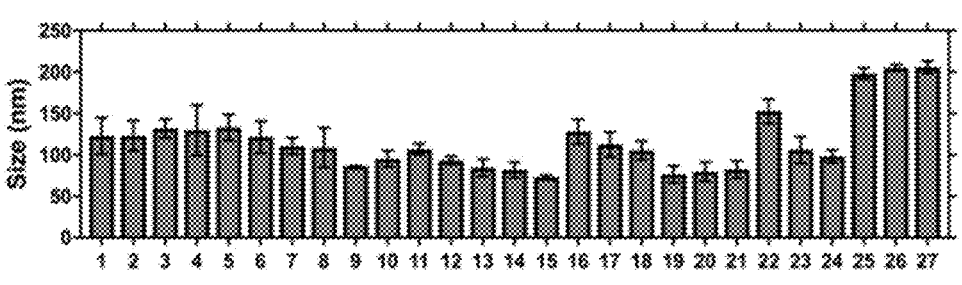
Figure 5C:
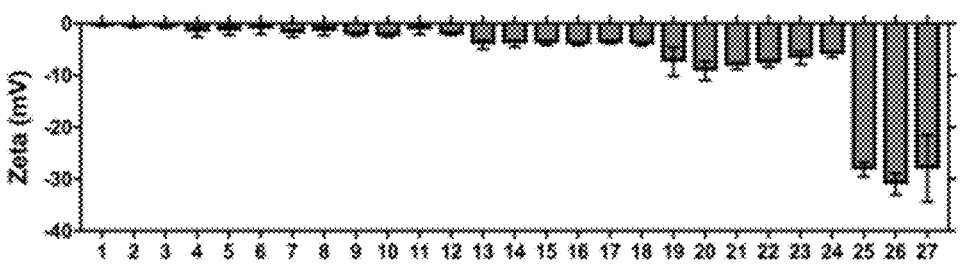
Figure 5D:
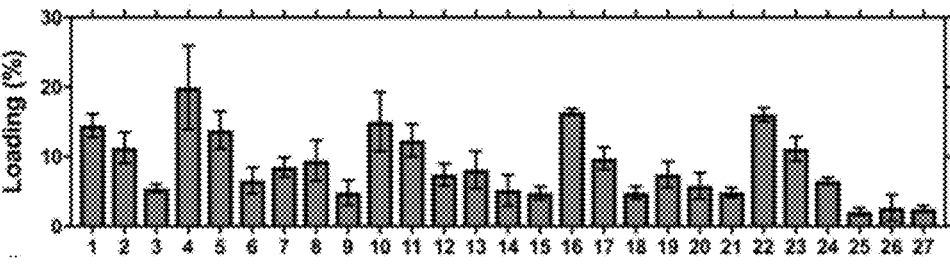
Figure 5E:
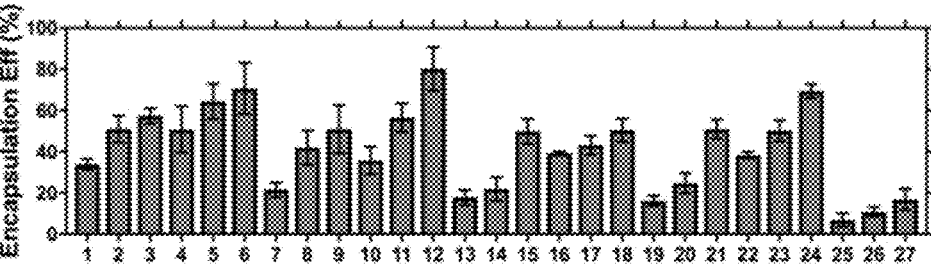

BTNP Preparation Combinatorial Library. Using the five polymers with varied Aln grafting density, two fabrication methods and varying drug:polymer ratios, a BTNP library was created to identify an optimal formulation based on size, zeta potential, and drug loading (FIGS. 5A-E). The hydrodynamic diameter and zeta potential of the BTNPs were assessed by DLS, and GANT58 loading was measured by GANT58 fluorescence (ex. 485 nm em. 590 nm) after 2× dilution in dimethylformamide (DMF). GANT58-BTNPs of all polymer formulations exhibited hydrodynamic diameters of approximately 100 nm except the 100% Aln formulation which exhibited a larger diameter of approximately 200 nm (FIG. 5B). BTNPs formed by the nanoprecipitation method were smaller than those made with the solvent evaporation method (96.9±23.5 nm and 115.1±21.6 nm, respectively, p<0.001), and drug loading had no significant effect on particle size. The surface charge of the BTNPs, as measured by zeta potential, was Aln content-dependent, as anticipated. Increasing Aln content yielded BTNPs with more negative surface charge due to the constituent phosphate groups in Aln (FIG. 5C). GANT58 was pre-dissolved in the organic phase prior to BTNP fabrication runs at drug:polymer mass ratios of 1:2 (high), 1:4, and 1:10 (low), and resultant BTNP GANT58 loading and encapsulation efficiencies were measured (FIGS. 5D-E). The average loading and encapsulation efficiencies were significantly higher (p<0.001) in BTNPs synthesized via the solvent evaporation method (low solvent dielectric) across all drug:polymer ratios. Despite the marginally smaller size of the nanoprecipitation-prepared BTNPs, the increased GANT58 loading achieved in the BTNPs prepared by solvent evaporation is believed to render it the optimal fabrication method. Previous work has shown that nanoparticles of 110 nm have higher tumor:liver ratio than those of 70 nm or 150 nm, further supporting the hypothesis that the solvent evaporation BTNP formulation is a favorable size for tumor delivery. Thus, BTNPs was prepared via the solvent evaporation method for all subsequent experiments. Previous studies have demonstrated the utility of developing combinatorial NP libraries using NP characterization techniques and in vitro screening to identify optimal NP formulations for use in vivo. Here, the development of a combinatorial BTNP library facilitated identification of the fabrication approach to be used for in vivo studies based on BTNP size, surface charge, and drug loading.

Figure 6A:
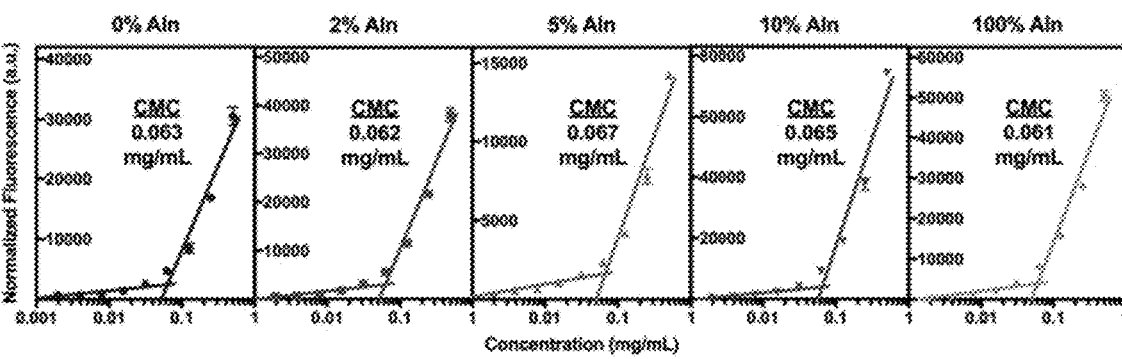
FIGS. 6A-E show graphs illustrating GANT58-BTNP stability and macrophage uptake. (A) Critical micelle concentration of each BTNP formulation as measured by Nile Red method. (B) Salt stability of BTNPs in high salt concentrations (0.5M NaCl) as measured by DLS. (C-D) Serum stability of BTNPs in high serum concentrations (50% FBS) as measured by (C) DLS for NP sizing and (D) FRET for cargo loading stability. (E) RAW 264.7 macrophage uptake of Cy5-labeled BTNPs treated for three hours and analyzed for cell uptake by flow cytometry.
Figure 6B:
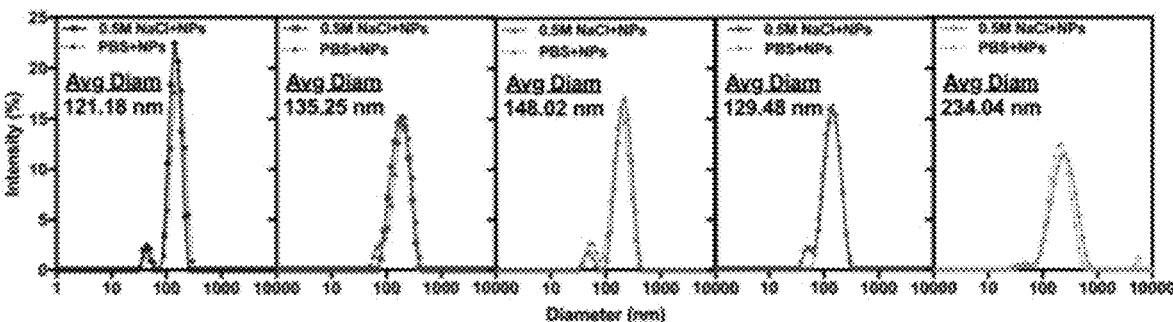
Figure 6C:
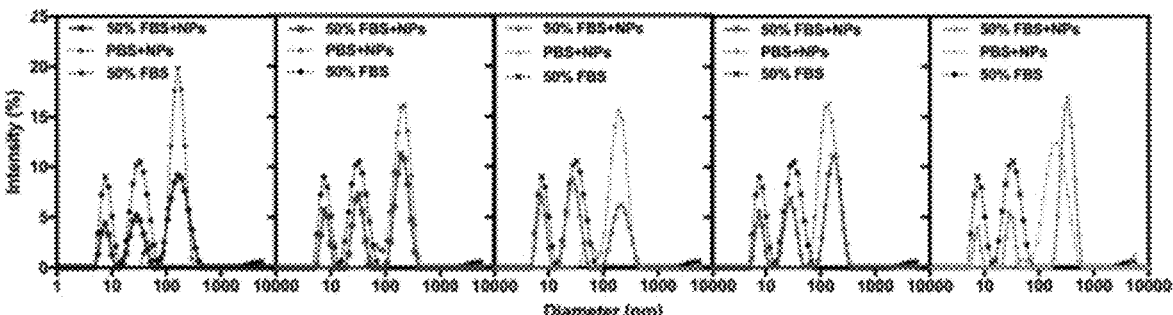
Figure 6D:
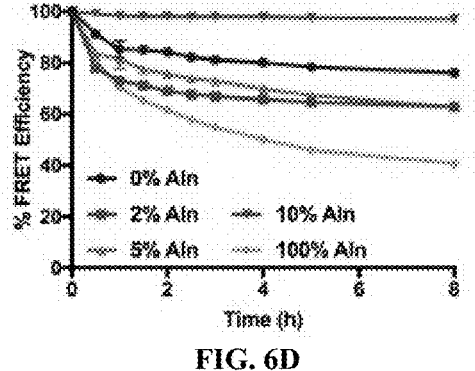
Figure 7C:
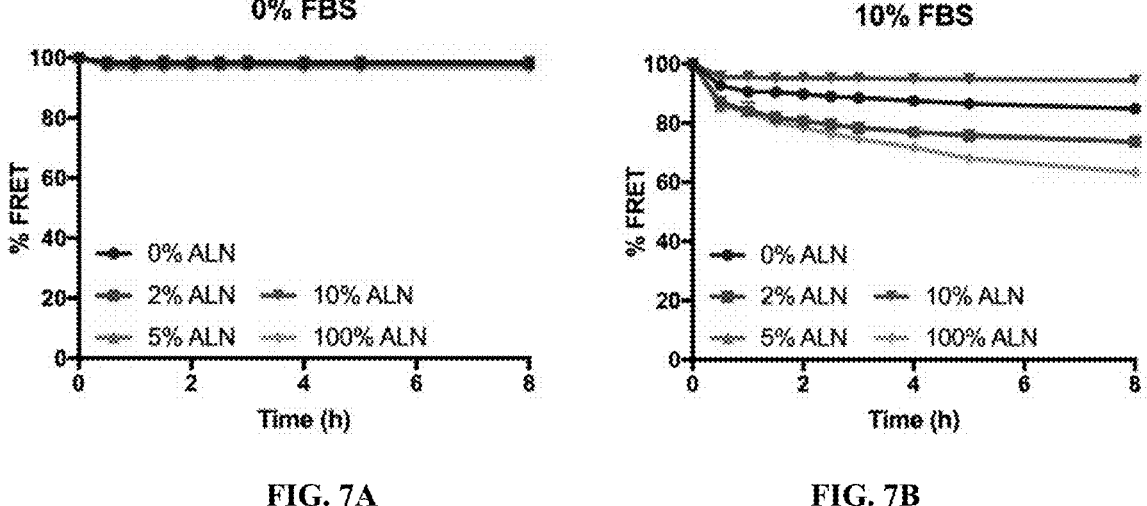
Figure 7C:
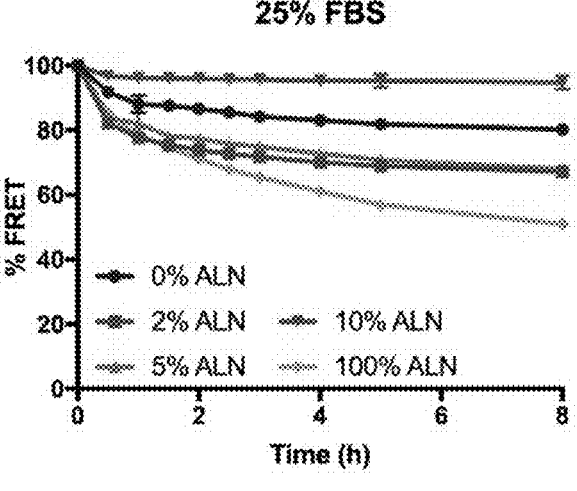

BTNP Stability and Macrophage Uptake. Nanoparticle in vivo bioavailability is essential to maximizing nanoparticle accumulation in tumor-associated bone. Dilution of the nanoparticles upon systemic administration can lead to nanoparticle disassembly due to NP concentration dropping below the critical micelle concentration (CMC). To confirm the CMC of the BTNPs was lower than the initial BTNP blood levels, the CMC was determined by the Nile Red (NR) method (FIG. 6A). The BTNPs were determined to be approximately 0.065 mg/mL for all BTNP formulations which is approximately one order of magnitude lower than the BTNP concentration upon i.v. administration (~0.5 mg/mL). Each BTNP formulation was also stable in high salt concentrations (0.5M NaCl) as measured by DLS, suggesting that the combination of electrostatic and steric repulsion from the P(Aln-co-DMA) BTNP corona provides resistance to salt destabilization (FIG. 6B). BTNP serum stability was also investigated by measuring both NP size and drug retention when challenged with high serum (50% fetal bovine serum, FBS) conditions. DLS measurements showed that BTNP size was largely unaffected by serum incubation except for 100% Aln, for which the average size increased from ~210 nm to ~330 nm upon serum exposure (FIG. 6C). It is believed that this is due to opsonization of serum proteins to the negatively charged surface (−35 mV) of the 100% Aln corona which may cause particle aggregation. To measure model drug retention in the presence of serum, the FRET pair DiI and DiO were co-loaded into BTNPs and incubated in 50% FBS (FIG. 6D). It was found that drug retention is dependent on Aln content in the hydrophilic block, with the 100% Aln formulation exhibiting the fastest loss of encapsulated cargo, further demonstrating the instability of this formulation in serum conditions. Incubation of BTNPs in lower FBS concentrations (0, 10, 25% FBS) resulted in similar yet less pronounced trends, with the BTNPs exhibiting high stability in saline (0% FBS) conditions (FIGS. 7A-C). Notably, the 10% Aln formulation exhibited the highest stability amongst all formulations.

Figure 6E:
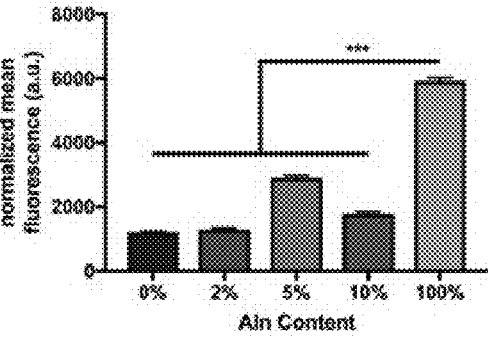

Nanoparticle clearance is often initiated in vivo by uptake into the mononuclear phagocytic system (MPS). Thus, macrophage uptake can be used as a preliminary screen for nanoparticle clearance and PK in vivo. In vitro macrophage uptake experiments showed that the 100% Aln BTNPs exhibit significantly higher macrophage uptake than the lower Aln content formulations (FIG. 6E). Interestingly, the 10% Aln formulation exhibits significantly less uptake than the 5% Aln and 100% Aln formulations. This result aligns with the drug retention findings that showed the 10% Aln is more stable in serum than the other Aln formulations. It is believed that the combination of steric and electrostatic repulsion in the 10% Aln formulation (zeta potential: −8 mV) leads to improved drug retention and shielding from macrophage uptake. Other studies have shown that slightly anionic micelles avoid non-specific organ uptake, improve tumor:liver biodistribution, and a surface charge between 0 and −15 mV leads to minimal macrophage uptake and longer circulation times.

Figure 8A:
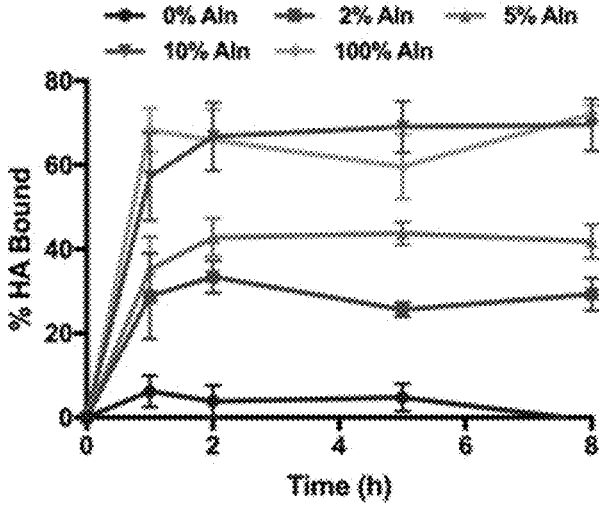
FIGS. 8A-B show a graph and images illustrating GANT58-BTNPs demonstrate high binding affinity to hydroxyapatite. (A) BTNP nHA binding kinetics. Nile Red-loaded BTNPs were incubated with nHA and percent BTNPs bound to nHA was measured by loss in Nile Red fluorescence in the supernatant over time. (B) Chemical mapping in STEM-EDS enables visualization of 10% Aln BTNPs physically bound to nHA using sulfur (blue) as a chemical signature for BTNPs and calcium (white) as signature for nHA. 0% Aln formulation demonstrates minimal nHA binding. Scale bar: 60 nm.
Figure 8B:
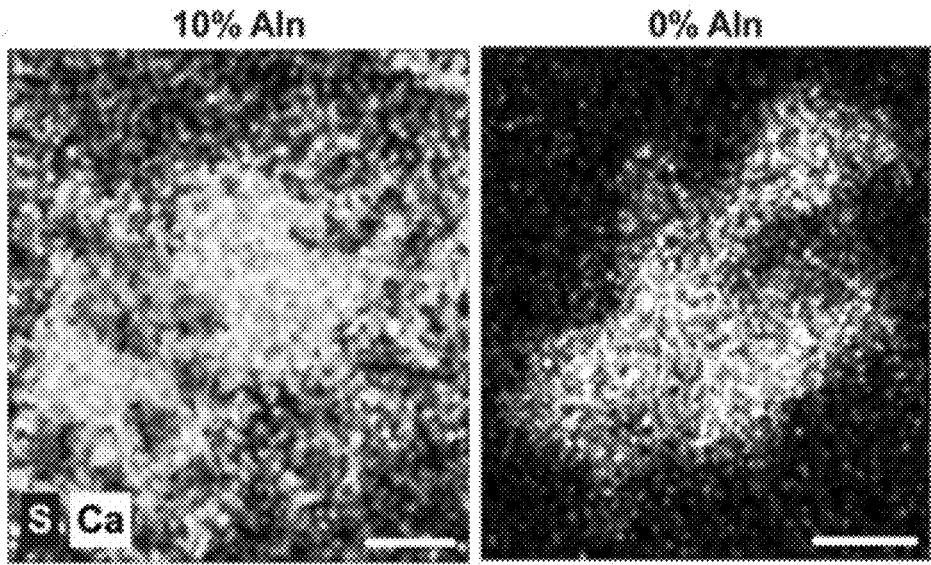
Figure 9:
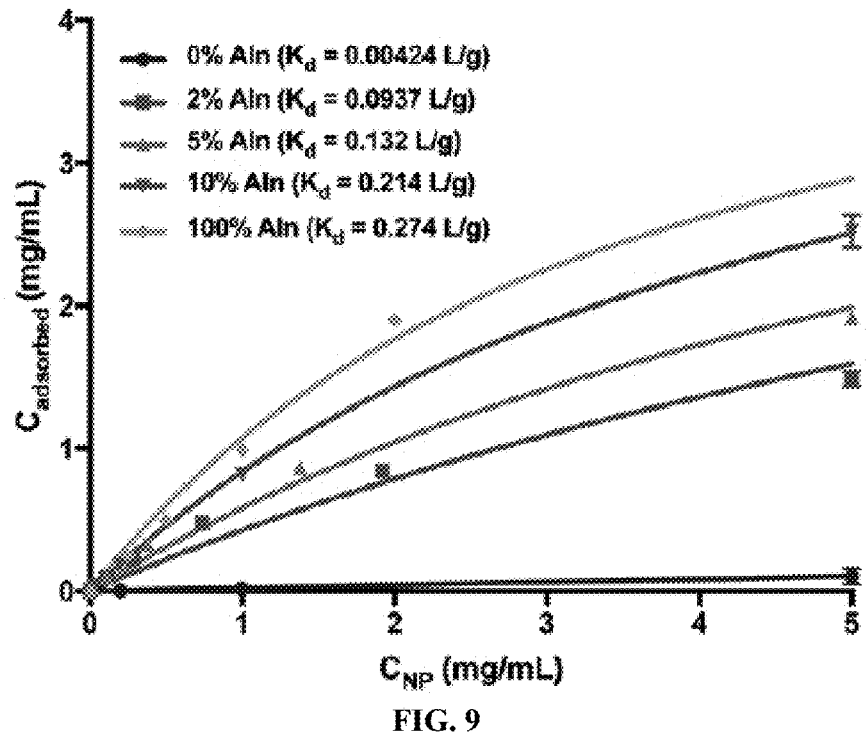
FIG. 9 shows a graph illustrating BTNP adsorption isotherm. Nile Red-loaded BTNPs were incubated with nanocrystalline HA at varying concentrations. BTNP concentration bound to HA was measured by loss in Nile Red fluorescence in the supernatant after 24 hr and calculated from a standard curve.
Figure 10A:
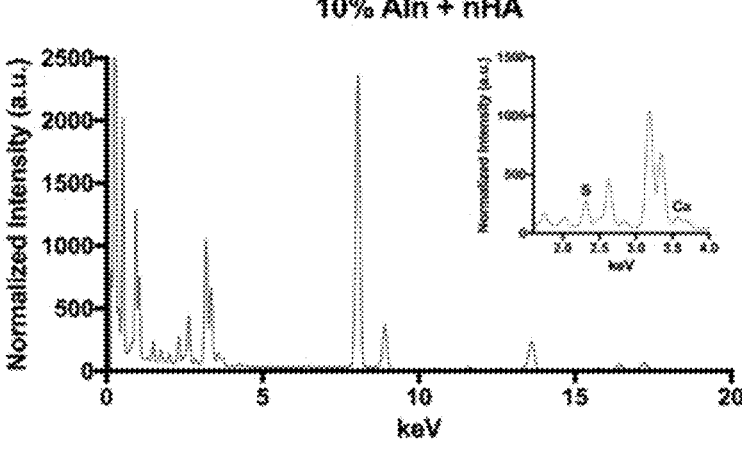
FIGS. 10A-B show graphs and images illustrating STEM-EDS characterization of in vitro nHA binding of BTNPs. (A) 10% Aln formulation EDS spectra. (B) 0% Aln formulation EDS spectra. Only the 10% Aln formulation of (A) exhibits significant sulfur peak (inset images). Original HAADF images from which EDS spectra was analyzed on right. Scale bar: 50 nm.
Figure 10A:
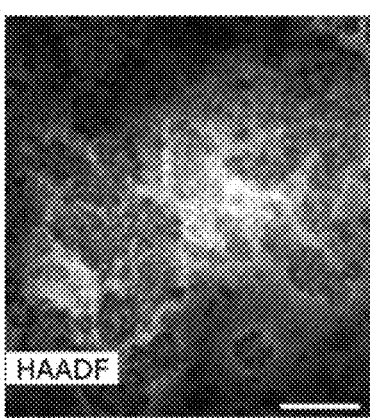
Figure 10B:
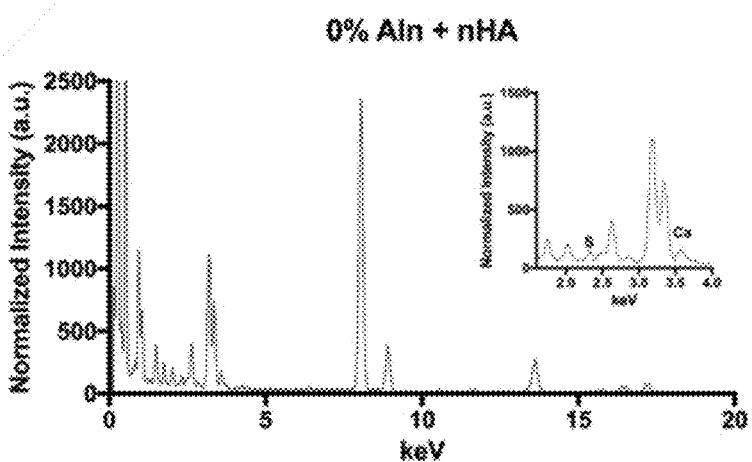
Figure 10B:
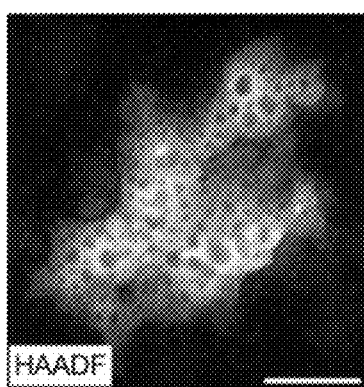
Figure 11:
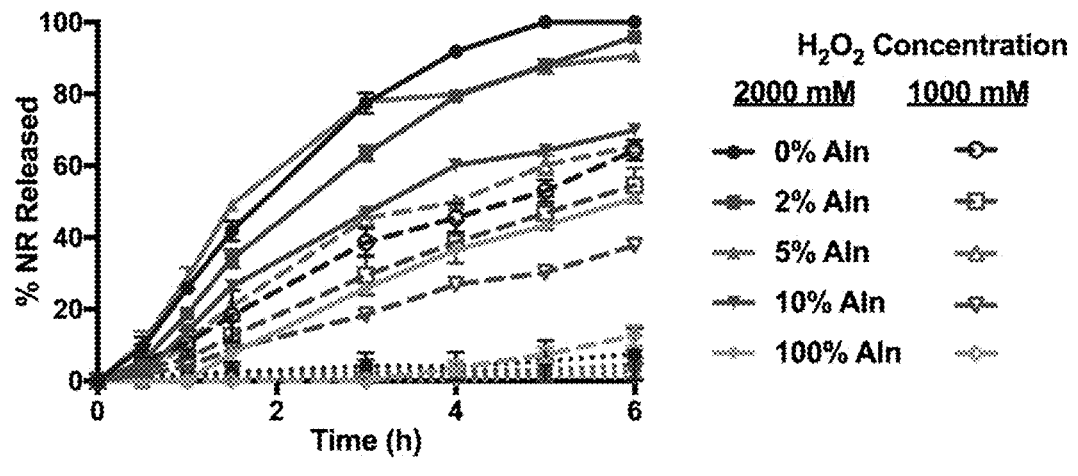
FIG. 11 shows a graph illustrating GANT58-BTNP ROS-mediated release characterization. $H_2O_2$ concentration-dependent release of encapsulated species from BTNPs as measured by Nile Red method.

Bone Targeting and Release Characterization of BTNPs. The bone-binding kinetics of the BTNPs were assessed in vitro using nanocrystalline hydroxyapatite (nHA) as a bone substitute. An Aln-dependent binding of BTNPs to nHA was observed, with increasing Aln content leading to higher equilibrium nHA binding (FIG. 8A). Notably, at these conditions, the 10% Aln formulation exhibited similar binding kinetics to the 100% Aln formulation. Adsorption isotherm experiments also demonstrated a similar trend with increasing Aln content leading to greater binding affinity (FIG. 9). This finding, along with the results from the combinatorial NP library and the stability studies, supported the use of the 10% Aln BTNP formulation as the lead candidate for subsequent in vivo studies. After incubation with nHA, 10% Aln and 0% Aln formulations were further investigated for nHA affinity using chemical mapping in EDS-STEM. Sulfur (blue, indicative of PPS) and calcium (white) were used as the chemical signatures for BTNPs and nHA respectively. 10% Aln BTNPs exhibited significant binding to nHA whereas the 0% Aln BTNPs showed no specificity or binding to nHA (FIGS. 8B and 10A-B). The ROS-sensitive behavior of the BTNPs was investigated in vitro using $H_2O_2$ as the representative ROS species and Nile Red (NR)-loaded BTNPs. The NR cargo was released in an $H_2O_2$ concentration-dependent manner with minimal cargo release at low $H_2O_2$ concentrations (FIG. 11). After micelle disassembly in vivo through oxidation, it is hypothesized that the hydrophilic polymers will be small enough for renal clearance as proposed for other PPS-based polymer systems.

BTNP Pharmacokinetics. The PK profile of each GANT58-BTNP formulation was determined by measuring the circulation half-life of fluorescently-labeled BTNPs. After retroorbital injection of Cy5-labeled GANT58-BTNPs (GANT58-Cy5BTNPs), a tail nick method was used to obtain small amounts (<5 μL) of blood immediately post-injection (t=0) and at subsequent times up to 24 h. The blood samples were then measured for Cy5 fluorescence intensity using a fluorescence plate reader. BTNP concentration was then calculated from a standard curve. Circulation time of GANT58-BTNPs was shown to be Aln content-dependent, with higher Aln content leading to shorter circulation half-lives and lower systemic bioavailability (FIGS. 12A-B, Table 2). As expected and in line with other literature, highly negative BTNP surface charge increased clearance and consequently reduced circulation time and bioavailability.

TABLE 2

| | Pharmacokinetic Parameters of GANT58-BTNPs | | | |
| --- | --- | --- | --- | --- |
| | $T_{1/2, fast}$ (hr) | $T_{1/2, slow}$ (hr) | $K_E$ (hr) | Cl (μg-hr/mL) |
| 0% Aln | 0.093 | 9.827 | 0.071 | 0.668 |
| 2% Aln | 0.184 | 7.582 | 0.091 | 0.814 |
| 5% Aln | 0.164 | 4.395 | 0.158 | 1.012 |

TABLE 2-continued

Pharmacokinetic Parameters of GANT58-BTNPs

| | $T_{1/2, fast}$ (hr) | $T_{1/2, slow}$ (hr) | $K_E$ (hr) | Cl (μg-hr/mL) |
|---|---|---|---|---|
| 10% Aln | 0.2264 | 2.539 | 0.273 | 1.080 |
| 100% Aln | 0.328 | 2.113 | 0.328 | 4.435 |

$T_{1/2}$ = half life;
$K_E$ = elimination rate constant;
Cl = clearance

Figure 12D:
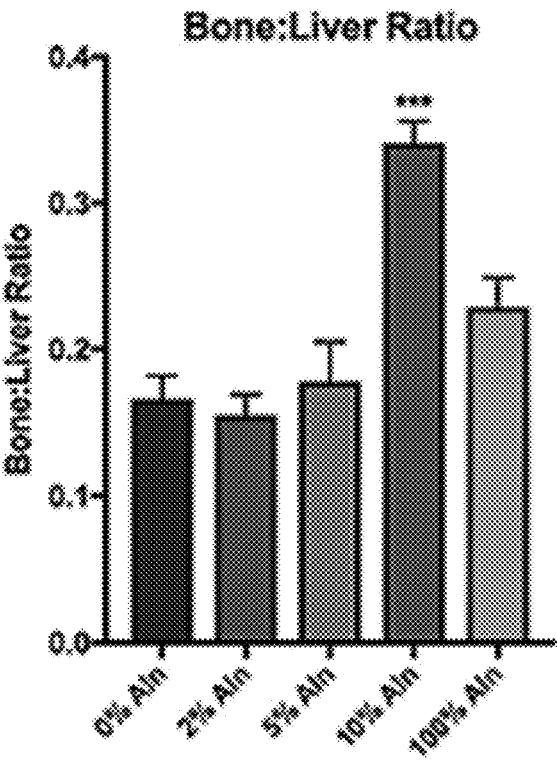

BTNP Biodistribution. The biodistribution of GANT58-Cy5BTNPs was next evaluated following intravenous (i.v.) tail vein injection in non-tumor bearing CD-1 mice. After 24 h, mice were sacrificed and long bones (forelimbs and hindlimbs) and organs were imaged using an IVIS imaging system. IVIS imaging analysis software was used to quantify Cy5 fluorescence intensity in the long bones (FIG. 12C). In vivo GANT58-Cy5BTNP fluorescence in the hindlimbs and forelimbs was also found to be Aln content-dependent, with higher Aln content leading to higher Cy5 signal in bone, as expected based on in vitro experiments. Further, Cy5 fluorescence intensity in the forelimbs and hindlimbs was >2-fold higher in mice treated with the 10% and 100% Aln formulation over the 0% Aln formulation. Quantification of bone:liver ratios demonstrate that 10% Aln has significantly higher bone:liver ratio than all other formulations (FIG. 12D). Despite the high bone uptake exhibited by the 100% Aln formulation, the 10% Aln formulation was deemed the lead candidate for subsequent studies due to its superior GANT58 drug loading (4-fold higher, FIG. 5C), high cargo retention exhibited by FRET studies (FIG. 6D), and a smaller, more desirable size for systemic delivery compared to the 100% Aln formulation (100 nm vs 210 nm, respectively), and its higher bone:liver biodistrubution ratio.

Figure 13:
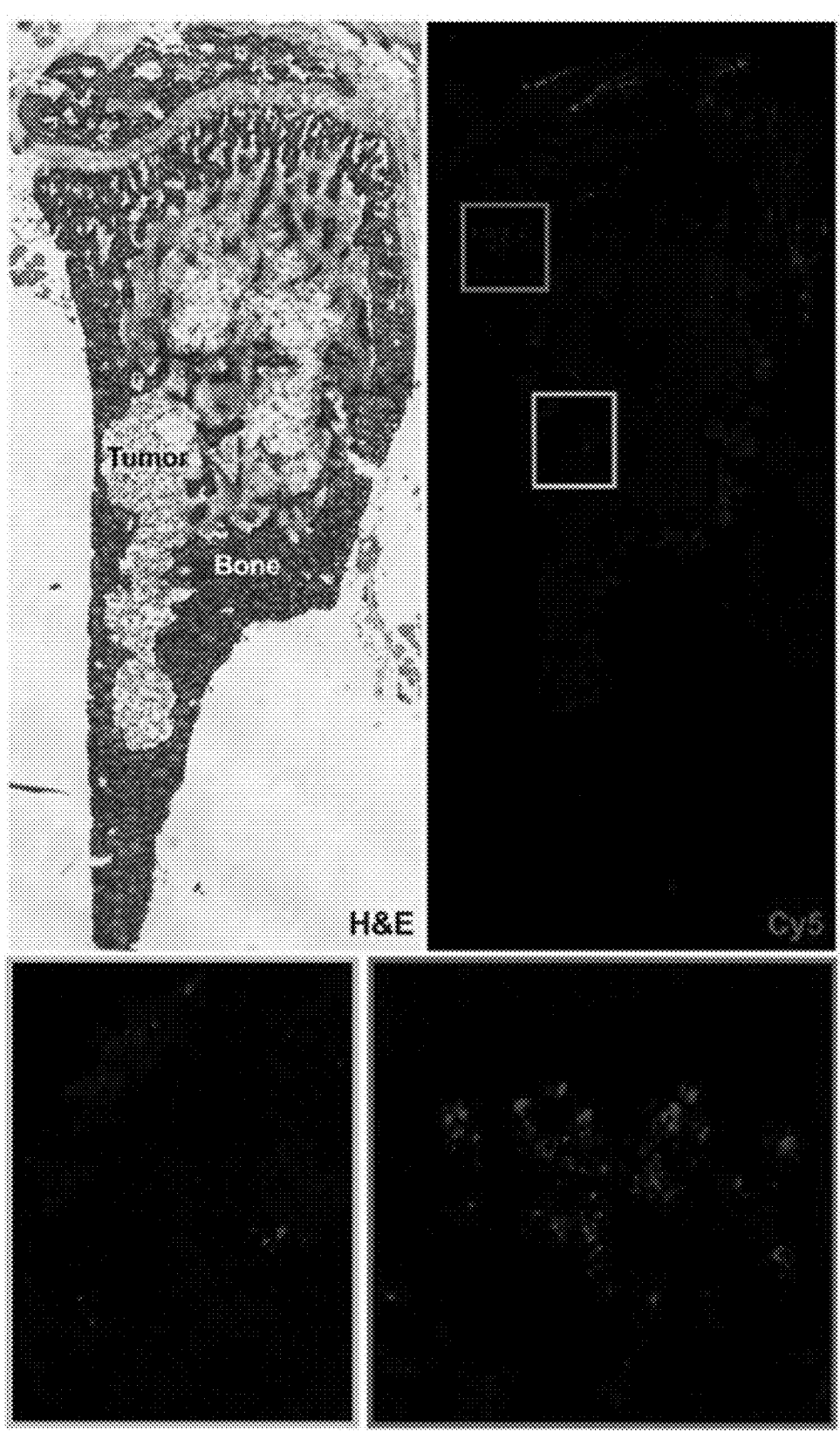
FIG. 13 shows images illustrating BTNP cryohistology and spatial distribution. BTNPs distribute to tumor-bearing tibia after single i.v. injection. BTNPs localize to the trabecular space (magenta zoomed image) as well as into the tumor space (cyan zoomed image) in addition to the endosteal and periosteal bone surface. H&E staining was performed on serial section for reference.

Next, visualization of the 10% Aln BTNPs in tumor-bearing mouse tibiae was pursued in order to investigate spatial distribution of the BTNPs within the bone-tumor milieu. MDA-MB-231-bone cells were intratibially injected into mice and allowed 14 days for growth. A single injection of Cy5BTNPs were then administered via tail vein injection and allowed 24 h for circulation prior to sacrifice and hindlimb dissection. After cryosectioning, serial sections were stained with hematoxylin and eosin (H&E) or imaged via fluorescence microscopy for Cy5 fluorescence. Fluorescence microscopy showed there was significant Cy5BTNP signal in the tibia after 24 h circulation, and comparison to the H&E section showed the Cy5BTNPs localized both at the endosteal surface and in the trabeculae, as well as in the tumor space (FIG. 13). These findings suggest the BTNPs are able to penetrate the bone matrix and the tumor and are retained there >24 hr.

Figure 12E:
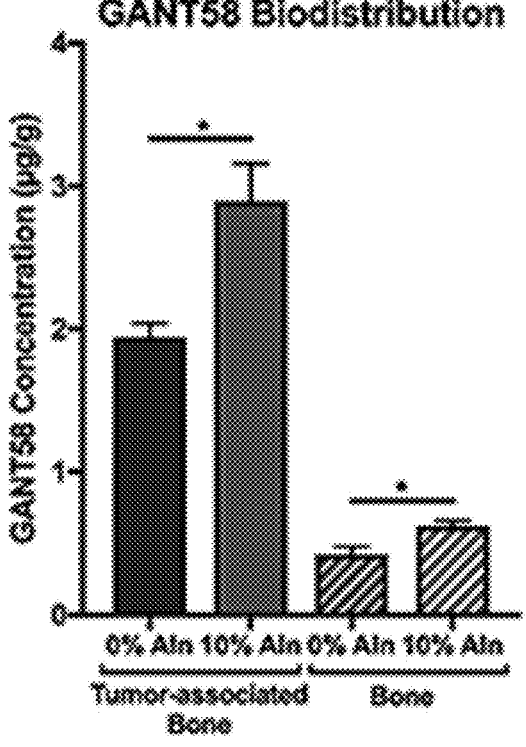

Delivery of the GANT58 cargo to bone and bone-tumor site was determined by high performance liquid chromatography (HPLC) on tissues extracted from intratibially-injected MDA-MB-231 tumor-bearing athymic nude mice that had been systemically treated with GANT58-BTNP (FIG. 12E). In mice treated with 10% Aln formulation, GANT58 concentration was approximately 50% higher in both the tumor-associated bone and the nontumor-bearing bones, indicating that Aln-based bone-targeting increases GANT58 concentration at the bone-tumor site. Further, GANT58 biodistribution to the tumor-associated bone was roughly 4-fold higher than nontumor-bearing bone in both groups, suggesting that the enhanced permeation and retention (EPR) effect contributes to tumor accumulation of nanoparticles through leaky blood vessels at the bone tumor site.

Figure 14A:
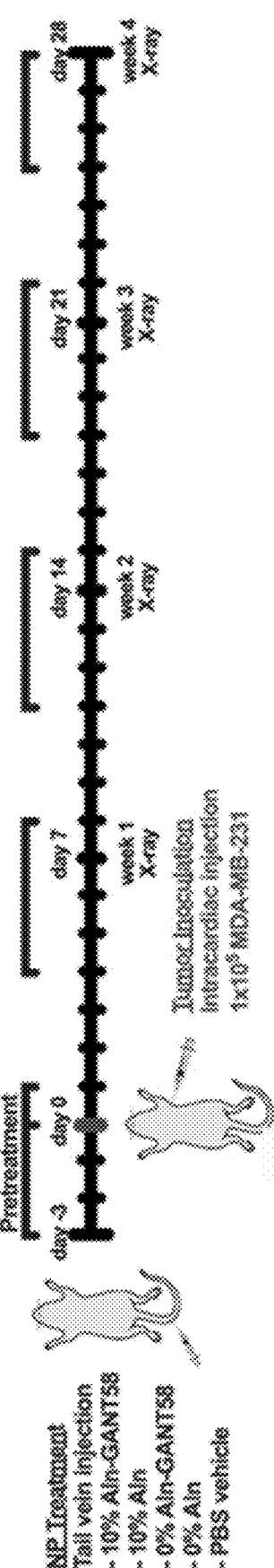
FIGS. 14A-G show images and graphs illustrating that GANT58-BTNP treatment reduces tumor-mediated bone destruction in a mouse model of bone metastasis. (A) Tumor-inoculation and treatment timeline for intracardiac model of bone metastasis. (B) Lesion area as assessed by radiographic analysis of combined hindlimbs is significantly reduced in GANT58-BTNP treated mice over control ($p<0.001$). Yellow arrow indicates osteolytic lesions. (C) μCT analysis of tibiae bone volume fraction (BV/TV) showed significantly improved bone preservation in mice treated with GANT58-BTNPs over control ($p<0.0001$). (D) Tartrate-resistant acid phosphatase (TRAP) histomorphometric analysis of osteoclast (OC) number shows significantly decreased OC number per bone perimeter in GANT58-BTNP treated mice compared to control ($p<0.001$). Yellow arrows indicate OCs. Scale bar: 100 μm. (E) PTHrP immunohistochemistry quantification shows that there is a significant decrease in tibial PTHrP protein in mice treated with GANT58-BTNP ($p<0.01$). Scale bar: 500 μm, inset image 100× magnification. (F) Spatial quantification of Ki67 immunohistochemistry shows there is a decrease in % Ki67 positive cells at the bone interface when treated with GANT58-BTNPs ($p<0.001$). Shaded and outlined regions denote bone. Scale bar: 200 μm. (G) In vitro MTS proliferation assay over 5 day period after drug treatment shows 40 μM GANT58 treatment slows tumor cell growth on rigid but not compliant substrates ($p<0.001$).

GANT58-BTNP Treatment Reduces Bone Destruction in a Mouse Intracardiac Model of Bone Metastasis. Based on the in vitro and biodistribution studies, it was hypothesized that GANT58-BTNPs could block metastatic tumor-associated bone destruction and potentially reduce initiation of bone metastasis. To test this hypothesis, female athymic nude mice were treated with either GANT58-BTNPs (10% Aln-GANT58, 8 mg/kg GANT58), unloaded BTNPs (10% Aln), non-targeted GANT58-BTNPs (0% Aln-GANT58, 8 mg/kg GANT58), non-targeted unloaded BTNPs (0% Aln), or no treatment control (Control) via tail vein injection. The inclusion of a free GANT58 arm of the study was precluded by the inability to identify an intravenously-tolerable vehicle capable of solubilizing the lipophilic GANT58. MDA-MB-231-bone cells were inoculated via intracardiac injection, and treatments were given 5 times/week for 4 weeks (FIG. 14A).

Figure 14B:
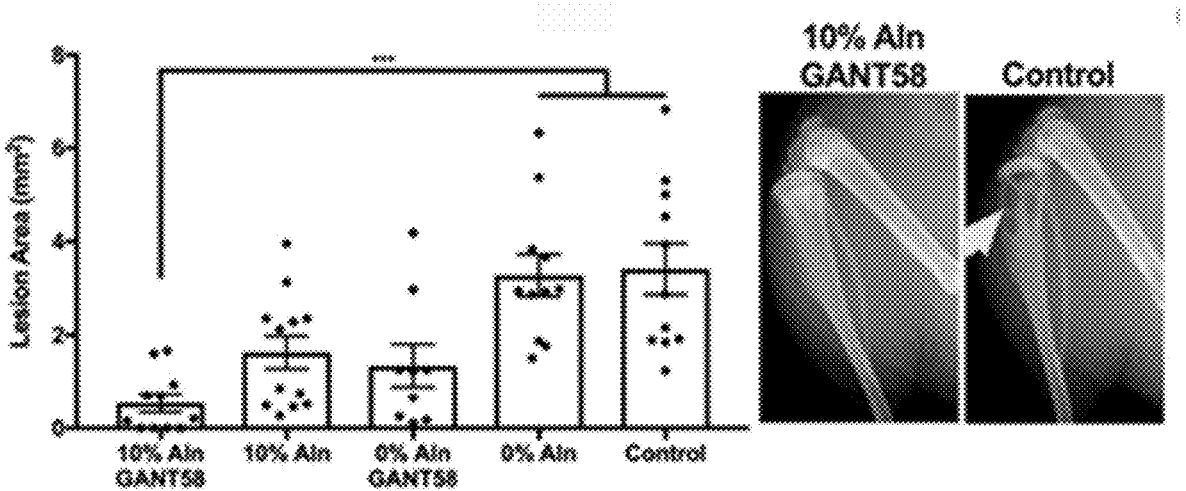
Figure 14C:
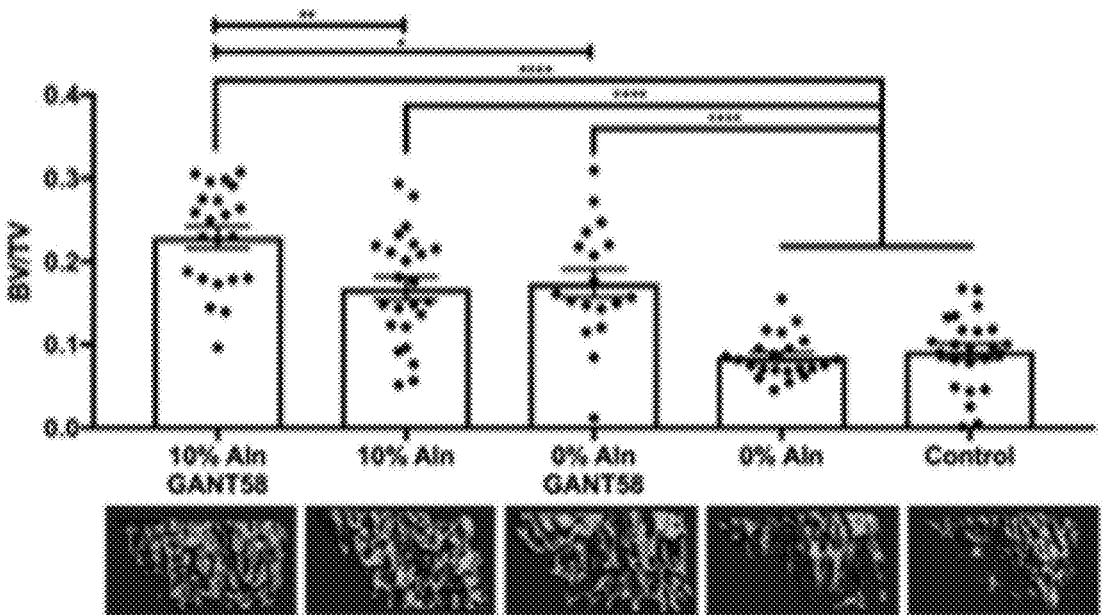
Figure 14D:
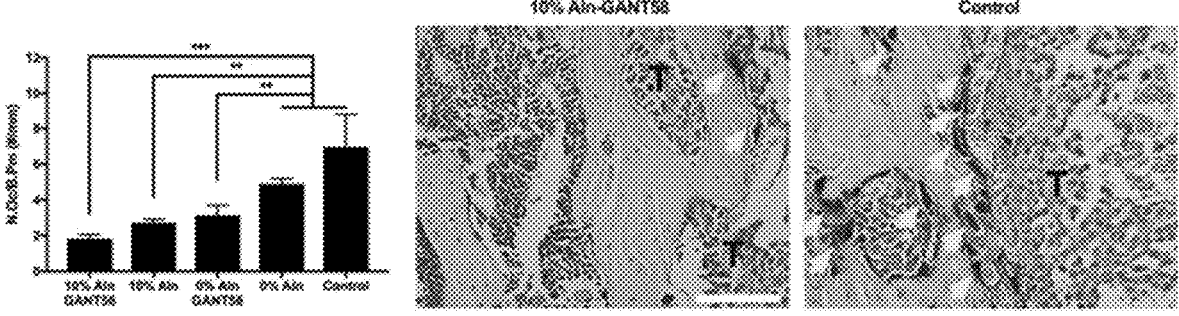
Figure 15:
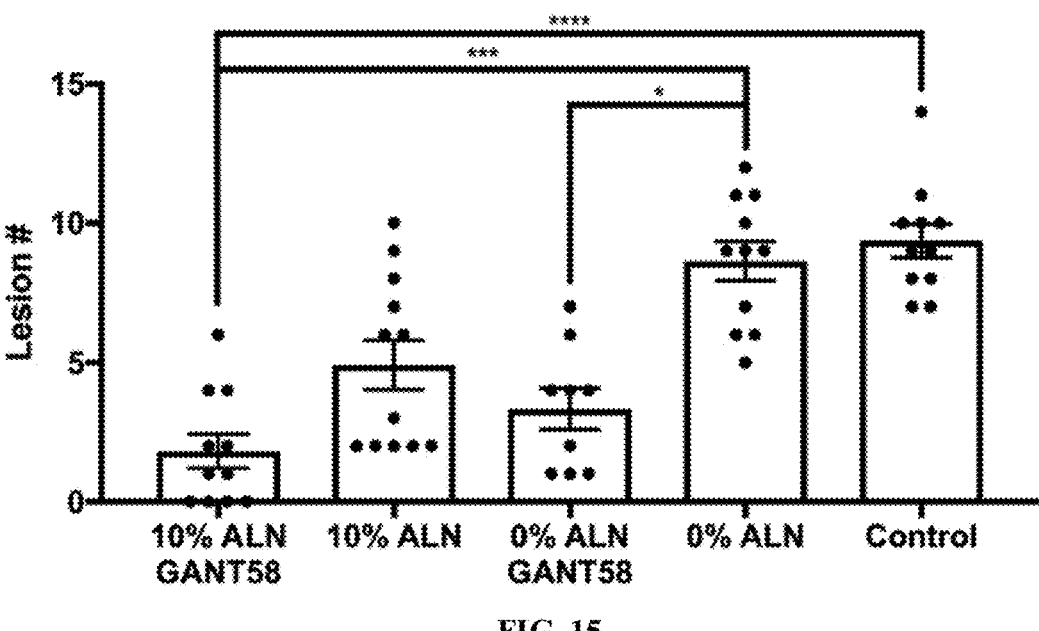
FIG. 15 shows a graph illustrating that GANT58-BTNPs reduced osteolytic lesion number in mouse model of early bone metastasis. Radiographic analysis at 4 weeks post-tumor inoculation indicates mice treated with GANT58-BTNPs have significantly reduced number of osteolytic lesions.
Figure 16A:
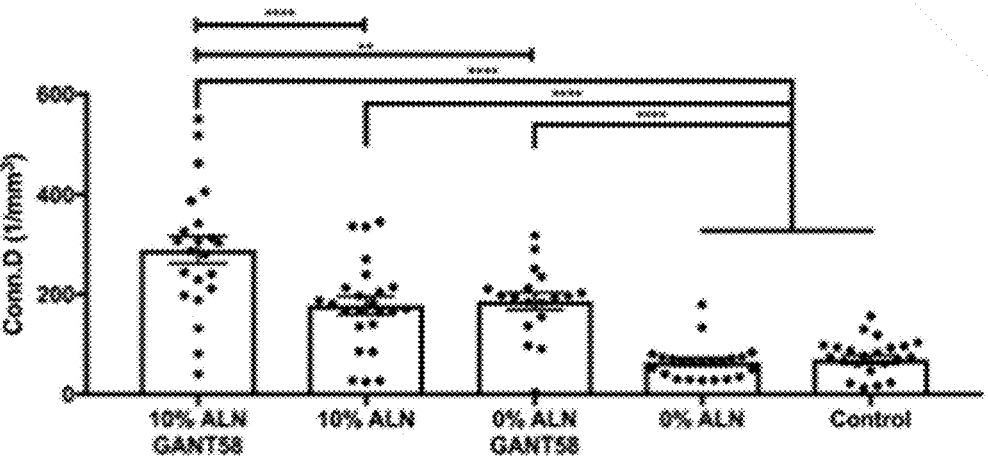
FIGS. 16A-D show graphs illustrating that GANT58-BTNPs reduced bone destruction in mouse model of early bone metastasis. (A-D) Ex vivo μCT analysis at 4 weeks post-tumor inoculation indicates mice treated with GANT58-BTNPs have (A) significantly increased connectivity density (Conn.D), (B) trabecular number (Tb.N), (C) trabecular thickness (Tb.Th), and (D) significantly decreased trabecular spacing (Tb.Sp).
Figure 16B:
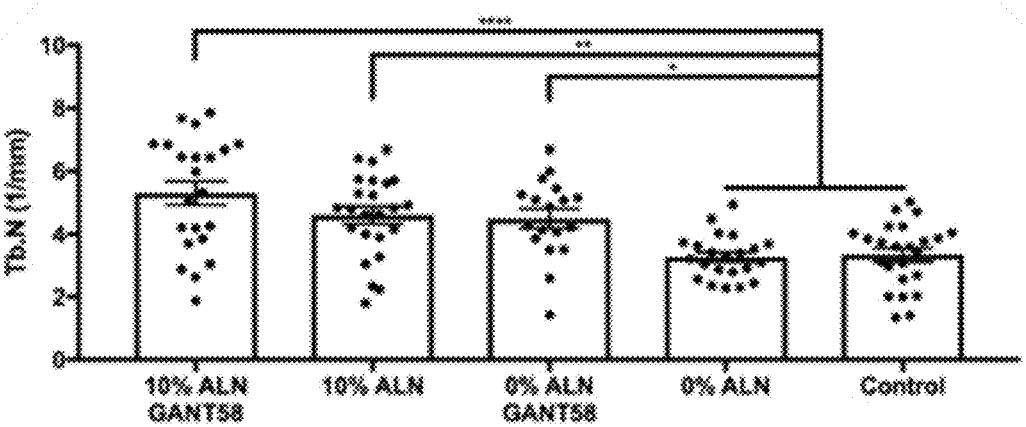
Figures 16C, 16D:
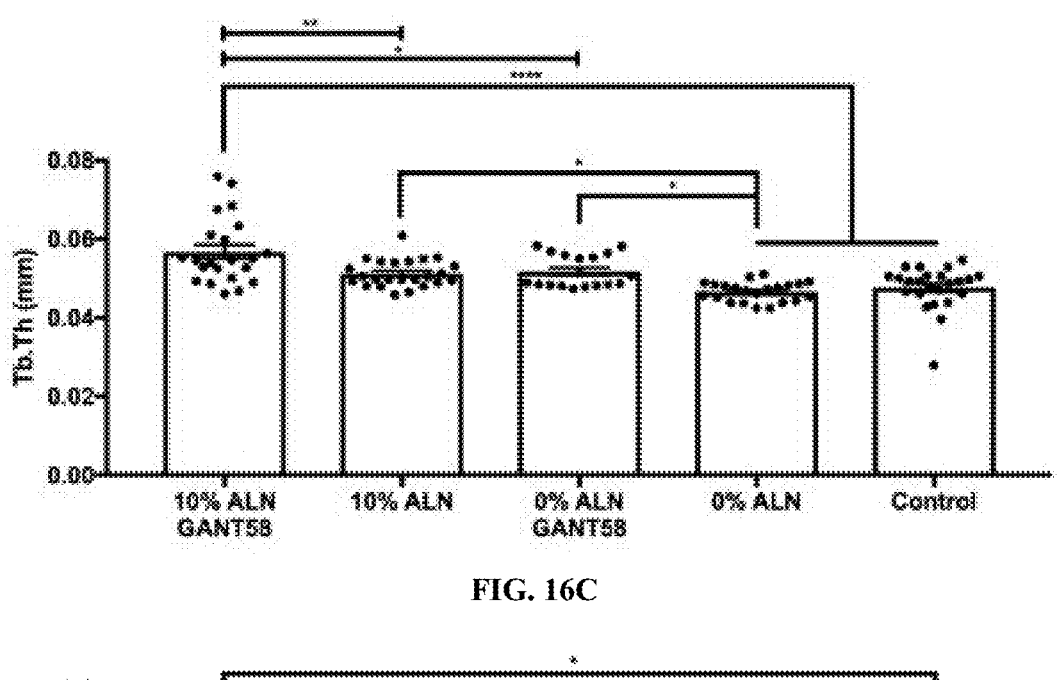
Figure 17A:
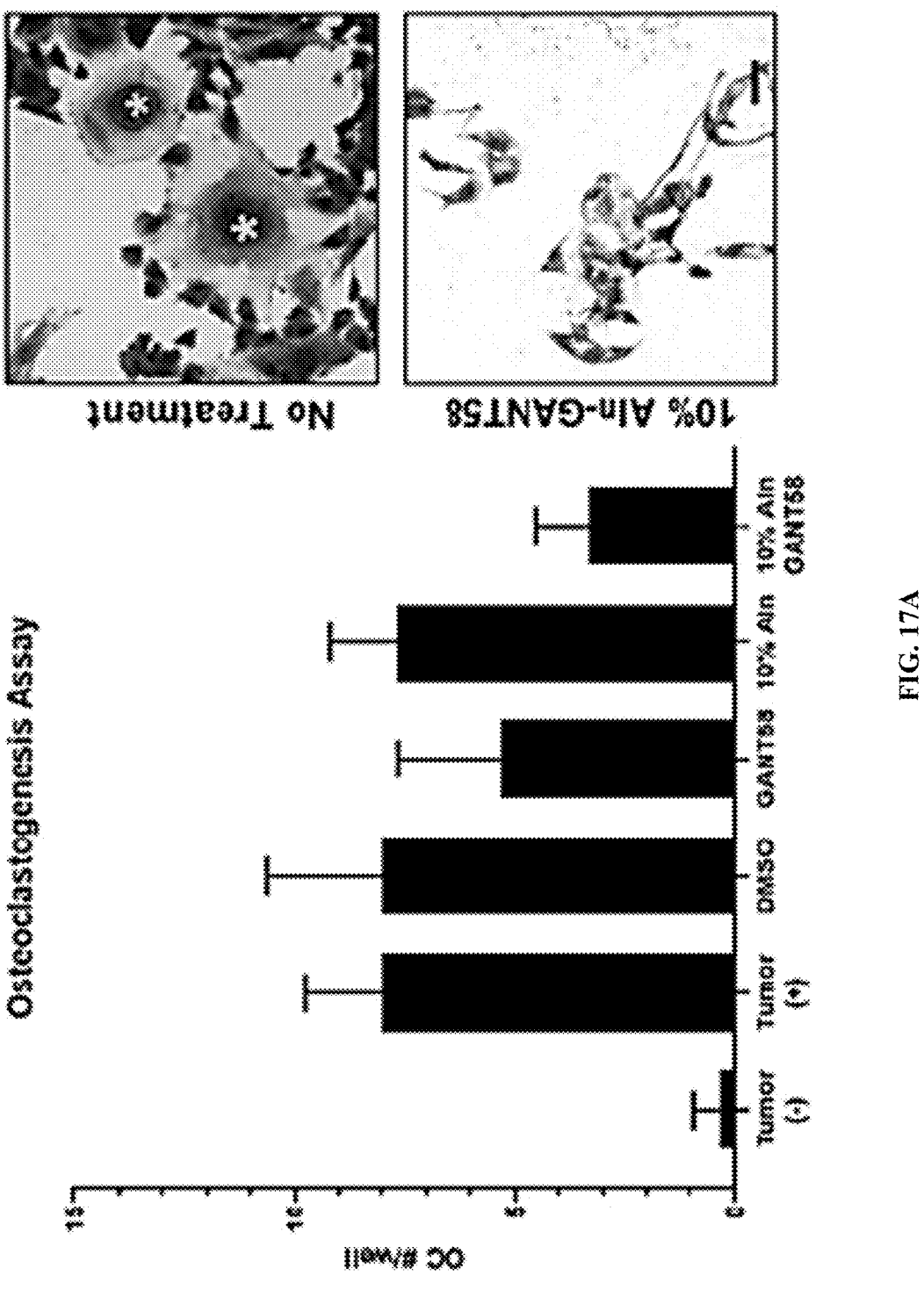
FIGS. 17A-B show graphs and images illustrating GANT58-BTNP effect on bone cells. (A) Number of osteoclasts (OC)/well in coculture treated with GANT58, BTNP, and GANT58-BTNP after 6 days culture of mouse bone marrow-derived stromal cells with MDA-MB-231 cells. Scale bar: 25 μm (B) Alizarin Red mineralization assay. hMSCs were treated with GANT58-BTNPs and cultured for 14 days in osteogenic media. Mineralization was observed by Alizarin Red stain and measured by dye extraction and reading absorbance at 405 nm. Scale bar: 100 μm.

Radiographic imaging was used to track tumor progression in the hindlimbs of mice by visualization of osteolytic lesions. Radiographic analysis prior to sacrifice at week 4 showed that the 10% Aln-GANT58 treated mice exhibited smaller and fewer lesions compared to the 0% Aln treated and control mice (FIGS. 14B and 15). To further assess the bone quality in these mice, micro-computed tomography (μCT) was conducted on the tibiae after sacrifice (FIG. 14C). Mice treated with 10% Aln-GANT58, 10% Aln, and 0% Aln-GANT58 had significantly higher bone volume fraction (BV/TV) than the 0% Aln and control mice. These findings demonstrate that the 10% Aln BTNPs alone have a therapeutic effect due to functionalization with the osteoclast-inhibiting bisphosphonate, Aln. This finding aligns with previous studies that have also found that polymer-conjugated Aln exhibits antiresorptive activity in vivo. Notably, the 10% Aln-GANT58 treated mice exhibited significantly higher BV/TV than 10% Aln and 0% Aln-GANT58 treated mice, suggesting that the GANT58 and Aln collaborate to produce better bone outcomes in the setting of TIBD. Measurement of other morphometric parameters including connectivity density (Conn.D), trabecular number (Tb.N), trabecular separation (Tb.Sp), and trabecular thickness (Tb.Th) also demonstrated that 10% Aln-GANT58 treatment significantly improved bone quality (FIGS. 16A-D). The functional effect of both GANT58 and Aln treatment is to reduce osteoclastogenesis. To confirm that improved bone outcomes with GANT58-BTNP treatment is due to a reduction in osteoclast activation, tartrate-resistant acid phosphatase (TRAP) histological staining was conducted on the tibia samples after μCT analysis (FIG. 14D). TRAP staining showed that the 10% Aln-GANT58, 10% Aln, and 0% Aln-GANT58 treated mice exhibited significantly fewer osteoclasts per bone perimeter (N.Oc/B.Pm) than 0% Aln-treated and control mice, with 10% Aln-GANT58 trending toward having the least osteoclasts of any group. The effect of BTNPs on bone cell precursors was next investigated in vitro in order to substantiate the in vivo study mechanistic finding that GANT58-BTNPs reduce tumor-mediated osteoclastogenesis. First, a coculture of mouse bone marrow-derived stromal cells and MDA-MB-231 tumor cells was utilized as a means to measure the GANT58-BTNP effect on osteoclastogenesis. The coculture was treated with 40 μM free GANT58, BTNPs, or GANT58-BTNPs and cultured for 7 days prior to fixation and tartrate-resistant acid phosphatase (TRAP) staining. Results showed that GANT58-BTNP treatment significantly reduced osteoclast number compared to the no treatment control (FIG. 17A). These results suggest that GANT58-BTNPs exhibit the hypothesized effect of reducing tumor-mediated osteoclastogenesis.

Figure 14E:
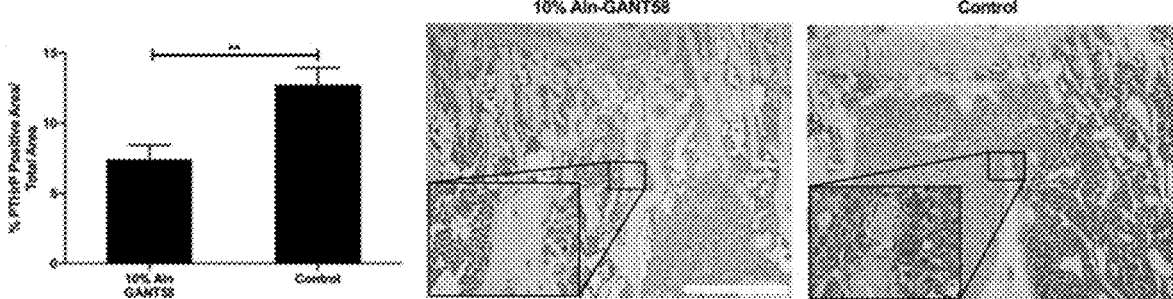

Previous mechanistic studies have demonstrated that genetic repression of Gli2 transcription factor activity reduces expression of PTHrP and that this is the mechanism that consequently reduces tumor-associated osteoclastogenesis. To confirm that this mechanism is operative in the context of GANT58-BTNP treatment, PTHrP immunohistochemistry was carried out as a marker for GANT58-mediated Gli2 inhibition. Quantitation showed that GANT58-BTNP treatment significantly reduced PTHrP protein levels at the bone tumor site compared to control, suggesting that the reduction in osteoclast number is tied to reduced PTHrP signaling (FIG. 14E).

Figure 14F:
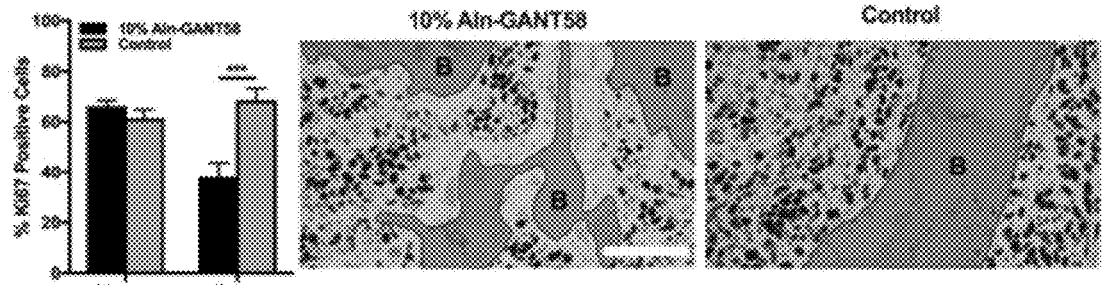
Figure 14G:
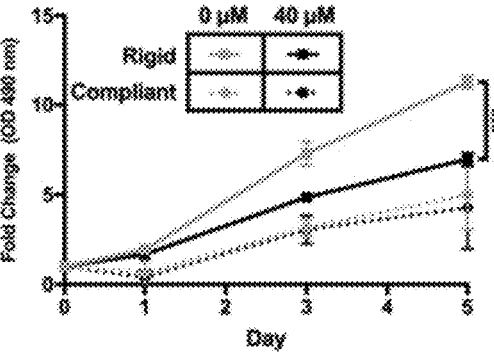
Figure 18A:
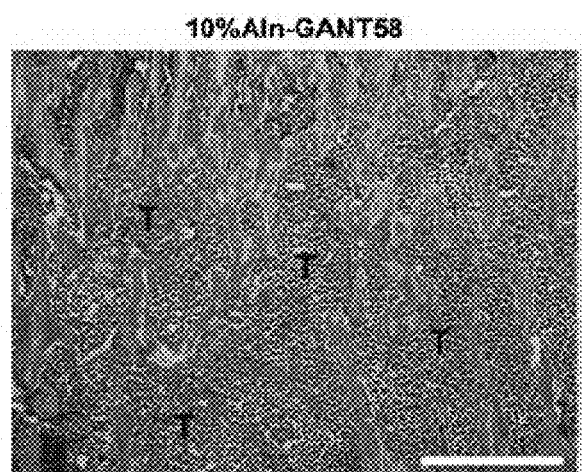
FIGS. 18A-C show graphs and images illustrating that GANT58-BTNPs treatment does not affect overall tumor burden but reduces bone destruction as measured by histomorphometric analysis in mouse model of early bone metastasis. (A) Hematoxylin and Eosin (H&E) stain. (B-C) H&E histomorphometry demonstrates there is no significant change in (B) overall tumor burden but a significant improvement in (C) bone area in GANT58-BTNP treated mice over control. Scale bar: 500 μm.
Figure 18A:
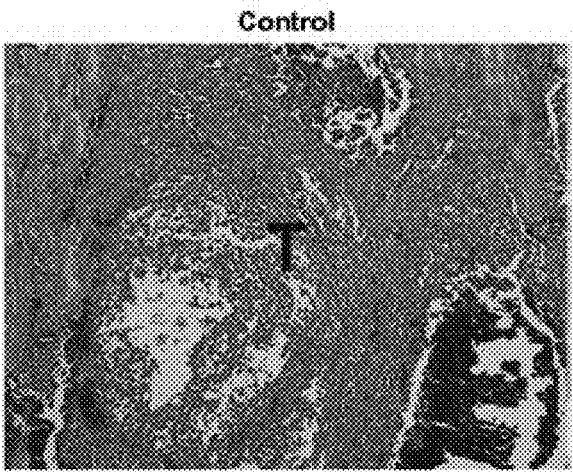
Figure 18B:
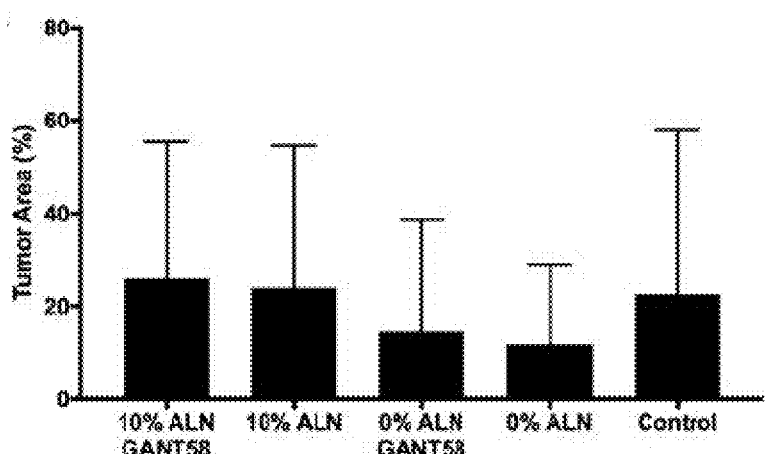
Figure 18C:
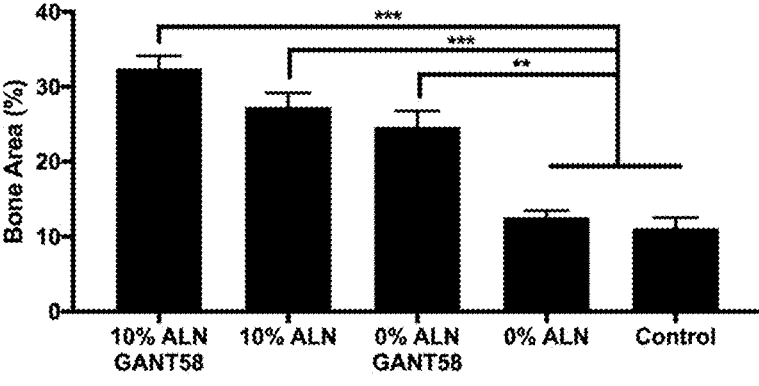

Previous studies showed that Gli2 overexpression accelerates cell cycle progression and augments proliferation in tumor cells, while Gli2 inhibition blocks tumor growth in vitro and even in vivo when Gli2 is molecularly repressed using genetic techniques in bone metastatic cancer cells lines. This motivated the hypothesis that blocking Gli-activity in metastatic breast tumors could obstruct their potential to establish in bone and adopt a bone-destructive phenotype. However, histomorphometric analysis of the tibiae from treated mice (FIGS. 18A-C) showed no significant decrease in overall tumor burden in 10% Aln-GANT58 treated mice (FIG. 18B). It is important to note the large variability in tumor burden inherent to the intracardiac model as evidenced by the large standard error. Even with this variability in consideration, there is significant tumor burden in the 10% Aln-GANT58 treated mice despite maintenance of high bone area (FIG. 18C). Based on the present inventors' previous studies reporting that both rigid mineralized bone matrix and TGF-$\beta$ drive Gli2 expression in bone-metastatic cancer cell lines, it was hypothesized that GANT58-BTNP treatment may have a spatially heterogeneous effect on tumor cells that mirrors the spatial variation in Gli2 expression. Therefore, the effect of GANT58-BTNP treatment on tumor cell proliferation was measured by measuring Ki67 via IHC (FIG. 14F). Importantly, heterogeneous changes were found in Ki67 staining, with a reduction of Ki67 positive cells near the bone-tumor interface and more staining away from the bone in the 10% Aln-GANT58 treated mice, but not in untreated control mice. To further investigate these findings, an in vitro proliferation assay was conducted on MDA-MB-231 cells cultured on rigid, tissue culture plastic or compliant gelatin methacrylate (GelMA) gels treated with GANT58 (FIG. 14G). The proliferation assay supported the in vivo findings showing that GANT58 significantly reduced proliferation of cells on rigid substrates, but not on compliant substrates. Taken together, these findings support the concept that concentrated bone surface delivery of the GANT58-BTNP strongly blocks both aberrant osteoclast activation and tumor cell in-growth into the mineralized phase of tumor-containing bone.

Cells respond differently based on the mechanical rigidity of their microenvironment. Mechanically-sensitive responses in tumor drive phenotypic changes that alter gene expression and cell behavior causing spatial heterogeneity within the tumor site, especially for a tumor microenvironment that contains both a rigid, mineralized bone phase and soft bone marrow. The present inventors' previous research demonstrated that Gli2 expression in bone metastatic cell lines is driven by matrix rigidity, and here it is shown that Gli2 inhibition has direct tumor cell growth inhibition effects at the mineralized bone interface. Collectively, these findings suggest that GANT58-BTNP effectively protects against TIBD by inhibiting the positive feedback signaling between tumor and bone cells, consequently reducing osteoclast activity, and reducing the stimulation for tumor cells to grow into the mineralized phase of the bone.

Figure 17B:
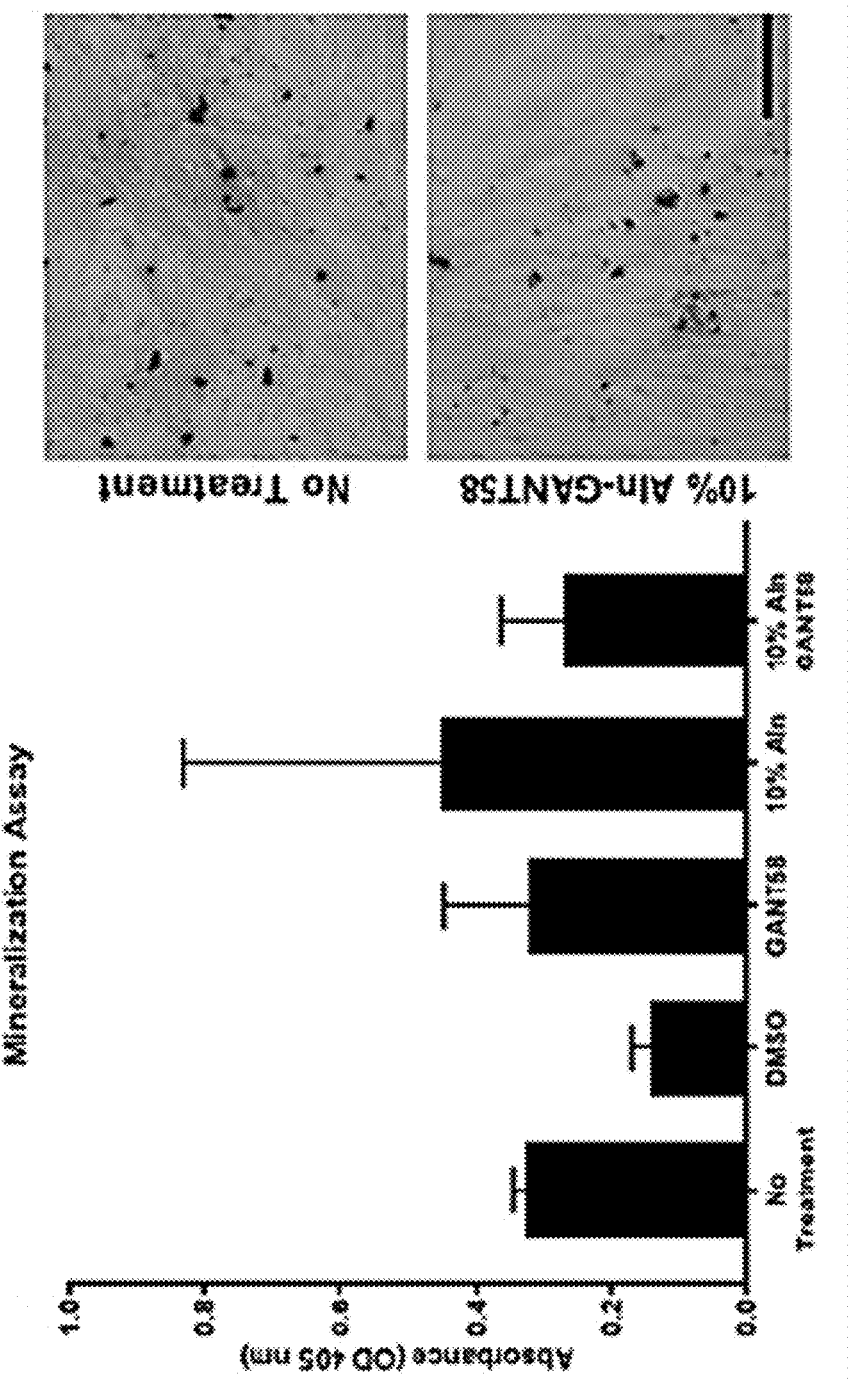
Figure 19A:
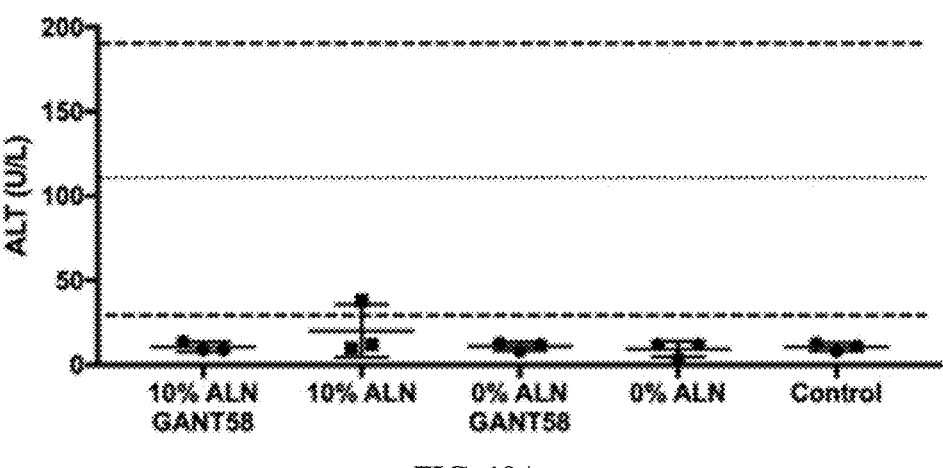
FIGS. 19A-D show graphs and images illustrating that GANT58-BTNPs elicit minimal systemic toxicity. (A-C) Biochemical analysis of serum markers of liver toxicity (A) ALT and (B) AST, and kidney toxicity (C) BUN after 10% Aln-GANT58, 10% Aln, 0% Aln-GANT58, 0% Aln, or PBS vehicle treatment 5×/week for 4 weeks. (D) Representative images of liver and kidney at 20× and 40× from lead candidate formulation-treated (10% Aln-GANT58) and control mice.
Figure 19B:
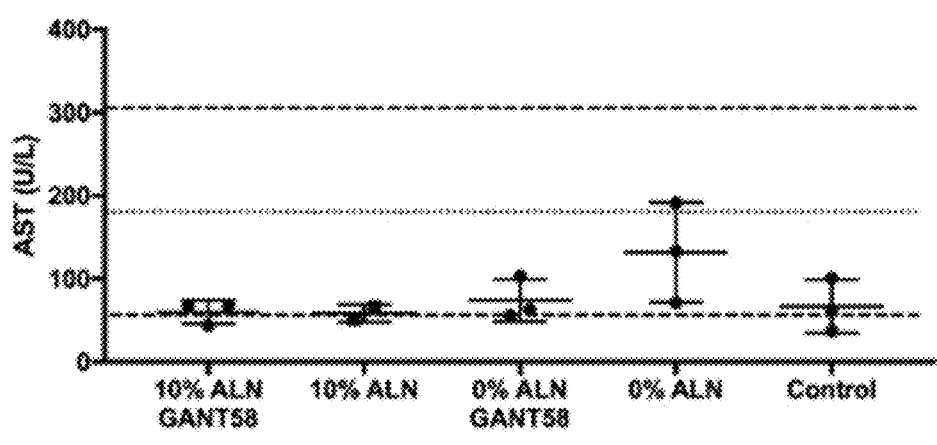
Figure 19C:
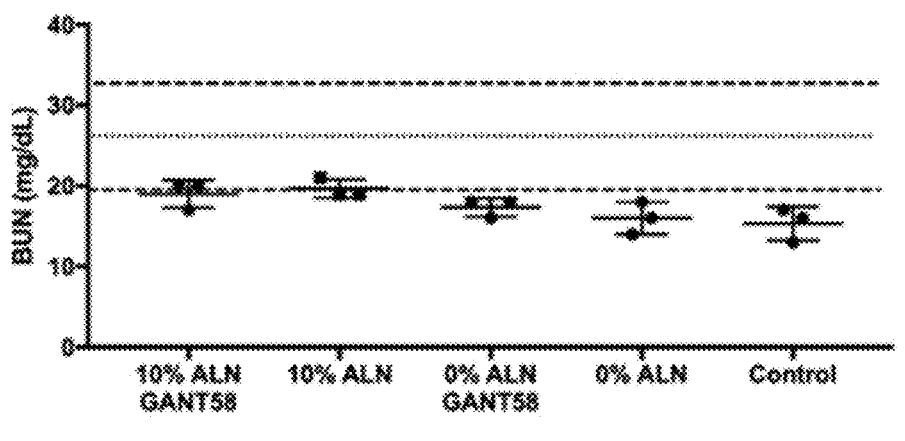
Figure 19D:
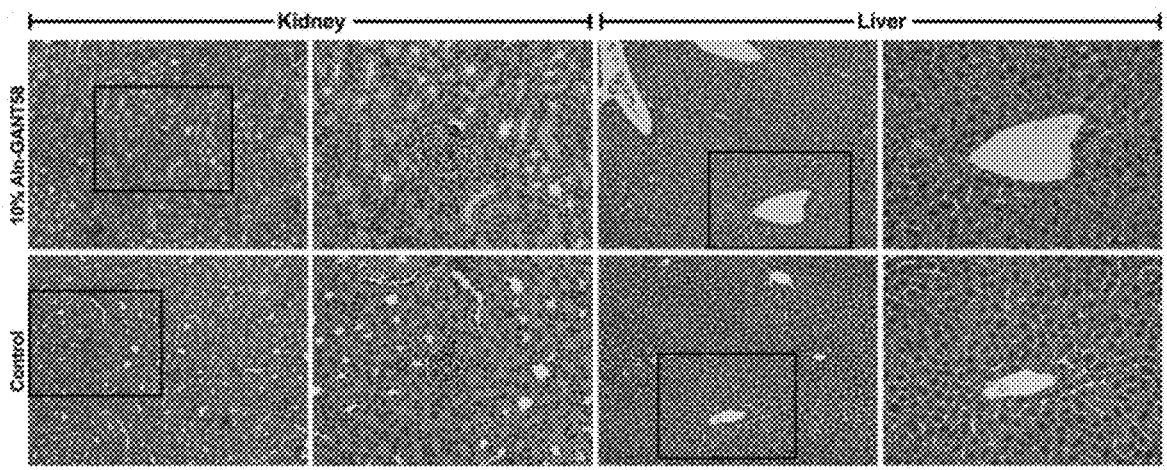

Toxicological safety of the GANT58-BTNPs after treatment at therapeutic doses is key to clinical translatability. The toxicological profile of the GANT58-BTNPs was examined by drawing blood at time of sacrifice for the cohort of mice in the intracardiac model study after having received 10% Aln-GANT58, 10% Aln, 0% Aln-GANT58, 0% Aln treatment or no treatment control daily at 8 mg/kg GANT58 (or equivalent dose of unloaded-BTNPs) for 4 weeks. Biochemical analysis of blood serum markers for liver (ALT and AST) and kidney (BUN) toxicity showed there was no significant increase above two standard deviations from average levels reported by the animal supplier (Envigo) (FIGS. 19A-C). Further, histological sections showed no evident toxicity in the liver and kidneys of lead candidate formulation-treated mice compared to control (FIG. 19D). These findings are consistent with previous studies using PPS-based polymers that have demonstrated toxicological safety even at high NP doses and in non-human primates. In addition to systemic toxicity, it is also important that GANT58-BTNPs do not affect normal osteoblastogenesis. To test this, hMSCs were treated with 40 $\mu$M free GANT58, BTNPs, or GANT58-BTNPs, and the effect of hMSC differentiation toward osteoblasts was tested using an Alizarin Red mineralization assay. After 14 days culture in osteogenic media, Alizarin Red staining showed that the GANT58-BTNP and control treatments had no negative effect on hMSC differentiation and mineralization (FIG. 17B).

The current clinical TIBD treatments—bisphosphonates and the RANKL inhibitor denosumab—have been linked to side effects such as osteonecrosis of the jaw (ONJ) and atypical femoral fractures. Thus, alternative treatments that mitigate off-targets effects are warranted. The low systemic toxicity elicited by GANT58-BTNPs in addition to its efficacy and specificity in inhibiting tumor-induced bone destruction and tumor proliferation at the bone interface highlights the potential benefit of this treatment over gold standard treatments.

CONCLUSION

Synthesis of BTNP polymers and development of a combinatorial NP library yielded a GANT58-loaded lead candidate formulation that significantly reduced bone destruction in an intracardiac mouse model of bone metastasis. The lead candidate 10% Aln formulation BTNPs demonstrated an ideal balance of systemic bioavailability, tumor biodistribution, and bone binding affinity. While conferring bone-binding affinity to nanoparticles is an area of active research, much of this work focuses on delivery of traditional chemotherapeutics (doxorubicin, paclitaxel, and cisplatin). The bone marrow microenvironment is extremely sensitive to chemotherapeutics, so targeting these chemotherapies specifically to bone with the goal of minimizing off-target effects can lead to significant toxicity to healthy bone cells and bone itself. Importantly, the lead formulation here elicited minimal systemic toxicity upon i.v. administration with an aggressive treatment schedule. Further, the application of highly controlled RAFT-based chemistry allowed us to tune the targeting ligand content in order to demonstrate the functional balance between high bone binding and desirable systemic PK, both of which can contribute to efficient delivery to tumors associated with bone. Interestingly, the lead formulation also showed dual benefits, with both the bone targeting ligand Aln and the loaded therapeutic GANT58 significantly contributing to bone protection outcomes. Finally, this study elucidated through histological analysis that there is a spatial heterogeneity in the GANT58-BTNP effects on tumor cell proliferation, with this therapy specifically blocking growth into and destruction of the mineralized phase of bone. This provides insight into the role that the bone microenvironment plays in driving tumor progression and suggests that targeted GANT58 delivery combined with chemotherapy or molecularly-targeted therapy should be investigated to yield treatments that will improve both patient quality of life and survival.

Materials & Methods

Cell Lines and Reagents. The human breast cancer cell line MDA-MB-231 was obtained from ATCC and a bone metastatic variant generated by the present inventors was used for all in vitro and in vivo experiments, as previously published. MDA-MB-231 cells were maintained in DMEM (Cell-gro) plus 10% Fetal Bovine Serum (FBS; Hyclone Laboratories) and 1% penicillin/streptomycin (P/S; Mediatech). All cell lines are routinely tested for changes in cell growth and gene expression. GANT58 was purchased from Santa Cruz Biotechnology (Dallas, TX, USA), all other reagents were purchased from Sigma Aldrich (St. Louis, MO, USA) unless otherwise specified.

Synthesis of Hydroxyl End-Functionalized Poly(propylene sulfide) ($PPS_{135}$-OH) A terminal hydroxyl end functional poly(propylene sulfide) polymer was synthesized by anionic ring polymerization of the three membered cyclic propylene sulfide monomer using DBU/1-buthane thiol followed by an end-functionalization with 2-iodoethanol. In brief, 1,8-diazabicyclo[5.4.0]undec 7-ene (DBU) (3 mmol, 0.46 g, 0.45 mL) in dry THF (15 mL) was transferred to a heat dried and nitrogen flushed 100 mL round bottomed flask and degassed for 30 min. The flask was submerged into an ice bath, and a degassed solution of 1-butane thiol (1 mmol, 0.122 g, 0.138 mL) in THF (10 mL) was added drop wise at 0° C. After 30 min, freshly dried, distilled, and degassed propylene sulfide (135 mmol, 9.99 g, 10.56 mL) monomer was added to the reaction mixture, and temperature was maintained at 0° C. for another 30 min. The polymerization was carried for another 150 min, quenched by addition of degassed 2-iodoethanol (4 mmol, 0.68 g, 0.311 mL), and stirred overnight at RT. The next day, the polymer mixture was filtered to remove precipitated salt, and the filtered solution was concentrated under vacuum. The crude polymer was purified by three precipitations into cold methanol (100 mL) from dichloromethane (10 mL) before being vacuum-dried to yield a colorless viscous polymer. The formation of polymer with a terminal hydroxyl functionality was characterized by 1H NMR and GPC. $^1$H NMR (400 MHz; $CDCl_3$): $\delta$(ppm) 1.3-1.4 (s, $CH_3$), 2.5-2.8 (s, —CH), 2.8-3.1 (s, $CH_2$), 3.72 (q, $CH_2$—OH). ($PPS_{135}$-OH, Mn=9,700 g/mol, PDI=1.32).

Synthesis of Poly(propylene sulfide)-4-cyano-4-(ethylsulfanylthiocarbonyl) sulfanylpentanoic acid ($PPS_{135}$-ECT). The PPS-based reversible addition-fragmentation chain-transfer (RAFT) macro chain transfer agent (CTA) was prepared using a Steglich esterification reaction between carboxyl-terminated ECT (RAFT agent) and the terminal hydroxyl groups of the $PPS_{135}$-OH. To a dried flask, $PPS_{135}$-OH (6.0 g, 0.6 mmol), ECT (0.628 g, 2.4 mmol), and 4-dimethylaminopyridine (DMAP, 0.021 g, 0.18 mmol) were transferred and dissolved in DCM and degassed for 15 min. To this flask, N,N'-dicyclohexylcarbodiimide (DCC, 0.495 g, 2.4 mmol) was added and stirred at RT for 24 h. The polymer mixture was filtered to remove precipitated dicyclohexyl urea and concentrated under vacuum. The crude polymer mixture was diluted with DCM (10 mL) and subsequently purified by three precipitations into 250 mL of cold methanol. $^1$H NMR (400 MHz; $CDCl_3$): $\delta$(ppm) 1.35 (t, 3H, —S—$CH_2$—$CH_3$), 1.3-1.4 (s, 3H, $CH_3$), 1.88 (s, —C(CN)—$CH_3$), 2.4-2.67 (m, 4H, —$CH_2$—$CH_2$—S), 2.5-2.8 (broad s, S—CH), 2.8-3.1 (broad s, 2H, $CH_2$), 3.34 (q, —S—$CH_2$—$CH_3$), 4.2 (t, —$OCH_2$—$CH_2$). ($PPS_{135}$-ECT, $M_{n,GPC}$=9,900 g/mol, PDI=1.32).

Synthesis of Poly(propylene sulfide)-b-poly(pentafluorophenyl acrylate-co-dimethylacrylamide) $PPS_{135}$-b-P(PF-$PA_x$-co-$DMA_y$)$_{150}$. The diblock copolymer $PPS_{135}$-b-P(PF-$PA_x$-co-$DMA_y$)$_{150}$ was synthesized via RAFT polymerization using AIBN as the initiator at a 5:1 molar ratio of $PPS_{135}$-ECT to AIBN. In order to minimize PFPA hydrolysis during synthesis, anhydrous solvents were used in all synthesis steps. In a 10 mL round-bottom reaction flask, $PPS_{135}$-ECT (0.3 g, 0.03 mmol) was co-dissolved with stoichiometric amounts of pentafluorophenyl acrylate (PFPA) and dimethylacrylamide (DMA) in 1:1 DMF to 1,4-dioxane (4 mL) to achieve a final second block chain length of 150, where the PFPA amount was varied from 0 to 100% PFPA in the 150-unit second block with the balance DMA. A solution of AIBN (0.98 mg, 0.006 mmol) in 1,4-dioxane was added to the reaction mixture and degassed for 15 min by bubbling ultrahigh purity nitrogen through the reaction mixture. The reaction flask was then submerged in a 70° C. oil bath and polymerization was allowed to proceed for 24 h. The final polymerization mixture was precipitated twice in cold diethyl ether and dried under vacuum overnight to yield a light-yellow polymer.

Synthesis of $PPS_{135}$-b-P($Aln_x$-co-$DMA_y$)$_{150}$ and Fluorescent $PPS_{135}$-b-P($Aln_x$-co-$DMA_y$)$_{150}$. The amine-reactive PFPA group of $PPS_{135}$-b-P($PFPA_x$-co-$DMA_y$)$_{150}$ was used to graft alendronate (Aln), an amine-terminated bisphosphonate, to the polymer backbone. $PPS_{135}$-b-P($PFPA_x$-co-$DMA_3$)$_{150}$ (0.013 mmol, 0.3 g), triethylamine (0.013 mmol, 1.8 μL), Aln (10% excess of PFPA molar content) were added to a dry round-bottom flask and dissolved in DMSO (4 mL) and submerged in a 50° C. oil bath. The amine-conjugation was allowed to proceed for 24 h at 50° C. The reaction contents were then dialyzed against deionized water for 48 h followed by lyophilization. For fluorescent-labeling of polymers, Cy7-amine or Cy5-amine (0.013 mmol) was added to the reaction flask prior to Aln addition and reaction allowed to proceed 24 h. To the same reaction flask, Aln was then added and reaction proceeded as described. The resulting polymer was then dialyzed first against methanol for 48 h until disappearance of fluorophore color and then against deionized water for 48 h.

Fourier Transform Infrared (FT-IR) Analysis. To confirm that the synthesized polymers had varied Aln concentrations, Fourier transform infrared (FT-IR) spectra were recorded on a Bruker Tensor 27 system (Billerica, MA). Briefly, Aln and polymers with different percentage of Aln (5 mg) were mixed with IR-grade KBr (100 mg), and pellets were prepared on a KBr press (Specac, Slough, UK). The presence of Aln was identified based on the presence of the stretching vibration of the P—O bond in Aln.

Determination of Aln Content. A fully water-soluble cation-chelation assay adapted from previously established methods was developed in order to measure the polymer-bound Aln relying on the competitive chelation of $Ca^{2+}$ with the well-established calcium quantification chromagen, o-cresolphthalein complexone. 10.3 mg of o-cresolphthalein complexone was dissolved into 100 mL of 0.1 M glycine buffer (pH 10) and used to dissolve various concentration of Aln (standard curve, 0-2 mM) or Aln-containing polymers. 200 uL of each was added to a well of a 96-well plate and an absorbance reading was measured at 570 nm. The plate was then removed and 5 uL of a 1 mM $CaCl_2$) solution was added to each well. The plate was gently shaken for 5 minutes and the absorbance measured again at 570 nm. Absorbance of the Aln reading with $CaCl_2$) was subtracted by the corresponding well/reading without $CaCl_2$) and used to form a standard curve ($R^2$=0.97-0.99). Different concentrations of the Aln-polymer were also used in order to ensure the polymer fell within the linear range of the assay (typically characterized as e.g., the region where doubling the polymer concentration resulted in doubling of absorbance difference ($+CaCl_2$) vs $-CaCl_2$)), corresponding to the 0.1-0.7 mM region of the alendronate standard curve). The number of Aln per polymer chain were then estimated based on the molecular weight of the polymer.

GANT58-BTNP Formulation and Characterization. GANT58-loaded nanoparticles (GANT58-BTNPs) were fabricated by either the bulk solvent evaporation method or nanoprecipitation method. $PPS_{135}$-b-P($Aln_x$-co-$DMA_y$)$_{150}$ and GANT58 were dissolved in chloroform (solvent evaporation) or methanol (nanoprecipitation) and added dropwise to stirring phosphate-buffered saline (PBS, 1 mL). For the solvent evaporation method, the biphasic solution was left stirring overnight to allow for chloroform evaporation and micelle formation. For nanoprecipitation, the solution was allowed to stir for 1 h, after which the methanol was removed from the solution via rotary evaporation. The resulting micelle solution was filtered by syringe filtration (0.45 µm cutoff) producing the final GANT58-BTNP formulation. The same technique without GANT58 was used to create empty $PPS_{135}$-b-P($Aln_x$-co-$DMA_y$)$_{150}$ NPs (Empty-BTNPs). The hydrodynamic diameter ($D_h$) and zeta potential ($\zeta$) of the GANT58-BTNPs and Empty-BTNPs was measured by dynamic light scattering (DLS) at a concentration of 1 mg/mL in PBS (pH 7.4) via a Malvern Zetasizer Nano-ZS (Malvern Instruments Ltd., Worcestershire, UK) equipped with a 4 mW He—Ne laser operating at X=632.8 nm. Transmission electron microscopy (TEM) samples were prepared as previously described. Briefly, 5 µL of GANT58-BTNPs were pipetted onto a carbon TEM grid (Ted Pella, Inc., Redding, CA, USA), blotted dry after 60 s, and counterstained with 1% uranyl acetate for 20 s, and allowed to vacuum dry overnight. The grids were imaged on an FEI Tecnai Osiris microscope (Hillsboro, OR, USA) operating at 200 kV for TEM and Scanning Transmission Electron Microscopy Energy Dispersive X-ray Spectroscopy (STEM-EDS).

The fluorescent properties of GANT58 were used to measure GANT58 loading within the BTNPs. GANT58-BTNPs in PBS (50 µL) were pipetted into a 96-well plate and dissolved by adding an equal amount of DMF. A GANT58 standard curve in the same solvent (1:1 DMF:PBS) was prepared on the same plate. Fluorescence intensity of GANT58 (ex. 485 nm, em. 590 nm) was measured on a micro plate reader (Synergy H1, Biotek, Winooski, VT) and GANT58 concentration was calculated from the standard curve. Loading was calculated as mass of GANT58 per total mass of BTNPs (%), whereas the encapsulation efficiency was calculated as the mass of GANT58 in the BTNPs per the mass of GANT58 introduced (%).

Critical Micelle Concentration (CMC). The critical micelle concentration was measured as previously described. Nile Red (NR) was used as the encapsulated cargo due to its hydrophobic fluorescence properties and its similar molecular weight to GANT58. NR is ideal for identifying intact micelles due to its fluorescence in hydrophobic environments and minimal fluorescence in aqueous environments. Nile Red (NR)-loaded $PPS_{135}$-b-P($Aln_x$-co-$DMA_y$)$_{150}$ micelles (NR-BTNPs) were fabricated by solvent evaporation and serial dilutions of the NR-BTNPs were prepared in PBS. NR fluorescence (ex. 535 nm, em. 612 nm) was then read on a micro plate reader (Synergy H1, Biotek, Winooski, VT) and the intersection point on the semi-log plot of NR fluorescence versus polymer concentration was defined as the CMC as previously described.

BTNP Stability Measurements. BTNP stability was tracked by measuring BTNP hydrodynamic diameter in salt and serum using DLS. BTNPs were prepared at a concentration of 100 µg/mL in solutions of NaCl (0.5M) or fetal bovine serum (FBS, 50% in PBS) and incubated for 2 h prior to DLS measurements. Hydrodynamic diameters were compared to control BTNP solutions prepared in PBS. Serum stability was further investigated using a Forster resonance energy transfer (FRET) based assay described previously. Briefly, BTNPs were co-loaded with the FRET pair DiI and DiO and incubated in 50% FBS. Fluorescence measurements were taken at emission wavelengths of 517 nm and 573 nm after excitation at 480 nm over an 8 h time period on a fluorescence micro plate reader. FRET efficiency was calculated as $$\% \text{ FRET} = \frac{I_{573}}{I_{573} + I_{517}} \times 100$$

Macrophage Uptake. RAW 264.7 macrophages were seeded at 25,000 cells/well in a 24-well plate. After 24 h, cells were incubated with DMEM containing 1 mg/mL Cy5-grafted GANT58-BTNPs for 4 h. Cells were then washed 3× with PBS containing 1% bovine serum albumin (BSA), harvested using a cell scraper, and pelleted. Cell pellets were resuspended in PBS containing 0.04% trypan blue and run through a flow cytometer (BD LSR Fortessa, BD Biosciences, Franklin Lakes, NJ, USA). Cy5 fluorescence (ex. 640 em. 670) was monitored and 1,000 cells collected for each measurement and mean Cy5 fluorescence was normalized to original BTNP solution fluorescence. Untreated RAW 264.7 cells were used as negative controls.

In Vitro Bone-Binding Kinetics. The bone-binding kinetics of the BTNPs was assessed using nanocrystalline hydroxyapatite (nHA, Sigma) as the substitute for bone in vitro as described previously. Briefly, NR-BTNPs were prepared as described and incubated at 1 mg/mL—or at varying concentrations for adsorption isotherm experiments—with 40 mg nHA in 4 mL PBS. Samples were then placed on a stir plate (Cimarec, Thermo Scientific, Waltham, MA) in a 37° C. incubator. At predetermined time points, samples were centrifuged at 1500 rpm for 5 min and a 100 µL sample of the supernatant was removed and measured for NR fluorescence intensity (ex. 535 nm, em. 612 nm) on a micro plate reader (Synergy H1, Biotek, Winooski, VT). NR fluorescence in the nHA-containing supernatant was divided by fluorescence in samples prepared identically but without nHA in order to calculate the fraction of unbound NPs, which was then converted to a percentage and subtracted from 100 to obtain the % HA bound.

Mineralization Assay. Human mesenchymal stem cells (hMSCs) were seeded in a 24-well plate at 50,000 cells/well and allowed to proliferate for 48 hr in MSC Growth Medium 2 (PromoCell) as previously described. Media was then changed to MSC Osteogenic Differentiation Medium (Pro-moCell) treated with vehicle (DMSO), free GANT58 (40 μM), BTNPs (10% Aln, 40 μM equivalent polymer dose), or GANT58-NPs (10% Aln-GANT58, 40 μM GANT58) to induce osteoblast differentiation. After 14 days culture with media changes every third day, cells were then washed with PBS, fixed in 10% formalin for 45 min, and stained with Alizarin Red S (80 mM) for 30 min. Cells were then washed 5× with water and observed via an inverted microscope. 5% SDS was then used to extract the Alizarin dye by incubation in the surfactant for 1 hr under constant shaking. The extracted Alizarin dye was then read on a plate reader at OD 405 nm.

Osteoclastogenesis Assay. Mouse bone marrow-derived stromal cells (BMSCs) were isolated from C57BL/6J mice for use in an osteoclastogenesis coculture assay as described previously. Briefly, hindlimbs were dissected, and both ends of the femora and tibiae were cut. BMSCs were collected via centrifugation and plated on 100 mm culture dishes in α-MEM. Nonadherent cells were then collected and pelleted after 2 hr. The BMSCs (500,000 cells/well) and MDA-MB-231-bone cells (1000 cells/well) were seeded in 48-well plates in 300 μL media supplemented with 10 ng/mL TGF-β (day 1). On day 1, treatments began with free GANT58 (40 μM), BTNPs (10% Aln, 40 μM equivalent polymer dose), and GANT58-BTNPs (10% Aln-GANT58, 40 μM GANT58). On each subsequent day, media was replaced with fresh α-MEM supplemented with treatments until fixation on day 6. Cells were fixed, stained for tartrate-resistant acid phosphatase (TRAP), and counterstained with hematoxylin using a TRAP kit (Sigma) per the manufacturer's instructions. TRAP-positive cells with more than 2 nuclei were counted as osteoclasts. An experimental group without MDA-MB-231-bone cells (no tumor) served as a negative control.

Hydrogen Peroxide- ($H_2O_2$—) Dependent Drug Release. The ROS-sensitive behavior of the BTNPs was measured as previously described, using $H_2O_2$ as the ROS-species. Briefly, NR-BTNPs prepared as described were exposed to a range of concentrations (1-2000 mM) of $H_2O_2$. Fluorescence intensity of NR was monitored in a 96 well plate using a micro plate reader (Synergy H1, Biotek, Winooski, VT). NR release caused by BTNP oxidation and destabilization was kinetically measured based on loss in NR fluorescence. The percent NR release was calculated from the NR fluorescence loss in the presences of $H_2O_2$ by comparing the fluorescence reading from that of the fluorescence value prior to $H_2O_2$ addition and presented as a percent NR remaining. This value was then subtracted from 100% and presented as percent NR release.

Biodistribution. CD-1 female mice (4-6 weeks old, Envigo, n=5) were injected with GANT58-loaded Cy5-grafted PPS$_{135}$-b-P(Aln$_{15}$-co-DMA$_{135}$) (GANT58-Cy5BTNPs) via tail vein injection (8 mg/kg GANT58). At 24 hr post NP-injection mice were sacrificed and organs and long bones (forelimbs and hindlimbs) were imaged on an IVIS Lumina III imaging system (Caliper Life Sciences, Hopkinton, MA). ROI analysis was conducted on the images using the IVIS software. For GANT58 biodistribution, female athymic nude mice (4-6 weeks old, Envigo, n=5) were injected with 2.5×10$^5$ MDA-MB-231-bone cells in 10 μL PBS into the left tibia under isoflurane anesthesia as previously described. As a control, the contralateral limb was injected with 10 μL PBS. After two weeks for tumor establishment, 10% Aln-GANT58 BTNPS or 0% Aln-GANT58 BTNPs were administered via tail-vein injection. After 24 h circulation, mice were sacrificed and limbs and organs were flash frozen in liquid nitrogen. Limbs were then cryo-milled (SPEX SamplePrep, Metuchen, NJ, USA) and resulting milled powder was weighed. Liquid-liquid extraction was conducted in a 6:1 DCM:PBS solution and DCM layer containing GANT58 was collected. After removing DCM by vacuum, GANT58 was reconstituted and concentration was measured by high performance liquid chromatography (HPLC).

Cryohistology. Rag 2−/− mice (female, 4-6 weeks old, n=3) were inoculated with 2.5×10$^5$ MDA-MB-231-bone cells in 10 μL PBS into the left tibia under isoflurane anesthesia as previously described. Cy5BTNPs were administered via a single tail vein injection and mice were sacrificed at 24 hr. Tibiae were dissected and frozen before being embedded in Optimal Cutting Temperature Compound (Fisher Healthcare). Serial sections with a thickness of 5um and 20 um were collected using the Multi-Purpose Cryo-section Preparation Kit from Section-Lab Co. Ltd. (Yokohama, Japan) and fixed in 10% formalin to either be stained with hematoxylin and eosin or used for fluorescent imaging respectively. The 5 um samples were fixed in 10% formalin for 30 seconds and rinsed with deionized water. The sections were then stained with Hematoxylin Solution, Gill No. 3, rinsed with deionized water, stained with Eosin from Section-Lab Co. Ltd., and rinsed again with deionized water. The sections were rinsed with 100% ethanol then with deionized water before being mounted onto a slide with Prolong Gold mounting media (Thermo Fisher). The 20 um samples were fixed in 10% formalin for 30 seconds and rinsed with deionized water. The sections were then mounted onto a slide with Prolong Gold mounting media with DAPI (Thermo Fisher).

Pharmacokinetics. Cy5-grafted GANT58-BTNPs were injected into Rag 2−/− mice (female, 4-6 weeks old, n=5) via retroorbital injection (8 mg/kg GANT58, 100 μL injection) under isoflurane anesthesia. At 1 minute, 15 min, 30 min, 1 h, 2 h, 4 h, 12 h, and 24 h, a small volume of blood (<5 μL) was drawn via tail nick, collected in a heparinized capillary tube, and dispensed into PCR tubes. The whole blood samples contained in PCR tubes were then frozen at −80° C. Samples were thawed at time of analysis, diluted 40× in PBS, and then read on a Take3 microvolume plate (Biotek) in a Synergy H1 fluorescence plate reader (Biotek). Background fluorescence was subtracted using a blank whole blood sample control. A standard curve was made by adding Cy5-grafted BTNPs into mouse blood that was then frozen until time of analysis, and was then diluted 40× as were the samples.

Orthotopic Mouse Model of Early Bone Metastasis. Mice (athymic nude, female, 4-6 weeks old, Envigo) were inoculated with 1×10$^5$ GFP-expressing MDA-MB-231 cells via intracardiac injection into the left cardiac ventricle while under isoflurane anesthesia, as previously described. Mice were treated 5× per week via 100 μL tail vein injections with GANT58-BTNPs (10% Aln formulation, 8 mg/kg, n=12), GANT58-NPs (0% Aln formulation, 8 mg/kg, n=12), unloaded BTNPs of the same formulations (10% Aln and 0% Aln, n=12 per group), or PBS (control). Mice were imaged weekly via radiographic imaging to track tumor progression and sacrificed at 4 weeks.

Radiographic Imaging. Starting one week post-tumor cell inoculation, mice were imaged via radiographic imaging using a Faxitron LX-60. Mice were anesthetized using isoflurane and laid in a prone position on the imaging platform. Images were acquired at 35 kVp for 8 seconds.

Lesion area and number in the combined hindlimbs of the mice were measured using quantitative image analysis software (Metamorph, Molecular Devices, Inc.) by region of interest analysis. All data are represented as mean lesion area and number per mouse.

Micro-Computed Tomography. A high-resolution µCT 50 system (Scanco Medical) was used to analyze the mouse tibiae bone volume and microarchitecture. Tomographic images were acquired of hindlimbs in 70% ethanol (70 kVp, 12 µm voxel size, 300 ms integration time). µCT images were reconstructed, filtered ($\sigma$=0.2, support=1.0) and thresholded at 230. Tibiae were contoured starting 10 slices below the growth plate and continued 100 slices in the distal direction using the Scanco software algorithm. Images of individual tibiae were analyzed using the Scanco Medical Imaging software to determine the morphometric parameters.

Histology/Histomorphometry. At autopsy, tibiae were removed and fixed in 10% formalin (Fisher Scientific) for 48 hours at room temperature. Fixed tibiae were then stored at 4° C. in 70% ethanol and subsequently decalcified in 10% EDTA for 2 weeks at 4° C. Specimens were then embedded in paraffin and sectioned into 5 µm sections via microtomy. Bone sections were stained with hematoxylin & eosin (H&E), orange G, and phloxine, and examined under a microscope. Tumor burden in the tibiae was quantified using Metamorph software (Molecular Devices, Inc.) and region of interest analysis. For osteoclast analysis, bone sections were stained for Tartrate-Resistant Acid Phosphatase (TRAP) utilizing a substrate incubation step (0.2 mg/mL Napthol AS-BI) followed by a color reaction (25 mg/mL Pararosaniline dye) to form a bright red stain in TRAP-positive cells. Sections were then counterstained with hematoxylin, coverslipped, and examined under a microscope and quantified using OsteoMeasure software (OsteoMetrics, Decatur, GA, USA). Liver and kidney were also removed during autopsy. Processing, embedding, sectioning, and H&E staining were performed by the Vanderbilt Translational Pathology Shared Resource (TPSR) per established protocols.

Immunohistochemistry. Ki67 immunohistochemical staining was performed by the Vanderbilt TPSR per established protocols. PTHrP immunohistochemistry was carried out as previously described on decalcified paraffin-embedded tibial sections using a rabbit anti-PTHrP antibody (1:2500, R87). Metamorph software (Molecular Devices, Inc.) was used to quantify PTHrP-positive staining.

Proliferation Assay. In a 96-well plate, MDA-MB-231-bone cells were seeded at 2,000 cells/well in triplicate. Half of wells were pre-coated with 0.5 mm GelMA as a compliant substrate. Vehicle (DMSO) or GANT58 (40 µM) were added to wells after 24 hr. Cell proliferation was determined by MTS assay using the CellTiter 96 Aqueous Non-Radioactive Cell Proliferation Assay kit (Promega) per the manufacturer's instructions. Absorbance values were measured at OD 490 nm on a plate reader and normalized to no cell controls in the respective GelMA coated and uncoated wells.

Statistical Methods. Unless otherwise stated, statistics were determined via a one-way ANOVA with Tukey multiple comparisons test using Prism 7 software. All reported data display mean and standard error unless otherwise noted. $p < 0.05$ was considered statistically significant with $n \geq 3$ for all experiments.

It will be understood that various details of the presently disclosed subject matter can be changed without departing from the scope of the subject matter disclosed herein.

Furthermore, the foregoing description is for the purpose of illustration only, and not for the purpose of limitation.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES (1) Roodman, G. D. Mechanisms of Bone Metastasis. *N. Engl. J. Med.* 2004, 350, 1655-1664.
(2) Onishi, T.; Hayashi, N.; Theriault, R. L.; Hortobagyi, G. N.; Ueno, N. T. Future Directions of Bone-Targeted Therapy for Metastatic Breast Cancer. *Nat. Rev. Clin. Oncol.* 2010, 7, 641-651.
(3) Baron, R.; Ferrari, S.; Russell, R. G. G. Denosumab and Bisphosphonates: Different Mechanisms of Action and Effects. *Bone* 2011, 48, 677-692.
(4) Pozzi, S.; Vallet, S.; Mukherjee, S.; Cirstea, D.; Vaghela, N.; Santo, L.; Rosen, E.; Ikeda, H.; Okawa, Y.; Kiziltepe, T.; Schoonmaker, J.; Xie, W.; Hideshima, T.; Weller, E.; Bouxsein, M. L.; Munshi, N. C.; Anderson, K. C.; Raje, N. High-Dose Zoledronic Acid Impacts Bone Remodeling with Effects on Osteoblastic Lineage and Bone Mechanical Properties. *Clin. Cancer Res.* 2009, 15, 5829-5839.
(5) Gnant, M.; Pfeiler, G.; Dubsky, P. C.; Hubalek, M.; Greil, R.; Jakesz, R.; Wette, V.; Balic, M.; Haslbauer, F.; Melbinger, E.; Bjelic-Radisic, V.; Artner-Matuschek, S.; Fitzal, F.; Marth, C.; Sevelda, P.; Mlineritsch, B.; Steger, G. G.; Manfreda, D.; Exner, R.; et al. Adjuvant Denosumab in Breast Cancer (ABCSG-18): A Multicentre, Randomised, Double-Blind, Placebo-Controlled Trial. *Lancet* 2015, 386, 433-443.
(6) Lauth, M.; Bergstrom, A.; Shimokawa, T.; Toftgård, R. Inhibition of GLI-Mediated Transcription and Tumor Cell Growth by Small-Molecule Antagonists. *Proc. Natl. Acad. Sci. U.S.A.* 2007, 104, 8455-8460.
(7) Cannonier, S. A.; Gonzales, C. B.; Ely, K.; Guelcher, S. A.; Sterling, J. A. Hedgehog and TGFβ Signaling Converge on Gli2 to Control Bony Invasion and Bone Destruction in Oral Squamous Cell Carcinoma. *Oncotarget* 2016, 7, 76062-76075.
(8) Mundy, G. R. Mechanisms of Bone Metastasis. *Cancer* 1997, 80, 1546-1556.
(9) Yin, J. J.; Selander, K.; Chirgwin, J. M.; Dallas, M.; Grubbs, B. G.; Wieser, R.; Massagué, J.; Mundy, G. R.; Guise, T. A. TGF-β Signaling Blockade Inhibits PTHrP Secretion by Breast Cancer Cells and Bone Metastases Development. *J. Clin. Invest.* 1999, 103, 197-206.
(10) Briscoe, J.; Therond, P. P. The Mechanisms of Hedgehog Signalling and Its Roles in Development and Disease. *Nat. Rev. Mol. Cell Biol.* 2013, 14, 416-429.
(11) Pasca di Magliano, M.; Hebrok, M. Hedgehog Signalling in Cancer Formation and Maintenance. *Nat. Rev. Cancer* 2003, 3, 903-911.
(12) Swami, A.; Reagan, M. R.; Basto, P.; Mishima, Y.; Kamaly, N.; Glavey, S.; Zhang, S.; Moschetta, M.; Seevaratnam, D.; Zhang, Y.; Liu, J.; Memarzadeh, M.; Wu, J.; Manier, S.; Shi, J.; Bertrand, N.; Lu, Z. N.; Nagano, K.; Baron, R.; et al. Engineered Nanomedicine for Myeloma and Bone Microenvironment Targeting. *Proc. Natl. Acad. Sci. U.S.A.* 2014, 111, 10287-10292.
(13) Cole, L. E.; Vargo-Gogola, T.; Roeder, R. K. Targeted Delivery to Bone and Mineral Deposits Using Bisphosphonate Ligands. *Adv. Drug Deliv. Rev.* 2016, 99, 12-27.

(14) Qiao, H.; Cui, Z.; Yang, S.; Ji, D.; Wang, Y.; Yang, Y.; Han, X.; Fan, Q.; Qin, A.; Wang, T.; He, X. P.; Bu, W.; Tang, T. Targeting Osteocytes to Attenuate Early Breast Cancer Bone Metastasis by Theranostic Upconversion Nanoparticles with Responsive Plumbagin Release. *ACS Nano* 2017, 11, 7259-7273.

(15) Liu, P.; Sun, L.; Zhou, D.; Zhang, P.; Wang, Y.; Li, D.; Li, Q.; Feng, R.-J. Development of Alendronate-Conjugated Poly (Lactic-Co-Glycolic Acid)-Dextran Nanoparticles for Active Targeting of Cisplatin in Osteosarcoma. *Sci. Rep.* 2015, 5, 17387.

(16) Uludag, H.; Yang, J. Targeting Systemically Administered Proteins to Bone by Bisphosphonate Conjugation. *Biotechnol. Prog.* 2002, 18, 604-611.

(17) Gittens, S. A.; Bagnall, K.; Matyas, J. R.; Lobenberg, R.; Uludag, H. Imparting Bone Mineral Affinity to Osteogenic Proteins through Heparin-Bisphosphonate Conjugates. *J. Control. Release* 2004, 98, 255-268.

(18) Bansal, G.; Wright, J. E. I.; Zhang, S.; Zernicke, R. F.; Uludag, H. Imparting Mineral Affinity to Proteins with Thiol-Labile Disulfide Linkages. *J. Biomed. Mater. Res. —Part A* 2005, 74, 618-628.

(19) Wright, J. E. I.; Gittens, S. A.; Bansal, G.; Kitov, P. I.; Sindrey, D.; Kucharski, C.; Uludağ, H. A Comparison of Mineral Affinity of Bisphosphonate-Protein Conjugates Constructed with Disulfide and Thioether Linkages. *Biomaterials* 2006, 27, 769-784.

(20) Murphy, M. B.; Hartgerink, J. D.; Goepferich, A.; Mikos, A. G. Synthesis and in Vitro Hydroxyapatite Binding of Peptides Conjugated to Calcium-Binding Moieties. *Biomacromolecules* 2007, 8, 2237-2243.

(21) Yamashita, S.; Katsumi, H.; Hibino, N.; Isobe, Y.; Yagi, Y.; Tanaka, Y.; Yamada, S.; Naito, C.; Yamamoto, A. Development of PEGylated Aspartic Acid-Modified Liposome as a Bone-Targeting Carrier for the Delivery of Paclitaxel and Treatment of Bone Metastasis. *Biomaterials* 2018, 154, 74-85.

(22) Wang, D.; Miller, S. C.; Shlyakhtenko, L. S.; Portillo, A. M.; Liu, X. M.; Papangkorn, K.; Kopečlcová, P.; Lyubchenko, Y.; Higuchi, W. I.; Kopeček, J. Osteotropic Peptide That Differentiates Functional Domains of the Skeleton. *Bioconjug. Chem.* 2007, 18, 1375-1378.

(23) Chen, F.; Jia, Z.; Rice, K. C.; Reinhardt, R. A.; Bayles, K. W.; Wang, D. The Development of Dentotropic Micelles with Biodegradable Tooth-Binding Moieties. *Pharm. Res.* 2013, 30, 2808-2817.

(24) Yamashita, S.; Katsumi, H.; Hibino, N.; Isobe, Y.; Yagi, Y.; Kusamori, K.; Sakane, T.; Yamamoto, A. Development of PEGylated Carboxylic Acid-Modified Polyamidoamine Dendrimers as Bone-Targeting Carriers for the Treatment of Bone Diseases. *J. Control. Release* 2017, 262, 10-17.

(25) Zhou, Z.; Fan, T.; Yan, Y.; Zhang, S.; Zhou, Y.; Deng, H.; Cai, X.; Xiao, J.; Song, D.; Zhang, Q.; Cheng, Y. One Stone with Two Birds: Phytic Acid-Capped Platinum Nanoparticles for Targeted Combination Therapy of Bone Tumors. *Biomaterials* 2019, 194, 130-138.

(26) He, C.; Hu, Y.; Yin, L.; Tang, C.; Yin, C. Effects of Particle Size and Surface Charge on Cellular Uptake and Biodistribution of Polymeric Nanoparticles. *Biomaterials* 2010, 31, 3657-3666.

(27) Xiao, K.; Li, Y.; Luo, J.; Lee, J. S.; Xiao, W.; Gonik, A. M.; Agarwal, R. G.; Lam, K. S. The Effect of Surface Charge on in Vivo Biodistribution of PEG-Oligocholic Acid Based Micellar Nanoparticles. *Biomaterials* 2011, 32, 3435-3446.

(28) Gupta, M. K.; Meyer, T. a.; Nelson, C. E.; Duvall, C. L. Poly(PS-b-DMA) Micelles for Reactive Oxygen Species Triggered Drug Release. *J. Control. Release* 2012, 162, 591-598.

(29) Gupta, M. K.; Martin, J. R.; Werfel, T. A.; Shen, T.; Page, J. M.; Duvall, C. L. Cell Protective, ABC Triblock Polymer-Based Thermoresponsive Hydrogels with ROS-Triggered Degradation and Drug Release. *J. Am. Chem. Soc.* 2014, 136, 14896-14902.

(30) Poole, K. M.; Nelson, C. E.; Joshi, R. V.; Martin, J. R.; Gupta, M. K.; Haws, S. C.; Kavanaugh, T. E.; Skala, M. C.; Duvall, C. L. ROS-Responsive Microspheres for on Demand Antioxidant Therapy in a Model of Diabetic Peripheral Arterial Disease. *Biomaterials* 2015, 41, 166-175.

(31) Gupta, M. K.; Martin, J. R.; Dollinger, B. R.; Hattaway, M. E.; Duvall, C. L. Thermogelling, ABC Triblock Copolymer Platform for Resorbable Hydrogels with Tunable, Degradation-Mediated Drug Release. *Adv. Funct. Mater.* 2017, 27, 1704107.

(32) Ross, R. D.; Roeder, R. K. Binding Affinity of Surface Functionalized Gold Nanoparticles to Hydroxyapatite. *J. Biomed. Mater. Res. —Part A* 2011, 99 A, 58-66.

(33) Ross, R. D.; Cole, L. E.; Roeder, R. K. Relative Binding Affinity of Carboxylate-, Phosphonate-, and Bisphosphonate-Functionalized Gold Nanoparticles Targeted to Damaged Bone Tissue. *J. Nanoparticle Res.* 2012, 14, 1175.

(34) Li, C.; Zhang, Y.; Chen, G.; Hu, F.; Zhao, K.; Wang, Q. Engineered Multifunctional Nanomedicine for Simultaneous Stereotactic Chemotherapy and Inhibited Osteolysis in an Orthotopic Model of Bone Metastasis. *Adv. Mater.* 2017, 29, 1605754.

(35) Uddin, M. J.; Werfel, T. A.; Crews, B. C.; Gupta, M. K.; Kavanaugh, T. E.; Kingsley, P. J.; Boyd, K.; Marnett, L. J.; Duvall, C. L. Fluorocoxib A Loaded Nanoparticles Enable Targeted Visualization of Cyclooxygenase-2 in Inflammation and Cancer. *Biomaterials* 2016, 92, 71-80.

(36) Wang, L.; Kilcher, G.; Tirelli, N. Synthesis and Properties of Amphiphilic Star Polysulfides. *Macromol. Biosci.* 2007, 7, 987-998.

(37) Du, F.; Liu, Y. G.; Scott, E. A. Immunotheranostic Polymersomes Modularly Assembled from Tetrablock and Diblock Copolymers with Oxidation-Responsive Fluorescence. *Cell. Mol. Bioeng.* 2017, 10, 357-370.

(38) Costa, A.; Scholer-Dahirel, A.; Mechta-Grigoriou, F. The Role of Reactive Oxygen Species and Metabolism on Cancer Cells and Their Microenvironment. *Semin. Cancer Biol.* 2014, 25, 23-32.

(39) Szatrowski, T. P.; Nathan, C. F. Production of Large Amounts of Hydrogen Peroxide by Human Tumor Cells. *Cancer Res.* 1991, 51, 794-798.

(40) Napoli, A.; Valentini, M.; Tirelli, N.; Muller, M.; Hubbell, J. A. Oxidation-Responsive Polymeric Vesicles. *Nat. Mater.* 2004, 3, 183-189.

(41) Šprincl, L.; Vacik, J.; Kopeček, J.; Lim, D. Biological Tolerance of Poly(N-substituted Methacrylamides). *J. Biomed. Mater. Res.* 1971, 5, 197-205.

(42) Ulbrich, W.; Lamprecht, A. Fluorimetric Quantification of Clodronate and Alendronate in Aqueous Samples and in Serum. *Talanta* 2011, 84, 437-442.

(43) Corns, C. M.; Ludman, C. J. Some Observations on the Nature of the Calcium-Cresolphthalein Complexone Reaction and Its Relevance to the Clinical Laboratory. *Ann. Clin. Biochem.* 1987, 24, 345-351.

(44) Elmalla, S. F.; Mansour, F. R. A Simple Innovative Spectrofluorometric Method for the Determination of

31

Alendronate in Bulk and in Pharmaceutical Tablets. *Luminescence* 2019, 34, 375-381.

(45) Liedtke, R. J.; Kroon, G.; Batjer, J. D. Centrifugal Analysis with Automated Sequential Reagent Addition: Measurement of Serum Calcium. *Clin. Chem.* 1981, 27, 2025-2028.

(46) Low, S. A.; Kopeček, J. Targeting Polymer Therapeutics to Bone. *Adv. Drug Deliv. Rev.* 2012, 64, 1189-1204.

(47) Leu, C. T.; Luegmayr, E.; Freedman, L. P.; Rodan, G. A.; Reszka, A. A. Relative Binding Affinities of Bisphosphonates for Human Bone and Relationship to Antiresorptive Efficacy. *Bone* 2006, 38, 628-636.

(48) Wang, J.; Wu, W.; Zhang, Y.; Wang, X.; Qian, H.; Liu, B.; Jiang, X. The Combined Effects of Size and Surface Chemistry on the Accumulation of Boronic Acid-Rich Protein Nanoparticles in Tumors. *Biomaterials* 2014, 35, 866-878.

(49) Valencia, P. M.; Pridgen, E. M.; Rhee, M.; Langer, R.; Farokhzad, O. C.; Karnik, R. Microfluidic Platform for Combinatorial Synthesis and Optimization of Targeted Nanoparticles for Cancer Therapy. *ACS Nano* 2013, 7, 10671-10680.

(50) Werfel, T. A.; Jackson, M. A.; Kavanaugh, T. E.; Kirkbride, K. C.; Miteva, M.; Giorgio, T. D.; Duvall, C. Combinatorial Optimization of PEG Architecture and Hydrophobic Content Improves Ternary SiRNA Polyplex Stability, Pharmacokinetics, and Potency in *Vivo*. *J. Control. Release* 2017, 255, 12-26.

(51) Lu, Y.; Zhang, E.; Yang, J.; Cao, Z. Strategies to Improve Micelle Stability for Drug Delivery. *Nano Res.* 2018, 11, 4985-4998.

(52) Kim, S.; Shi, Y.; Kim, J. Y.; Park, K.; Cheng, J.-X. Overcoming the Barriers in Micellar Drug Delivery: Loading Efficiency, in Vivo Stability, and Micelle-Cell Interaction. *Expert Opin. Drug Deliv.* 2010, 7, 49-62.

(53) Bertrand, N.; Leroux, J. C. The Journey of a Drug-Carrier in the Body: An Anatomo-Physiological Perspective. *J. Control. Release* 2012, 161, 152-163.

(54) Perry, J. L.; Reuter, K. G.; Kai, M. P.; Herlihy, K. P.; Jones, S. W.; Luft, J. C.; Napier, M.; Bear, J. E.; Desimone, J. M. PEGylated PRINT Nanoparticles: The Impact of PEG Density on Protein Binding, Macrophage Association, Biodistribution, and Pharmacokinetics. *Nano Lett.* 2012, 12, 5304-5310.

(55) Yamamoto, Y.; Nagasaki, Y.; Kato, Y.; Sugiyama, Y.; Kataoka, K. Long-Circulating Poly(Ethylene Glycol)-Poly(D,L-Lactide) Block Copolymer Micelles with Modulated Surface Charge. *J. Control. Release* 2001, 77, 27-38.

(56) Kamaly, N.; Xiao, Z.; Valencia, P. M.; Radovic-Moreno, A. F.; Farokhzad, 0. C. Targeted Polymeric Therapeutic Nanoparticles: Design, Development and Clinical Translation. *Chem. Soc. Rev.* 2012, 41, 2971-3010.

(57) Clark, A. J.; Wiley, D. T.; Zuckerman, J. E.; Webster, P.; Chao, J.; Lin, J.; Yen, Y.; Davis, M. E. CRLX101 Nanoparticles Localize in Human Tumors and Not in Adjacent, Nonneoplastic Tissue after Intravenous Dosing. *Proc. Natl. Acad. Sci.* 2016, 113, 3850-3854.

(58) Zhao, Y. P.; Ye, W. L.; Liu, D. Z.; Cui, H.; Cheng, Y.; Liu, M.; Zhang, B. Le; Mei, Q. B.; Zhou, S. Y. Redox and PH Dual Sensitive Bone Targeting Nanoparticles to Treat Breast Cancer Bone Metastases and Inhibit Bone Resorption. *Nanoscale* 2017, 9, 6264-6277.

(59) Sterling, J. a.; Oyajobi, B. O.; Grubbs, B.; Padalecki, S. S.; Munoz, S. a.; Gupta, A.; Story, B.; Zhao, M.; Mundy, G. R. The Hedgehog Signaling Molecule Gli2 Induces

32

Parathyroid Hormone-Related Peptide Expression and Osteolysis in Metastatic Human Breast Cancer Cells. *Cancer Res.* 2006, 66, 7548-7553.

(60) Johnson, R. W.; Nguyen, M. P.; Padalecki, S. S.; Grubbs, B. G.; Merkel, A. R.; Oyajobi, B. O.; Matrisian, L. M.; Mundy, G. R.; Sterling, J. A. TGF-Beta Promotion of Gli2-Induced Expression of Parathyroid Hormone-Related Protein, an Important Osteolytic Factor in Bone Metastasis, Is Independent of Canonical Hedgehog Signaling. *Cancer Res.* 2011, 71, 822-831.

(61) Thiyagarajan, S.; Bhatia, N.; Reagan-Shaw, S.; Cozma, D.; Thomas-Tikhonenko, A.; Ahmad, N.; Spiegelman, V. S. Role of GLI2 Transcription Factor in Growth and Tumorigenicity of Prostate Cells. *Cancer Res.* 2007, 67, 10642-10646.

(62) Ruppender, N. S.; Merkel, A. R.; Martin, T. J.; Mundy, G. R.; Sterling, J. A.; Guelcher, S. A. Matrix Rigidity Induces Osteolytic Gene Expression of Metastatic Breast Cancer Cells. *PLoS One* 2010, 5, 1-10.

(63) Page, J. M.; Merkel, A. R.; Ruppender, N. S.; Guo, R.; Dadwal, U. C.; Cannonier, S. A.; Basu, S.; Guelcher, S. A.; Sterling, J. A. Matrix Rigidity Regulates the Transition of Tumor Cells to a Bone-Destructive Phenotype through Integrin B3 and TGF-β Receptor Type II. *Biomaterials* 2015, 64, 33-44.

(64) Discher, D. E. Tissue Cells Feel and Respond to the Stiffness of Their Substrate. *Science* 2005, 310, 1139-1143.

(65) Allen, S. D.; Liu, Y. G.; Bobbala, S.; Cai, L.; Hecker, P. I.; Temel, R.; Scott, E. A. Polymersomes Scalably Fabricated via Flash Nanoprecipitation Are Non-Toxic in Non-Human Primates and Associate with Leukocytes in the Spleen and Kidney Following Intravenous Administration. *Nano Res.* 2018, 11, 5689-5703.

(66) Bamias, A.; Kastritis, E.; Bamia, C.; Moulopoulos, L. A.; Melakopoulos, I.; Bozas, G.; Koutsoukou, V.; Gika, D.; Anagnostopoulos, A.; Papadimitriou, C.; Terpos, E.; Dimopoulos, M. A. Osteonecrosis of the Jaw in Cancer after Treatment with Bisphosphonates: Incidence and Risk Factors. *J. Clin. Oncol.* 2005, 23, 8580-8587.

(67) Coleman, R.; Woodward, E.; Brown, J.; Cameron, D.; Bell, R.; Dodwell, D.; Keane, M.; Gil, M.; Davies, C.; Burkinshaw, R.; Houston, S. J.; Grieve, R. J.; Barrett-Lee, P. J.; Thorpe, H. Safety of Zoledronic Acid and Incidence of Osteonecrosis of the Jaw (ONJ) during Adjuvant Therapy in a Randomised Phase III Trial (AZURE: BIG 01-04) for Women with Stage II/III Breast Cancer. *Breast Cancer Res. Treat.* 2011, 127, 429-438.

(68) Smith, M. R.; Saad, F.; Coleman, R.; Shore, N.; Fizazi, K.; Tombal, B.; Miller, K.; Sieber, P.; Karsh, L.; Damião, R.; Tammela, T. L.; Egerdie, B.; Poppel, H. Van; Chin, J.; Morote, J.; Gómez-Veiga, F.; Borkowski, T.; Ye, Z.; Kupic, A.; et al. Denosumab and Bone-Metastasis-Free Survival in Men with Castration-Resistant Prostate Cancer: Results of a Phase 3, Randomised, Placebo-Controlled Trial. *Lancet* 2012, 379, 39-46.

(69) Yang, S. P.; Kim, T. W. B.; Boland, P. J.; Farooki, A. Retrospective Review of Atypical Femoral Fracture in Metastatic Bone Disease Patients Receiving Denosumab Therapy. *Oncologist* 2017, 22, 438-444.

(70) Carbone, E. J.; Rajpura, K.; Allen, B. N.; Cheng, E.; Ulery, B. D.; Lo, K. W. H. Osteotropic Nanoscale Drug Delivery Systems Based on Small Molecule Bone-Targeting Moieties. *Nanomedicine Nanotechnology, Biol. Med.* 2017, 13, 37-47.

(71) Sinder, B. P.; Zweifler, L.; Koh, A. J.; Michalski, M. N.; Hofbauer, L. C.; Aguirre, J. I.; Roca, H.; McCauley, L. K.

Bone Mass Is Compromised by the Chemotherapeutic Trabectedin in Association With Effects on Osteoblasts and Macrophage Efferocytosis. *J. Bone Miner. Res.* 2017, 32, 2116-2127.

(72) Fan, C.; Georgiou, K. R.; Morris, H. A.; McKinnon, R. A.; Keefe, D. M. K.; Howe, P. R.; Xian, C. J. Combination Breast Cancer Chemotherapy with Doxorubicin and Cyclophosphamide Damages Bone and Bone Marrow in a Female Rat Model. *Breast Cancer Res. Treat.* 2017, 165, 41-51.

(73) Guise, T. A.; Yin, J. J.; Taylor, S. D.; Kumagai, Y.; Dallas, M.; Boyce, B. F.; Yoneda, T.; Mundy, G. R. Evidence for a Causal Role of Parathyroid Hormone-Related Protein in the Pathogenesis of Human Breast Cancer-Mediated Osteolysis. *J. Clin. Invest.* 1996, 98, 1544-1549.

(74) Saito, H.; Tsunenari, T.; Onuma, E.; Sato, K.; Ogata, E.; Yamada-Okabe, H. Humanized Monoclonal Antibody against Parathyroid Hormone-Related Protein Suppresses Osteolytic Bone Metastasis of Human Breast Cancer Cells Derived from MDA-MB-231. *Anticancer Res.* 2005, 25, 3817-3823.

(75) He, Y.; Zhu, T.; Liu, L.; Shi, X.; Lin, Z. Modifying Collagen with Alendronate Sodium for Bone Regeneration Applications. *RSC Adv.* 2018, 8, 16762-16772.

(76) Jackson, M. A.; Werfel, T. A.; Curvino, E. J.; Yu, F.; Kavanaugh, T. E.; Sarett, S. M.; Dockery, M. D.; Kilchrist, K. V.; Jackson, A. N.; Giorgio, T. D.; Duvall, C. L. Zwitterionic Nanocarrier Surface Chemistry Improves SiRNA Tumor Delivery and Silencing Activity Relative to Polyethylene Glycol. *ACS Nano* 2017, 11, 5680-5696.

(77) Hengst, V.; Oussoren, C.; Kissel, T.; Storm, G. Bone Targeting Potential of Bisphosphonate-Targeted Liposomes: Preparation, Characterization and Hydroxyapatite Binding *in Vitro*. *Int. J. Pharm.* 2007, 331, 224-227.

(78) Wang, H.; Liu, J.; Tao, S.; Chai, G.; Wang, J.; Hu, F.-Q.; Yuan, H. Tetracycline-Grafted PLGA Nanoparticles as Bone-Targeting Drug Delivery System. *Int. J. Nanomedicine* 2015, 10, 5671-5685.

(79) Guo, R.; Lu, S.; Merkel, A. R.; Sterling, J. A.; Guelcher, S. A. Substrate Modulus Regulates Osteogenic Differentiation of Rat Mesenchymal Stem Cells through Integrin B1 and BMP Receptor Type IA. *J. Mater. Chem. B* 2016, 4, 3584-3593.

(80) Mbalaviele, G.; Chen, H.; Boyce, B. F.; Mundy, G. R.; Yoneda, T. The Role of Cadherin in the Generation of Multinucleated Osteoclasts from Mononuclear Precursors in Murine Marrow. *J. Clin. Invest.* 1995, 95, 2757-2765.

(81) Michigami, T.; Shimizu, N.; Williams, P. J.; Niewolna, M.; Dallas, S. L.; Mundy, G. R.; Yoneda, T. Cell-Cell Contact between Marrow Stromal Cells and Myeloma Cells via VCAM-1 and Alpha(4)Beta(1)-Integrin Enhances Production of Osteoclast-Stimulating Activity. *Blood* 2000, 96, 1953-1960.

(82) Wright, L. E.; Ottewell, P. D.; Rucci, N.; Peyruchaud, O.; Pagnotti, G. M.; Chiechi, A.; Buijs, J. T.; Sterling, J. A. Murine Models of Breast Cancer Bone Metastasis. *Bonekey Rep.* 2016, 5, 804.

(83) Lam, M. H.; Thomas, R. J.; Loveland, K. L.; Schilders, S.; Gu, M.; Martin, T. J.; Gillespie, M. T.; Jans, D. A. Nuclear Transport of Parathyroid Hormone (PTH)-Related Protein Is Dependent on Microtubules. *Mol. Endocrinol.* 2002, 16, 390-401.

(84) Ansari, N.; Ho, P. W.; Crimeen-Irwin, B.; Poulton, I. J.; Brunt, A. R.; Forwood, M. R.; Divieti Pajevic, P.; Gooi, J. H.; Martin, T. J.; Sims, N. A. Autocrine and Paracrine Regulation of the Murine Skeleton by Osteocyte-Derived Parathyroid Hormone-Related Protein. *J. Bone Miner. Res.* 2018, 33, 137-153.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A polymeric nanocarrier micelle, comprising (poly (propylene sulfide)$_{135}$-b-((alendronate)$_x$-co-(poly(N,N-dimethylacrylamide))$_y$)$_{150}$; wherein x is between 3 and 15 and y is between 135 and 147.

2. The nanocarrier of claim 1, further comprising an active agent encapsulated in the polymeric nanocarrier.

3. The nanocarrier of claim 2, wherein the active agent comprises a hydrophobic small molecule.

4. The nanocarrier of claim 2, wherein the active agent comprises a small molecule therapeutic inhibitor.

5. The nanocarrier of claim 2, wherein the active agent comprises a Gli-inhibitor.

6. The nanocarrier of claim 2, wherein the active agent comprises GANT58.

7. A polymeric nanocarrier comprising (poly(propylene sulfide))$_{135}$-b-((alendronate)$_x$-co-(poly(N,N-dimethylacrylamide))$_y$)$_{150}$; wherein x is between 3 and 15 and y is between 135 and 147.

8. The nanocarrier of claim 7, wherein x is about 15 and y is about 135.

9. A method of treating a bone disease, the method comprising administering a polymeric nanocarrier to a subject in need thereof, the polymeric nanocarrier micelle comprising (poly(propylene sulfide))$_{135}$-b-((alendronate)$_x$-co-(poly(N,N-dimethylacrylamide))$_y$)$_{150}$; wherein x is between 3 and 15 and y is between 135 and 147;

wherein the administration is intravenous.

10. The method of claim 9, wherein the nanocarrier further comprises an active agent encapsulated therein.

11. The method of claim 10, wherein the active agent comprises a small molecule therapeutic inhibitor.

12. The method of claim 10, wherein the active agent comprises a Gli-inhibitor.

13. A composition comprising the polymeric nanocarrier micelle of claim 1, and a carrier formulated for intravenous delivery.

* * * * *